US010337024B2

(12) United States Patent
Schnell et al.

(10) Patent No.: US 10,337,024 B2
(45) Date of Patent: Jul. 2, 2019

(54) PLANTS WITH ENHANCED PHOTOSYNTHESIS AND METHODS OF MANUFACTURE THEREOF

(71) Applicant: THE UNIVERSITY OF MASSACHUSETTS, Boston, MA (US)

(72) Inventors: Danny J. Schnell, Belchertown, MA (US); Mine O. Canakci, Granby, MA (US); Bibin Paulose, Amherst, MA (US); Michelle DaCosta Inguagiato, Wilbraham, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 15/109,349

(22) PCT Filed: Dec. 24, 2014

(86) PCT No.: PCT/US2014/072347

§ 371 (c)(1),
(2) Date: Jun. 30, 2016

(87) PCT Pub. No.: WO2015/103074

PCT Pub. Date: Jul. 9, 2015

(65) Prior Publication Data

US 2016/0326541 A1 Nov. 10, 2016

Related U.S. Application Data

(60) Provisional application No. 61/922,141, filed on Dec. 31, 2013.

(51) Int. Cl.
*C12N 15/82* (2006.01)
*C07K 14/405* (2006.01)

(52) U.S. Cl.
CPC ........ *C12N 15/8269* (2013.01); *C07K 14/405* (2013.01); *C12N 15/8245* (2013.01); *C12N 15/8247* (2013.01); *C12N 15/8261* (2013.01); *C12N 15/8271* (2013.01); *C12N 15/8273* (2013.01); *Y02A 40/146* (2018.01)

(58) Field of Classification Search
CPC .................................................. C12N 15/8269
See application file for complete search history.

(56) References Cited

U.S. PATENT DOCUMENTS

| | | | |
|---|---|---|---|
| 2005/0108790 A1 | 5/2005 | Kaplan et al. |
| 2011/0258734 A1 | 10/2011 | Adams et al. |
| 2013/0007916 A1 | 1/2013 | Spalding |

FOREIGN PATENT DOCUMENTS

| | | |
|---|---|---|
| CN | 103233029 | 8/2013 |
| WO | 02081622 A2 | 10/2002 |
| WO | 2012125737 A2 | 9/2012 |

OTHER PUBLICATIONS

Lieman-Hurwitz, J et al. Plant Biotechnology Journal; 2003, vol. 1; pp. 45-50.*
Price, G.D. et al. Plant Physiology, Jan. 2011; vol. 155, pp. 20-26.*
Spalding, M. Journal of Experimental Botany; 2007, vol. 59, No. 7, pp. 1463-1473.*
Atkinson N., et al. 2016; vol. 14, pp. 1302-1315.*
Skraly, F., Yield10 Bioscience; ASPB 2018: Transporter Manipulation in Food Crops for Increased Yield, pp. 1-17.*
Lieman-Hurwitz, J el al. Plant Biotechnology Journal; 2003, vol. 1; pp. 45-50.*
International Search Report for International Application No. PCT/US2014/072347, International Filing Date Dec. 24, 2014, dated Jun. 8, 2015, 12 pages.
Price et al.; "The Prospect of Using Cyanobacterial Bicarbonate Transporters to Improve Leaf Photosynthesis in C3 Crop Plants"; Plant Physiology, vol. 155 (1), Jan. 2011, pp. 20-26.
Written Opinion for International Application No. PCT/US2014/072347, International Filing Date Dec. 24, 2014, dated Jun. 8, 2015, 6 pages.
Lieman-Hurwitz, Judy et al., "Enhanced photosynthesis and growth of transgenic plants that express ictB, a gene involved in HCO3-accumulation in cyanobacteria", Plant Biotechnology Journal (2003) 1, pp. 43-50.
Price, G. Dean, et al. "The cyanobacterial CCM as a source of genes for improving photosynthetic CO2 fixation in crop species", Journal of Experimental Botany, vol. 64, No. 3, pp. 753-768, 2013.
Spalding, Martin H., "Microalgal carbon-dioxide-concentrating mechanisms: Chlamydomonas inorganic carbon transporters", Journal of Experimental Botany, vol. 9, No. 7, pp. 1463-1473, 2008.

* cited by examiner

*Primary Examiner* — Russell Kallis
(74) *Attorney, Agent, or Firm* — Cantor Colburn LLP

(57) ABSTRACT

A transgenic plant having enhanced photosynthesis is disclosed. The transgenic plant is transformed with a transgenic polynucleotide encoding a heterologous bicarbonate transporter. The bicarbonate transporter can be from an algae or a cyanobacterial species. The transgenic polynucleotide comprises a nucleic acid sequence encoding the bicarbonate transporter under the control of a functional plant promoter and optionally includes a chloroplast envelope targeting peptide heterologous to the bicarbonate transporter. Methods of making the transgenic plant and transgenic polynucleotide are disclosed.

10 Claims, 15 Drawing Sheets

Specification includes a Sequence Listing.

T: Total extract
P: Membrane Fraction
S: Soluble Fraction

* indicate significance at P=0.05: t-Test: Two-Sample Assuming Unequal Variances

PLANTS WITH ENHANCED PHOTOSYNTHESIS AND METHODS OF MANUFACTURE THEREOF

CROSS-REFERENCE TO RELATED APPLICATIONS

This application is a National Stage application of PCT/US2014/072347, filed Dec. 24, 2014, which claims priority to U.S. application No. 61/922,141 filed Dec. 31, 2013, the disclosure of each is incorporated herein by reference in its entirety.

STATEMENT OF GOVERNMENT SUPPORT

This invention was made in part with government support from the United States Department of Energy. The government has certain rights in this invention.

SEQUENCE LISTING

A Sequence Listing, incorporated herein by reference, is submitted in electronic form as an ASCII text file, created Dec. 30, 2013, updated with priority information on Dec. 23, 2014, and named "UMA0050PCT_sequence ST25".

BACKGROUND

The present disclosure relates to methods of using bicarbonate transporters to enhance photosynthesis in plants to enhance the yield of desirable crop traits including biomass yield, seed yield, oil content in seed, starch content, or sucrose content. In addition these modifications can result in increased drought tolerance.

Crop productivity is limited by numerous factors, a major factor being the relative inefficiency of photochemical conversion of light energy to fixed carbon during photosynthesis. A major contributor to this inefficiency is the dual specificity of the enzyme, ribulose-1,5-bisphosphate carboxylase/oxygenase (rubisco) to fix CO2 via a productive photosynthetic pathway and to fix O2 in a non-productive photorespiratory pathway (Whitney S M, Houtz R L, & Alonso H (2011) Advancing our understanding and capacity to engineer nature's CO2-sequestering enzyme, Rubisco. *Plant Physiol* 155(1):27-35.).

The evolution of C4 and CAM metabolism in plants demonstrates that increasing the ratio of productive carboxylase activity to non-productive oxygenase activity by concentrating CO2 at rubisco (i.e. by minimizing photorespiration) dramatically increases the environmental range and biomass yields of plant species up to 50% (Peterhansel C (2011) Best practice procedures for the establishment of a C4 cycle in transgenic C3 plants. *J Exp Bot* 62(9):3011-3019.). Unfortunately, these complex metabolic strategies are not easily transferred into the more prevalent C3 crop species because they rely on elaborate anatomical structures (e.g. Kranz anatomy in C4 metabolism) and the biogenesis of distinct, cell-specific chloroplast types (Peterhansel 2011). An alternative strategy for increasing photosynthetic efficiency has been on using mutagenesis strategies to increase the ratio of carboxylase/oxygenase activity of rubisco in crop species. Unfortunately, altering the enzymatic properties of rubisco to achieve these aims has been challenging (Taniguchi Y, et al. (2008) Overproduction of C4 photosynthetic enzymes in transgenic rice plants: an approach to introduce the C4-like photosynthetic pathway into rice. *J Exp Bot* 59(7):1799-1809, Hibberd J M & Covshoff S (2010) The regulation of gene expression required for C4 photosynthesis. *Annu Rev Plant Biol* 61:181-207.).

Liquid transportation fuels based on plant seed oils (e.g. biodiesel and green diesel) have tremendous potential as environmentally, economically and technologically feasible alternatives to petroleum-derived fuels. Plant seed oils have distinct advantages over the current use of ethanol derived from corn or sugar cane as a fuel source. Plant oils can be directly converted to fuels with existing technologies, and therefore could replace a significant proportion of the petroleum-based fuels within a decade. Biofuels derived from seed oils are minimally carbon neutral. The biomass consumed as fuel is replaced yearly with a crop consisting of an equivalence of fixed $CO_2$, and emissions from biofuels are cleaner than diesel because of the low sulfur and nitrogen content. A variety of oilseed crops are a mainstay of U.S. agriculture, thus increased cultivation of these crops is largely compatible with existing agricultural practices.

Bio-oil based biofuels in the U.S. currently represent a relatively small portion of the renewable energy market, constituting 5.1% of the highway diesel market in 2001 and projected to reach only 6.8% in 2015 (Tyson T K, Bozell J, Wallace R, Petersen E, & Moens L (2004) Biomass oil analysis: research needs and recommendations, National Renewable Energy Laboratory Technical Report, NREL/TP-510-34796). Current production in the U.S. relies on crop species that have been bred by conventional means for food oil production (e.g. soybean, sunflower and rapeseed), and consequently, fuels, such as biodiesel, are generated primarily from the waste products of the food industry (Tyson et al. 2004). As a consequence, the yields of oils for conversion to biofuels are relatively low. Increased diversion of seed oils from food crops directly into fuel production would directly compete with food oil production, thereby having negative consequences on food oil prices and availability. A second limitation to increased bio-oil production is the relatively low productivity of oil-crop species (soybean or rapeseed) compared to other commodity crops that are used for ethanol production (e.g. corn or sugarcane) (Johnston M, Foley J A, Holloway T, Kucharik C, & Monfreda C (2009) Resetting global expectations from agricultural biofuels. *Environ Res Lett* 4(1)). Consequently, a significant increase in bio-oil based fuels will require the development of highly productive, dedicated oilseed crops with low agronomic requirements.

Thus, there is a need for transgenic plants with enhanced photosynthesis and/or crop yield, and methods, and compositions for use therein, that enhance photosynthesis and crop yield in plants.

BRIEF SUMMARY

Disclosed herein are transgenic plants having enhance photosynthesis compared to wild type plants In an embodiment, the transgenic plant comprises a heterologous bicarbonate transporter, wherein the transgenic plant has a $CO_2$ assimilation rate at least 5% higher than a wild type plant of the same species not comprising the heterologous bicarbonate transporter.

In an embodiment, the transgenic plant comprises a heterologous bicarbonate transporter wherein the transgenic plant has a reduced transpiration rate at least 5% lower than a wild type plant of the same species not comprising the heterologous bicarbonate transporter.

In an embodiment, the transgenic plant is transformed with a recombinant DNA construct comprising a plant-expressible transcription regulatory sequence operatively linked to a polynucleotide encoding a heterologous bicarbonate transporter.

Also disclosed herein are methods and compositions for enhancing photosynthesis in plants.

In an embodiment, a recombinant polynucleotide comprises a nucleic acid sequence encoding a heterologous bicarbonate transporter operatively linked to a plant-expressible transcription regulatory sequence, wherein optionally the nucleic acid sequence encoding the bicarbonate transporter is further operatively linked to a nucleic acid sequence encoding a chloroplast envelope targeting peptide.

In an embodiment, a method of producing a transformed plant having enhanced photosynthesis comprises transforming a plant cell with the disclosed recombinant polynucleotide; growing a plant from the plant cell until the plant produces seed; and selecting seeds from a plant in which photosynthesis is enhanced in comparison with a corresponding plant that is not expressing the heterologous bicarbonate transporter These and other embodiments, advantages and features of the invention become clear when detailed description and examples are provided in subsequent sections.

BRIEF DESCRIPTION OF THE DRAWINGS

Referring now to the drawings wherein like elements are numbered alike in several FIGURES.

DETAILED DESCRIPTION

Figure 1:
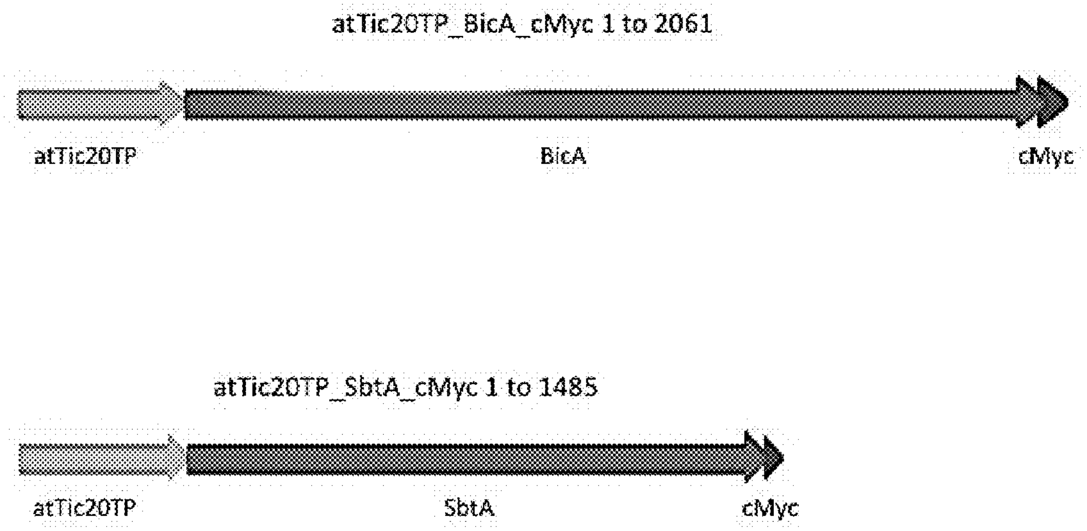
FIG. 1 shows a schematic representation of the atTic20 transit peptide ("atTic20TP"; N-terminal) and cMyc epitope (C-terminal) fusions to the cyanobacterial BicA bicarbonate transporter (upper) or to the cyanobacterial SbtA bicarbonate transporter (lower).

Disclosed herein are transgenic plants comprising a heterologous bicarbonate transporter. It has been unexpectedly discovered that plants engineered to include an exogenous bicarbonate transporter show enhanced carbon photosynthetic capture/fixation rates. Plants expressing the exogenous bicarbonate transporter exhibited higher $CO_2$ assimilation rates relative to wild type plants. The transgenic plants also showed increased water and nitrogen use efficiency and an overall increase in biomass production. The disclosed transgenic plants demonstrate the potential for increasing crop productivity by engineering increased $CO_2$ availability at rubisco.

The transgenic plants have improved ability to fix carbon via photosynthesis as a result of introducing proteins of the $CO_2$ concentrating mechanisms from cyanobacteria and other organisms into the plants. For example, the SbtA protein is a cyanobacterial bicarbonate transporter that increases $CO_2$ availability and adaptation to low $CO_2$. Increasing yield of photosynthesis can thereby increase crop yields. Further, the transgenic plants, in addition to increasing the amount of fixed carbon available for plant growth, can result in an increase nitrogen use efficiency and reduced water demand.

Cyanobacteria and algae have evolved two alternative highly effective carbon concentrating mechanisms (CCMs) to increase carboxylase/oxygenase activity (Price G D, et al. (2013) *J Exp Bot* 64(3):753-768., Meyer M & Griffiths H (2013) *J Exp Bot* 64(3):769-786.). The first uses high affinity bicarbonate membrane transporters to increase cellular $HCO_3^{-1}$. The second strategy sequesters rubisco and carbonic anhydrase within microcompartments called carboxysomes in cyanobacteria and pyrenoids in algae. $HCO_3^-$ is rapidly converted to $CO_2$ by carbonic anhydrases within the microcompartments to significantly increase the concentration of the $CO_2$ at rubisco, thereby increasing carbon assimilation by several orders of magnitude.

Recent studies have modeled the conductance of carbon dioxide within the internal compartments of plant cells. These studies demonstrate that the chloroplast envelope poses a significant resistance barrier to $CO_2$ diffusion within the cell (Evans J R & Von Caemmerer S (1996) *Plant Physiol* 110(2):339-346., Tholen D & Zhu X G (2011) *Plant Physiol* 156(1):90-105.), thereby limiting the rate of carbon fixation by rubisco in the chloroplast stroma (Evans & Von Caemmerer 1996; Price G D, Badger M R, & von Caemmerer S (2011) *Plant Physiol* 155(1):20-26.). The introduction of bicarbonate transporters from microbial and algal CCMs at the chloroplast envelope has the potential to alleviate the diffusion barrier. A number of confirmed and proposed $HCO_3^-$ transporters have been identified in cyanobacteria, including $Na^+$ symporters (BicA and SbtA), ATP-driven (BCT1) and NADPH-driven ($NDH1_4$) uptake systems (Price G D, Badger M R, Woodger F J, & Long B M (2008) *J Exp Bot* 59(7):1441-1461.).

In addition, green algae, such as *Chlamydomonas reinhardtii*, express putative chloroplast $HCO_3^-$ transporters that are induced >1000-fold in response to low $CO_2$ environments. These include the LCIA and the CCP1 and CCP2 (CCP1/2) transporters, which localize to the chloroplast envelope. (Miura K, et al. (2004) *Plant Physiol* 135(3):1595-1607; Chen Z Y, Lavigne L L, Mason C B, & Moroney J V (1997) *Plant Physiol* 114(1):265-273.; Spalding M H & Jeffrey M (1989) *Plant Physiol* 89(1):133-137.) LCIA is a member of the formate/nitrite transporter family of facilitated anion transporters (Mariscal V, et al. (2006) *Protist* 157(4):421-433). Expression of LCIA in *Xenopus oocytes* provided evidence for its function as a low affinity bicarbonate transporter. CCP1 and CCP2 also are proposed to function as bicarbonate transporters. They localize to the chloroplast envelope in *Chlamydomonas* and are related to a family of mitochondrial carrier proteins, including the ADP/ATP translocators. (Moroney J V & Mason C B (1991) *Can J Bot* 69(5):1017-1024; Ramazanov Z, Mason C B, Geraghty A M, Spalding M H, & Moroney J V (1993) *Plant Physiol* 101(4):1195-1199.) CCP1 and CCP2 are 96% identical. Their genes are located within a gene cluster that includes a number of genes encoding additional CCM components (Merchant S S, et al. (2007) *Science* 318(5848):245-250.).

Surprisingly it has been found that expression in transgenic plants of a heterologous bicarbonate transporter, e.g., from cyanobacteria or algae, that localizes to the chloroplast envelope membranes of the plant leads to significant improvements in levels of photosynthesis in the transgenic plant.

Disclosed herein is a transgenic plan having enhanced photosynthesis.

In an embodiment, the transgenic plant comprises a heterologous bicarbonate transporter. In an embodiment, the transgenic plant comprises a recombinant nucleic acid sequence encoding a heterologous bicarbonate transporter operatively linked to a plant-expressible transcription regulatory sequence, wherein the nucleic acid sequence optionally further encodes a chloroplast envelope targeting peptide operatively linked to the heterologous bicarbonate transporter. In an embodiment, the transgenic plant is transformed with a recombinant DNA construct comprising a plant-expressible transcription regulatory sequence operatively linked to a polynucleotide encoding a heterologous bicarbonate transporter and optionally, operatively linked to polynucleotide encoding a chloroplast envelope targeting peptide. In any of these embodiments, the expressed heterologous bicarbonate transporter is localized to a chloroplast envelope membrane.

In an embodiment, the transgenic plant has a $CO_2$ assimilation rate at least 5%, at least 10%, at least 15%, at least 20%, at least 25%, at least 30%, at least 35%, or at least 40% higher than the $CO_2$ assimilation rate of a wild type plant of the same species. Herein a wild type plant means a plant not comprising the heterologous bicarbonate transporter.

In an embodiment, the transgenic plant has a transpiration rate at least 5%, at least 10%, at least 15%, at least 20%, or at least 25%, lower than the transpiration rate of a wild type plant of the same species.

In an embodiment, the transgenic plant has a seed yield at least 5%, at least 10%, at least 15%, at least 20%, at least 30%, at least 40%, or at least 50% higher than the seed yield of a wild type plant of the same species.

In an embodiment, the transgenic plant has a water use efficiency (WUE) at least 5%, at least 10%, at least 15%, at least 20%, at least 25%, at least 30%, at least 35%, or at least 40% higher than the WUE of a wild type plant of the same species.

In an embodiment, the transgenic plant has a nitrogen use efficiency (NUE) at least 5%, at least 10%, at least 15%, at least 20%, at least 25%, at least 30%, at least 35%, or at least 40% higher than the NUE of a wild type plant of the same species.

In an embodiment, the transgenic plant has a maturation rate at least 5%, at least 10%, at least 15%, at least 20%, at least 25%, at least 30%, at least 35%, or at least 40% higher than the maturation rate of a wild type plant of the same species.

Herein, a "bicarbonate transporter" protein is a protein which transports bicarbonate by any transport mechanism. Classes of bicarbonate transporters include anion exchangers and $Na^+/HCO_3^{-1}$ symporters.

In any of the disclosed embodiments, the bicarbonate transporter can be a bicarbonate transporter from a cyanobacterium, e.g., a BicA polypeptide or a SbtA polypeptide, or from an algae, e.g., a CCP1 polypeptide or an LCIA polypeptide. The cyanobacterium can be a *Synechocystis*, e.g., *Synechocystis* PCC6803, or a *Synechococcus*, e.g., *Synechococcus* PCC700. The algae can be a *Chlamydomonas* species, for example a *Chlamydomonas reinhardtii.*

For the purposes of the invention, "plant" refers to all genera and species of higher and lower plants of the Plant Kingdom. The term includes the mature plants, seeds, shoots and seedlings, and parts, propagation material, plant organ tissue, protoplasts, callus and other cultures, for example cell cultures, derived from them, and all other species of groups of plant cells giving functional or structural units. Mature plants refers to plants at any developmental stage beyond the seedling. Seedling refers to a young, immature-plant at an early developmental stage.

"Plant" encompasses all annual and perennial monocotyldedonous or dicotyledonous plants and includes by way of example, but not by limitation, those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Cichorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea and Populus.*

Preferred plants are those from the following plant families: Amaranthaceae, Asteraceae, Brassicaceae, Carophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanaceae, Sterculiaceae, Tetragoniaceae, Theaceae, Umbelliferae.

The invention can particularly be applied advantageously to dicotyledonous plant organisms. Preferred dicotyledonous plants are selected in particular from the dicotyledonous crop plants such as, for example, Asteraceae such as sunflower, *tagetes* or calendula and others; Compositae, especially the genus *Lactuca*, very particularly the species *sativa* (lettuce) and others; Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli) and other cabbages; and the genus *Arabidopsis*, very particularly the species *thaliana*, and cress or canola and others; Cucurbitaceae such as melon, pumpkin/squash or zucchini and others; Leguminosae, particularly the genus *Glycine*, very particularly the species max (soybean), soya, and alfalfa, pea, beans or peanut and others; Rubiaceae, preferably the subclass Lamiidae such as, for example *Coffea arabica* or *Coffea liberica* (coffee bush) and others; Solanaceae, particularly the genus *Lycopersicon*, very particularly the species *esculentum* (tomato), the genus *Solanum*, very particularly the species *tuberosum* (potato) and *melongena* (aubergine) and the genus *Capsicum*, very particularly the genus *annuum* (pepper) and tobacco or paprika and others; Sterculiaceae, preferably the subclass Dilleniidae such as, for example, *Theobroma cacao* (cacao bush) and others; Theaceae, preferably the subclass Dilleniidae such as, for example, *Camellia sinensis* or *Thea sinensis* (tea shrub) and others; Umbelliferae, particularly the genus *Daucus* (very particularly the species *carota* (carrot)) and *Apium* (very particularly the species *graveolens* dulce (celery)) and others; and linseed, cotton, hemp, flax, cucumber, spinach, carrot, sugar beet and the various tree, nut and grapevine species, in particular banana and kiwi fruit.

Also encompassed are ornamental plants, useful or ornamental trees, flowers, cut flowers, shrubs or turf. Plants which may be mentioned by way of example but not by limitation are angiosperms, bryophytes such as, for example, Hepaticae (liver flowers) and Musci (mosses); pteridophytes such as ferns, horsetail and clubmosses; gymnosperms such as conifers, cycads, *ginkgo* and Gnetatae, the families of the Rosaceae such as rose, Ericaceae such as *rhododendron* and azalea, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as *gladioli*, iris, freesia and *crocus*, Compositae such as marigold, Geraniaceae such as geranium, Liliaceae such as dracena, Moraceae such as *ficus*, Araceae such as cheese-plant and many others.

Of particular interest for transformation are plants which are oil crop plants. Oil crop plants are understood as being plants whose oil content is already naturally high and/or which can be used for the industrial production of oils. These plants can have a high oil content and/or else a particular fatty acid composition which is of interest industrially. Preferred plants are those with a lipid content of at least 1% by weight. Oil crops encompass by way of example: *Borago officinalis* (borage); *Camelina* (false flax); *Brassica* species such as *B. campestris, B. napus, B. rapa, B. carinata* (mustard, oilseed rape or turnip rape); *Cannabis sativa* (hemp); *Carthamus tinctorius* (safflower); *Cocos nucifera* (coconut); *Crambe abyssinica* (*crambe*); *Cuphea* species (*Cuphea* species yield fatty acids of medium chain length, in particular for industrial applications); *Elaeis guinensis* (African oil palm); *Elaeis oleifera* (American oil palm); *Glycine max* (soybean); *Gossypium hirsutum* (American cotton); *Gossypium barbadense* (Egyptian cotton); *Gossypium herbaceum* (Asian cotton); *Helianthus annuus* (sunflower); *Linum usitatissimum* (linseed or flax); *Oenothera biennis* (evening primrose); *Olea europaea* (olive); *Oryza sativa* (rice); *Ricinus communis* (castor); *Sesamum indicum* (sesame); *Triticum* species (wheat); *Zea mays* (maize), and various nut species such as, for example, walnut or almond.

*Camelina* species, commonly known as false flax, are native to Mediterranean regions of Europe and Asia and seem to be particularly adapted to cold semiarid climate zones (steppes and prairies). The species *Camelina sativa* was historically cultivated as an oilseed crop to produce vegetable oil and animal feed. It has been introduced to the high plain regions of Canada and parts of the United States as an industrial oilseed crop. As a result of its high oil content (~35%) of its seeds, its frost tolerance, short production cycle (60-90 days), and insect resistance, it is an interesting target for enhancing photosynthesis to improve its potential as a source for production of biofuels.

Also disclosed herein is a recombinant polynucleotide comprising a nucleic acid sequence encoding a bicarbonate transporter operatively linked to a plant-expressible transcription regulatory sequence, wherein optionally the nucleic acid sequence encoding the bicarbonate transporter is further operatively linked to a nucleic acid sequence encoding a chloroplast envelope targeting peptide.

In some embodiments, the nucleic acid sequence encoding the bicarbonate transporter further comprises a sequence encoding an epitope tag to facilitate affinity capture or localization of the expressed bicarbonate transporter. Epitope tagging is a technique in which a known epitope is fused to a recombinant protein by means of genetic engineering. The first commercially available epitope tags were originally designed for protein purification. Additionally, by choosing an epitope for which an antibody is available, the technique makes it possible to detect proteins for which no antibody is available. Additional examples of epitope tags include FLAG, 6×His, glutathione-S-transferase (GST), HA, cMyc, AcV5, or tandem affinity purification epitope tags.

Examples of species from which the bicarbonate transporter gene may be obtained include *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fuse a, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris fo. tertia, Chlorella vulgaris* var. *autotrophica, Chlorella vulgaris* var. *viridis, Chlorella vulgaris* var. *vulgaris, Chlorella vulgaris* var. *vulgaris fo. tertia, Chlorella vulgaris* var. *vulgaris fo. viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Chlamydomonas moewusii, Chlamydomonas reinhardtii, Chlamydomonas* sp. *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis aff. galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricomutum, Phagus, Phormidium, Platymonas* sp., *Pleurochrysis carter ae, Pleuro-*

*chrysis dentate, Pleurochrysis* sp., *Prototheca wickerhamii, Prototheca stagnora, Prototheca portoricensis, Prototheca moriformis, Prototheca zopfii, Pseudo chlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii*, and *Viridiella fridericiana.*

In some embodiments, the bicarbonate transporter is from a cyanobacterium and the nucleic acid sequence encoding the cyanobacterial bicarbonate transporter further comprises a sequence encoding a chloroplast envelope targeting peptide operably linked to the bicarbonate transporter coding sequence. Examples of cyanobacterium include *Synechocystis* species, e.g. *Synechocystis* sp. PCC 6803 and *Synechococcus*, e.g., *Synechococcus* PCC7002. A "chloroplast envelope targeting peptide" refers herein to a peptide sequence that can target a chimeric protein including the peptide to the chloroplast envelope, such as to the chloroplast inner envelope membrane, when the chimeric protein is expressed from the nuclear genome. Examples of suitable chloroplast envelope targeting peptides include transit peptides of precursors of chloroplast envelope membrane proteins, e.g., the transit peptide (aa 1-110) of *Arabidopsis thaliana* atTic20 precursor (Uniprot Q8GZ79, version 52; NP 171986.3); the transit peptide of a chloroplast triose phosphate/phosphate translocator precursor, e.g., the transit peptide (aa 1-72) of the *Pisum sativum* chloroplastic triose phosphate/phosphate translocator precursor (Uniprot P21727, version 73); the transit peptide of *Arabidopsis thaliana* Albino or pale green mutant 1 protein (amino acids 1-51 of GenBank Accession BAB62076.1), or the transit peptides of the *Chlamydomonas reinhardtii* CCP1 precursor or the LCIA precursor.

The cyanobacterial bicarbonate transporter can be a Na+-dependent $HCO_3^-$ transporter, e.g., a BicA polypeptide or a SbtA polypeptide. BicA is widely represented in genomes of oceanic cyanobacteria and belongs to a large family (SulP family) of eukaryotic and prokaryotic transporters presently annotated as sulfate transporters or permeases in many bacteria.

In some embodiments, the bicarbonate transporter is from an algae. The algae can be a *Chlamydomonas* species or any of the algae enumerated in Tables 1 and 2 below. The *Chlamydomonas* species can be, e.g. *Chlamydomonas reinhardtii*. The algal bicarbonate transporter can be a CCP1 polypeptide or a LCIA polypeptide.

In an embodiment, the bicarbonate transporter comprises the SbtA gene of *Synechocystis* PCC6803 (nucleotide sequence, SEQ ID NO:1, Accession No. NC_000911.1 REGION: 1600659 . . . 1601783; GI:16329170); polypeptide sequence SEQ ID NO:2, Accession No. NP_441340.1).

In an embodiment, the bicarbonate transporter comprises the BicA gene of *Synechococcus* PCC7002 (nucleotide sequence, SEQ ID NO:3, Accession No. NC_010475.1 REGION: 2452833 . . . 2454533); polypeptide sequence SEQ ID NO:4, Accession No. YP_001735604.1).

In an embodiment, the bicarbonate transporter comprises the CCP1 gene of *Chlamydomonas reinhardtii* (nucleotide sequence, SEQ ID NO:5, coding sequence of Accession No. XM_001692145.1); polypeptide sequence SEQ ID NO:6, Accession No. XP_001692197.1).

In an embodiment, the bicarbonate transporter comprises the LCIA protein gene of *Chlamydomonas reinhardtii* (nucleotide sequence, SEQ ID NO:7, coding sequence of Accession No. XM_001691161.1); polypeptide sequence SEQ ID NO:8, Accession No. XP_001691213.1).

A bicarbonate transporter includes a bicarbonate transporter homologous to SbtA, BicA, CCP1, or LCIA so long as the bicarbonate transporter has bicarbonate transporter activity. "Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared. Falling within this generic term are the terms "ortholog" meaning a polynucleotide or polypeptide that is the functional equivalent of a polynucleotide or polypeptide in another species, and "paralog" meaning a functionally similar sequence when considered within the same species. Paralogs present in the same species or orthologs of the bicarbonate transporter gene in other species can readily be identified without undue experimentation, by molecular biological techniques well known in the art. As used herein, SbtA, BicA, CCP1, or LCIA refers to SbtA, BicA, CCP1, or LCIA, respectively, as well as their homologs and orthologs.

Known coding sequences and/or protein sequences having significant similarity to *Chlamydomonas reinhardtii* CCP1, *Chlamydomonas reinhardtii* LCIA, *Synechococcus* sp. PCC 7002 BicA, or *Synechocystis* sp. PCC 6803 SbtA which are suitable for practicing the disclosed methods to generate transgenic plants with enhanced photosynthesis are tabulated in Tables 1-4 below. For *Chlamydomonas reinhardtii* CCP1 or *Chlamydomonas reinhardtii* LCIA, these coding sequences and protein sequences were identified by a tBLASTN search of GenBank with an appropriate query sequence, as indicated in Tables 1-2. Only sequences with E values of <E-10 are shown in Tables 1-2. For *Synechococcus* sp. PCC 7002 BicA or *Synechocystis* sp. PCC 6803 SbtA, protein sequences were identified by a BLASTP search of GenBank with an appropriate query sequence, as indicated in Tables 3-4. Only sequences with amino acid sequence identity of ≥60% to *Synechococcus* sp. PCC 7002 BicA or *Synechocystis* sp. PCC 6803 SbtA are shown in Tables 3 and 4, respectively.

TABLE 1

DNA and protein sequences showing significant similarity to *Chlamydomonas reinhardtii* CCP1 determined from a tBLASTN search of Genbank using accession number XM_001692145 for C.r. CCP1 protein.

| Accession Numbers\| Description | E Value |
|---|---|
| *Chlamydomonas reinhardtii* | |
| ref\|XM_001692145.1\| *Chlamydomonas reinhardtii* strain CC-503 | 0 |
| gb\|U75345.1\|CRU75345 *Chlamydomonas reinhardtii* envelope prote . . . | 0 |
| ref\|XM_001692236.1\| *Chlamydomonas reinhardtii* strain CC-503 c . . . | 0 |
| gb\|U75346.1\|CRU75346 *Chlamydomonas reinhardtii* envelope prote . . . | 0 |
| ref\|XM_001691276.1\| *Chlamydomonas reinhardtii* strain CC-503 | 6.00E−29 |

TABLE 1-continued

DNA and protein sequences showing significant similarity to *Chlamydomonas reinhardtii* CCP1 determined from a tBLASTN search of Genbank using accession number XM_001692145 for C.r. CCP1 protein.

| Accession Numbers\| Description | E Value |
|---|---|
| ref\|XM_001703524.1\| *Chlamydomonas reinhardtii* | 2.00E−21 |
| ref\|XM_001696176.1\| *Chlamydomonas reinhardtii* strain CC-503 | 1.00E−13 |
| Other Algae | |
| ref\|XM_002951197.1\| *Volvox carteri* f. *nagariensis* | 0 |
| ref\|XM_005707055.1\| *Galdieria sulphuraria* | 9.00E−44 |
| ref\|XM_002180092.1\| *Phaeodactylum tricornutum* CCAP 1055/1 | 1.00E−36 |
| ref\|XM_005650930.1\| *Coccomyxa subellipsoidea* C-169 | 3.00E−36 |
| ref\|XM_005846489.1\| *Chlorella variabilis* | 8.00E−35 |
| ref\|XM_005715654.1\| *Chondrus crispus* | 3.00E−31 |
| ref\|XM_005852157.1\| *Chlorella variabilis* | 2.00E−30 |
| ref\|XM_005835528.1\| *Guillardia theta* CCMP2712 | 2.00E−29 |
| ref\|XM_001416612.1\| *Ostreococcus lucimarinus* CCE9901 | 5.00E−29 |
| ref\|XM_005648666.1\| *Coccomyxa subellipsoidea* C-169 | 7.00E−29 |
| ref\|XM_005713259.1\| *Chondrus crispus* Putative | 1.00E−28 |
| ref\|XM_002290899.1\| *Thalassiosira pseudonana* CCMP1335 | 5.00E−28 |
| ref\|XM_003062315.1\| *Micromonas pusilla* CCMP1545 | 9.00E−28 |
| ref\|XM_002501234.1\| *Micromonas* sp. RCC299 | 2.00E−27 |
| ref\|XM_003078113.1\| *Ostreococcus tauri* | 2.00E−27 |
| ref\|XM_002287074.1\| *Thalassiosira pseudonana* CCMP1335 | 3.00E−27 |
| gb\|CP000583.1\| *Ostreococcus lucimarinus* CCE9901 | 5.00E−27 |
| gb\|CP001325.1\| *Micromonas* sp. RCC299 | 8.00E−27 |
| ref\|XM_005761119.1\| *Emiliania huxleyi* CCMP1516 | 2.00E−26 |
| ref\|XM_005770260.1\| *Emiliania huxleyi* CCMP1516 | 2.00E−26 |
| ref\|XM_005782860.1\| *Emiliania huxleyi* CCMP1516 | 4.00E−26 |
| ref\|XM_005780967.1\| *Emiliania huxleyi* CCMP1516 | 9.00E−26 |
| ref\|XM_002505238.1\| *Micromonas* sp. RCC299. | 3.00E−24 |
| gb\|GU554694.1\| uncultured dinoflagellate | 1.00E−23 |
| ref\|XM_005645863.1\| *Coccomyxa subellipsoidea* C-169 | 1.00E−23 |
| gb\|CP001330.1\| *Micromonas* sp. RCC299 | 3.00E−23 |
| ref\|XM_005821628.1\| *Guillardia theta* CCMP2712 | 1.00E−22 |
| ref\|XM_005839321.1\| *Guillardia theta* CCMP2712 | 1.00E−22 |
| ref\|XM_002181059.1\| *Phaeodactylum tricornutum* CCAP 1055/1 | 3.00E−22 |
| ref\|XM_005843001.1\| *Chlorella variabilis* | 3.00E−22 |
| ref\|XM_005820122.1\| *Guillardia theta* CCMP2712 | 4.00E−22 |
| ref\|XM_002507318.1\| *Micromonas* sp. RCC299 | 4.00E−21 |
| ref\|XM_002186292.1\| *Phaeodactylum tricornutum* CCAP 1055/1 | 1.00E−20 |
| ref\|XM_005855105.1\| *Nannochloropsis gaditana* CCMP526 | 5.00E−20 |
| ref\|XM_005650392.1\| *Coccomyxa subellipsoidea* C-169 | 2.00E−19 |
| gb\|HQ199284.1\| *Karlodinium micrum* | 2.00E−19 |
| ref\|XM_002292980.1\| *Thalassiosira pseudonana* CCMP1335. | 2.00E−18 |
| ref\|XM_002178459.1\| *Phaeodactylum tricornutum* CCAP 1055/1 | 1.00E−17 |
| ref\|XM_005834754.1\| *Guillardia theta* CCMP2712 | 3.00E−17 |
| ref\|XM_002288920.1\| *Thalassiosira pseudonana* CCMP1335 | 3.00E−17 |
| ref\|XM_001421091.1\| *Ostreococcus lucimarinus* CCE9901 | 3.00E−17 |
| ref\|XM_001422789.1\| *Ostreococcus lucimarinus* CCE9901 | 3.00E−17 |
| ref\|XM_002292865.1\| *Thalassiosira pseudonana* CCMP1335 | 4.00E−17 |
| gb\|CP000601.1\| *Ostreococcus lucimarinus* CCE9901 | 2.00E−16 |
| gb\|CP000593.1\| *Ostreococcus lucimarinus* CCE9901 | 2.00E−16 |
| ref\|XM_003075149.1\| *Ostreococcus tauri* | 6.00E−16 |
| ref\|XM_001416252.1\| *Ostreococcus lucimarinus* CCE9901 | 1.00E−15 |
| ref\|XM_002295407.1\| *Thalassiosira pseudonana* CCMP1335 | 1.00E−15 |
| ref\|XM_002292854.1\| *Thalassiosira pseudonana* CCMP1335 | 1.00E−15 |
| ref\|XM_002179955.1\| *Phaeodactylum tricornutum* CCAP 1055/1 | 2.00E−15 |
| gb\|CP000582.1\| *Ostreococcus lucimarinus* CCE9901 | 2.00E−15 |
| ref\|XM_005705684.1\| *Galdieria sulphuraria* | 6.00E−15 |
| ref\|XM_002502386.1\| *Micromonas* sp. RCC299 | 7.00E−15 |
| ref\|XM_005538709.1\| *Cyanidioschyzon merolae* strain 10D | 7.00E−15 |
| ref\|XM_003060288.1\| *Micromonas pusilla* CCMP1545 | 1.00E−14 |
| ref\|XM_002287700.1\| *Thalassiosira pseudonana* CCMP1335 | 1.00E−14 |
| ref\|XM_005706410.1\| *Galdieria sulphuraria* | 1.00E−14 |
| ref\|XM_002501612.1\| *Micromonas* sp. RCC299 | 1.00E−14 |
| ref\|XM_002957505.1\| *Volvox carteri* f. *nagariensis* | 1.00E−14 |
| ref\|XM_001416306.1\| *Ostreococcus lucimarinus* CCE9901 | 2.00E−14 |
| ref\|XM_005705667.1\| *Galdieria sulphuraria* | 2.00E−14 |
| ref\|XM_002952252.1\| *Volvox carteri* f. *nagariensis* | 2.00E−14 |
| ref\|XM_002184902.1\| *Phaeodactylum tricornutum* CCAP 1055/1 | 3.00E−14 |
| ref\|XM_003082660.1\| *Ostreococcus tauri* | 3.00E−14 |
| dbj\|AP006501.2\| *Cyanidioschyzon merolae* strain 10D | 4.00E−14 |
| gb\|CP001326.1\| *Micromonas* sp. RCC299 | 6.00E−14 |
| ref\|XM_005833520.1\| *Guillardia theta* CCMP2712 hypothetical | 7.00E−14 |
| ref\|XM_002181779.1\| *Phaeodactylum tricornutum* CCAP 1055/1 | 9.00E−14 |
| ref\|XM_002183511.1\| *Phaeodactylum tricornutum* CCAP 1055/1 | 9.00E−14 |
| ref\|XM_005645399.1\| *Coccomyxa subellipsoidea* C-169 | 2.00E−13 |

TABLE 1-continued

DNA and protein sequences showing significant similarity to *Chlamydomonas reinhardtii* CCP1 determined from a tBLASTN search of Genbank using accession number XM_001692145 for C.r. CCP1 protein.

| Accession Numbers\| Description | E Value |
|---|---|
| ref\|XM_005645636.1\| *Coccomyxa subellipsoidea* C-169 | 2.00E−13 |
| ref\|XM_005712871.1\| *Chondrus crispus* | 3.00E−13 |
| ref\|XM_002294126.1\| *Thalassiosira pseudonana* CCMP1335 | 3.00E−13 |
| ref\|XM_002945774.1\| *Volvox carteri* f. *nagariensis* | 4.00E−13 |
| ref\|XM_001696541.1\| *Chlamydomonas reinhardtii* | 4.00E−13 |
| ref\|XM_005830601.1\| *Guillardia theta* CCMP2712 | 5.00E−13 |
| ref\|XM_002286219.1\| *Thalassiosira pseudonana* CCMP1335 | 5.00E−13 |
| ref\|XM_005704882.1\| *Galdieria sulphuraria* | 6.00E−13 |
| ref\|XM_005703227.1\| *Galdieria sulphuraria* | 7.00E−13 |
| ref\|XM_005851446.1\| *Chlorella variabilis* | 9.00E−13 |
| emb\|FO082276.1\| *Bathycoccus prasinos* | 2.00E−12 |
| ref\|XM_003057854.1\| *Micromonas pusilla* CCMP1545 | 2.00E−12 |
| ref\|XM_005829724.1\| *Guillardia theta* CCMP2712 | 2.00E−12 |
| ref\|XM_001692202.1\| *Chlamydomonas reinhardtii* strain CC-503 | 3.00E−12 |
| ref\|XM_002952755.1\| *Volvox carteri* f. *nagariensis* | 4.00E−12 |
| ref\|XM_002290151.1\| *Thalassiosira pseudonana* CCMP1335 | 4.00E−12 |
| ref\|XM_003080464.1\| *Ostreococcus tauri* | 4.00E−12 |
| ref\|XM_001698874.1\| *Chlamydomonas reinhardtii* | 5.00E−12 |
| ref\|XM_005702733.1\| *Galdieria sulphuraria* | 5.00E−12 |
| ref\|XM_005649150.1\| *Coccomyxa subellipsoidea* C-169 | 7.00E−12 |
| ref\|XM_005702730.1\| *Galdieria sulphuraria* | 7.00E−12 |
| ref\|XM_001418979.1\| *Ostreococcus lucimarinus* CCE9901 | 9.00E−12 |
| ref\|XM_005836140.1\| *Guillardia theta* CCMP2712 | 9.00E−12 |
| Diatoms | |
| ref\|XM_002180092.1\| *Phaeodactylum tricornutum* CCAP 1055/1 | 1.00E−37 |
| ref\|XM_002290899.1\| *Thalassiosira pseudonana* CCMP1335 | 5.00E−29 |
| ref\|XM_002287074.1\| *Thalassiosira pseudonana* CCMP1335 | 3.00E−28 |
| ref\|XM_002181059.1\| *Phaeodactylum tricornutum* CCAP 1055/1 | 3.00E−23 |
| ref\|XM_002186292.1\| *Phaeodactylum tricornutum* CCAP 1055/1 | 1.00E−21 |
| ref\|XM_002292980.1\| *Thalassiosira pseudonana* CCMP1335 | 2.00E−19 |
| ref\|XM_002178459.1\| *Phaeodactylum tricornutum* CCAP 1055/1 | 2.00E−18 |
| ref\|XM_002288920.1\| *Thalassiosira pseudonana* CCMP1335 | 3.00E−18 |
| ref\|XM_002292865.1\| *Thalassiosira pseudonana* CCMP1335 | 4.00E−18 |
| ref\|XM_002295407.1\| *Thalassiosira pseudonana* CCMP1335 | 1.00E−16 |
| ref\|XM_002292854.1\| *Thalassiosira pseudonana* CCMP1335 | 1.00E−16 |
| ref\|XM_002179955.1\| *Phaeodactylum tricornutum* CCAP 1055/1 | 2.00E−16 |
| ref\|XM_002287700.1\| *Thalassiosira pseudonana* CCMP1335 | 1.00E−15 |
| ref\|XM_002184902.1\| *Phaeodactylum tricornutum* CCAP 1055/1 | 3.00E−15 |
| ref\|XM_002179954.1\| *Phaeodactylum tricornutum* CCAP 1055/1 | 3.00E−15 |
| ref\|XM_002181779.1\| *Phaeodactylum tricornutum* CCAP 1055/1 | 9.00E−15 |
| ref\|XM_002183511.1\| *Phaeodactylum tricornutum* CCAP 1055/1 | 1.00E−14 |
| ref\|XM_002294126.1\| *Thalassiosira pseudonana* CCMP1335 | 3.00E−14 |
| ref\|XM_002286219.1\| *Thalassiosira pseudonana* CCMP1335 | 5.00E−14 |
| ref\|XM_002184448.1\| *Phaeodactylum tricornutum* CCAP 1055/1 | 1.00E−13 |
| gb\|AC151917.1\| *Phaeodactylum tricornutum* clone JGIAHOK-13P1, | 3.00E−13 |
| ref\|XM_002290151.1\| *Thalassiosira pseudonana* CCMP1335 | 4.00E−13 |
| ref\|XM_002185993.1\| *Phaeodactylum tricornutum* CCAP 1055/1 | 1.00E−12 |
| gb\|CP001142.1\| *Phaeodactylum tricornutum* CCAP 1055/1 | 1.00E−12 |
| ref\|XM_002287767.1\| *Thalassiosira pseudonana* CCMP1335 | 1.00E−12 |
| ref\|XM_002288448.1\| *Thalassiosira pseudonana* CCMP1335 | 6.00E−12 |
| ref\|XM_002185105.1\| *Phaeodactylum tricornutum* CCAP 1055/1 | 3.00E−11 |
| ref\|XM_002289746.1\| *Thalassiosira pseudonana* CCMP1335 | 6.00E−11 |
| ref\|XM_002287949.1\| *Thalassiosira pseudonana* CCMP1335 | 8.00E−11 |
| ref\|XM_002292598.1\| *Thalassiosira pseudonana* CCMP1335 | 2.00E−10 |
| ref\|XM_002181188.1\| *Phaeodactylum tricornutum* CCAP 1055/1 | 3.00E−10 |
| ref\|XM_002185854.1\| *Phaeodactylum tricornutum* CCAP 1055/1 | 6.00E−10 |

TABLE 2

DNA and protein sequences showing significant similarity to *Chlamydomonas reinhardtii* LCIA determine from a tBLASTN search of Genbank using accession numbers XM_001691161 for C.r. LCIA protein.

| Accession Numbers\| Description | E Value |
|---|---|
| *Chlamydomonas reinhardtii* | |
| gb\|AY612639.1\| *Chlamydomonas reinhardtii* NAR1.2 mRNA | 0 |

TABLE 2-continued

DNA and protein sequences showing significant similarity to *Chlamydomonas reinhardtii* LCIA determine from a tBLASTN search of Genbank using accession numbers XM_001691161 for C.r. LCIA protein.

| Accession Numbers\| Description | E Value |
|---|---|
| ref\|XM_001691161.1\| *Chlamydomonas reinhardtii* strain CC-503 | 0 |
| dbj\|AB168092.1\| *Chlamydomonas reinhardtii* LciA mRNA | 0 |
| ref\|XM_001694015.1\| *Chlamydomonas reinhardtii* | 3.00E−75 |

TABLE 2-continued

DNA and protein sequences showing significant similarity to *Chlamydomonas reinhardtii* LCIA determine from a tBLASTN search of Genbank using accession numbers XM_001691161 for C.r. LCIA protein.

| Accession Numbers\| Description | E Value |
|---|---|
| gb\|AY612641.1\| *Chlamydomonas reinhardtii* | 3.00E−73 |
| ref\|XM_001696646.1\| *Chlamydomonas reinhardtii* strain CC-503 | 1.00E−66 |
| gb\|AF149737.1\|AF149737 *Chlamydomonas reinhardtii* | 1.00E−66 |
| ref\|XM_001701226.1\| *Chlamydomonas reinhardtii* strain CC-503 | 4.00E−39 |
| gb\|AY612643.1\| *Chlamydomonas reinhardtii* NAR1.3 mRNA | 4.00E−39 |
| ref\|XM_001700096.1\| *Chlamydomonas reinhardtii* | 2.00E−38 |
| gb\|AY612640.1\| *Chlamydomonas reinhardtii* NAR1.4 mRNA | 2.00E−38 |
| gb\|AY612642.1\| *Chlamydomonas reinhardtii* NAR1.6 mRNA | 8.00E−33 |
| gb\|AF149738.1\|AF149738 *Chlamydomonas reinhardtii* | 2.00E−11 |
| Other Algae | |
| ref\|XM_002951461.1\| *Volvox carteri* f. *nagariensis* | 3.00E−158 |
| ref\|XM_002955738.1\| *Volvox carteri* f. *nagariensis* | 2.00E−76 |
| ref\|XM_005642784.1\| *Coccomyxa subellipsoidea* C-169 | 5.00E−76 |
| ref\|XM_002288264.1\| *Thalassiosira pseudonana* CCMP1335 | 9.00E−67 |
| ref\|XM_005778866.1\| *Emiliania huxleyi* CCMP1516 | 2.00E−66 |
| ref\|XM_005712240.1\| *Chondrus crispus* | 2.00E−63 |
| ref\|XM_005850303.1\| *Chlorella variabilis* | 5.00E−63 |
| ref\|XM_005651463.1\| *Coccomyxa subellipsoidea* C-169 | 2.00E−61 |
| ref\|XM_002180944.1\| *Phaeodactylum tricornutum* CCAP 1055/1 | 5.00E−60 |
| emb\|FO082277.1\| *Bathycoccus prasinos genomic* | 4.00E−57 |
| ref\|XM_002955169.1\| *Volvox carteri* f. *nagariensis* | 2.00E−56 |
| ref\|XM_001419882.1\| *Ostreococcus lucimarinus* CCE9901 | 9.00E−56 |
| ref\|XM_002507067.1\| *Micromonas* sp. RCC299 | 1.00E−55 |
| ref\|XM_005756409.1\| *Emiliania huxleyi* CCMP1516 | 2.00E−55 |
| ref\|XM_003058273.1\| *Micromonas pusilla* CCMP1545 | 1.00E−53 |
| gb\|CP000590.1\| *Ostreococcus lucimarinus* CCE9901 | 4.00E−52 |
| ref\|XM_002507466.1\| *Micromonas* sp. RCC299. | 2.00E−49 |
| gb\|CP001574.1\| *Micromonas* sp. RCC299. | 5.00E−49 |
| ref\|XM_002952265.1\| *Volvox carteri* f. *nagariensis* | 3.00E−44 |
| gb\|DQ884413.1\| *Prorocentrum minimum* | 1.00E−42 |
| ref\|XM_003081477.1\| *Ostreococcus tauri* Nar | 2.00E−42 |
| ref\|XM_005846147.1\| *Chlorella variabilis* | 2.00E−42 |
| emb\|FR694650.1\| *Polytomella* sp. *Pringsheim* 198.80 mRNA | 3.00E−39 |
| ref\|XM_002950368.1\| *Volvox carteri* f. *nagariensis* | 6.00E−38 |
| ref\|XM_005783173.1\| *Emiliania huxleyi* CCMP1516 | 4.00E−36 |
| ref\|XM_001689380.1\| *Chlamydomonas reinhardtii* | 6.00E−33 |
| gb\|FJ600174.1\| *Prorocentrum minimum* clone Pmi_cDNA83. | 2.00E−32 |
| ref\|XM_005822517.1\| *Guillardia theta* CCMP2712 | 8.00E−32 |
| ref\|XM_005845893.1\| *Chlorella variabilis* | 4.00E−27 |
| ref\|XM_005784702.1\| *Emiliania huxleyi* CCMP1516 | 7.00E−22 |
| gb\|DQ228185.1\| *Prototheca wickerhamii* strain SAG 263-11 | 2.00E−21 |
| gb\|KC940652.1\| *Symbiodinium kawagutii* strain CCMP2468. | 1.00E−18 |
| gb\|AY559036.1\| *Euglena gracilis* FocA-like mRNA | 6.00E−18 |
| gb\|KC944854.1\| *Symbiodinium kawagutii* strain CCMP2468 | 1.00E−15 |
| ref\|XM_005774305.1\| *Emiliania huxleyi* CCMP1516 | 8.00E−14 |
| ref\|XM_005782564.1\| *Emiliania huxleyi* CCMP1516 | 9.00E−14 |
| gb\|KC938148.1\| *Symbiodinium kawagutii* strain CCMP2468 | 2.00E−13 |
| Diatoms | |
| ref\|XM_002288264.1\| *Thalassiosira pseudonana* CCMP1335 | 1.00E−68 |
| ref\|XM_002180944.1\| *Phaeodactylum tricornutum* CCAP 1055/1 | 7.00E−62 |

TABLE 3

DNA and protein sequences showing significant similarity to BicA from *Synechococcus* sp. PCC 7002 determined from a BLASTP search of Genbank using accession numbers YP_001735604.1 for BicA protein. Only sequences with amino acid sequence identity of ≥60% to BicA are shown.

| Accession Numbers | Description | Percent Identity |
|---|---|---|
| gi\|170078966\|YP_001735604.1 | bicarbonate transporter, BicA [*Synechococcus* sp. PCC 7002] | 100% |
| gi\|493563527\|WP_006516911.1 | sulfate permeas-like transporter, MFS superfamily [*Leptolyngbya* sp. PCC 7375] | 78% |
| gi\|427722972\|YP_007070249.1 | sulfate transporter [*Leptolyngbya* sp. PCC 7376] | 78% |
| gi\|515897157\|WP_017327740.1 | bicarbonate transporter [*Synechococcus* sp. PCC 7336] | 78% |
| gi\|16331714\|NP_442442.1 | bicarbonate transporter [*Synechocystis* sp. PCC 6803] | 78% |
| gi\|553737472\|WP_023071703.1 | sulfate transporter [*Leptolyngbya* sp. Heron Island J] | 78% |
| gi\|495593045\|WP_008317624.1 | sulfate permease-like transporter, MFS superfamily [*Leptolyngbya* sp. PCC 6406] | 76% |
| gi\|493500254\|WP_006454776.1 | putative permease subfamily, putative [*Synechococcus* sp. PCC 7335] | 75% |
| gi\|498164607\|WP_010478763.1 | bicarbonate transporter [*Acaryochloris* sp. CCMEE 5410] | 75% |
| gi\|550277791\|WP_022604290.1 | sulfate permease [*Rubidibacter lacunae*] | 74% |
| gi\|516255556\|WP_017659519.1 | hypothetical protein [*Geitlerinema* sp. PCC 7105] | 73% |
| gi\|518333320\|WP_019503527.1 | bicarbonate transporter [*Pleurocapsa* sp. PCC 7319] | 72% |
| gi\|427736702\|YP_007056246.1 | sulfate permease [*Rivularia* sp. PCC 7116] | 72% |
| gi\|493033976\|WP_006102720.1 | putative permease subfamily, putative [*Coleofasciculus chthonoplastes*] | 71% |
| gi\|495457973\|WP_008182665.1 | sulfate permease, MFS superfamily transporter [*Moorea producens*] | 71% |
| gi\|428768926\|YP_007160716.1 | sulfate transporter [*Cyanobacterium aponinum* PCC 10605] | 70% |
| gi\|148243262\|YP_001228419.1 | MFS superfamily sulfate permease [*Synechococcus* sp. RCC307] | 70% |
| gi\|428773621\|YP_007165409.1 | sulfate transporter [*Cyanobacterium stanieri* PCC 7202] | 70% |
| gi\|550277639\|WP_022604143.1 | sulfate permease [*Rubidibacter lacunae*] | 70% |
| gi\|493166065\|WP_006171102.1 | low affinity sulfate transporter [*Synechococcus* sp. WH 5701] | 70% |
| gi\|493558939\|WP_006512391.1 | sulfate permease-like transporter, MFS superfamily [*Xenococcus* sp. PCC 7305] | 70% |
| gi\|515863586\|WP_017294214.1 | hypothetical protein [*Geminocystis herdmanii*] | 70% |

TABLE 3-continued

DNA and protein sequences showing significant similarity to BicA from *Synechococcus* sp. PCC 7002 determined from a BLASTP search of Genbank using accession numbers YP_001735604.1 for BicA protein. Only sequences with amino acid sequence identity of ≥60% to BicA are shown.

| Accession Numbers | Description | Percent Identity |
|---|---|---|
| gi\|428775615\|YP_007167402.1 | sulfate transporter [*Halothece* sp. PCC 7418] | 70% |
| gi\|498156944\|WP_010471100.1 | sulfate transporter [*Acaryochloris* sp. CCMEE 5410] | 69% |
| gi\|428205959\|YP_007090312.1 | sulfate transporter [*Chroococcidiopsis thermalis* PCC 7203] | 69% |
| gi\|497231087\|WP_009545349.1 | sulfate transporter [*Cyanothece* sp. ATCC 51472] | 69% |
| gi\|172038396\|YP_001804897.1 | putative bicarbonate transporter [*Cyanothece* sp. ATCC 51142] | 69% |
| gi\|493577440\|WP_006530556.1 | sulfate permease-like transporter, MFS superfamily [*Gloeocapsa* sp. PCC 73106] | 69% |
| gi\|493674092\|WP_006624412.1 | sulfate transporter [*Arthrospira*] | 69% |
| gi\|158336334\|YP_001517508.1 | sulfate transporter [*Acaryochloris marina* MBIC11017] | 69% |
| gi\|479127406\|YP_005067366.1 | putative transporter [*Arthrospira platensis* NIES-39] | 69% |
| gi\|494162279\|WP_007102014.1 | putative sulfate transporter [*Synechococcus* sp. RS9917] | 69% |
| gi\|428780552\|YP_007172338.1 | sulfate permease [*Dactylococcopsis salina* PCC 8305] | 68% |
| gi\|517211961\|WP_018400779.1 | hypothetical protein [*filamentous cyanobacterium* ESFC-1] | 68% |
| gi\|493667004\|WP_006617346.1 | sulfate transporter [*Arthrospira platensis*] | 68% |
| gi\|495548131\|WP_008272710.1 | low affinity sulfate transporter [*Cyanothece* sp. CCY0110] | 68% |
| gi\|497992634\|WP_010306790.1 | MFS superfamily sulfate permease [*Synechococcus* sp. CB0101] | 68% |
| gi\|493966805\|WP_006910111.1 | bicarbonate transporter [*Cyanobium* sp. PCC 7001] | 68% |
| gi\|113474840\|YP_720901.1 | sulfate transporter [*Trichodesmium erythraeum* IMS101] | 67% |
| gi\|434398075\|YP_007132079.1 | sulfate transporter [*Stanieria cyanosphaera* PCC 7437] | 67% |
| gi\|498002398\|WP_010316554.1 | MFS superfamily sulfate permease [*Synechococcus* sp. CB0205] | 67% |
| gi\|515882020\|WP_017312603.1 | bicarbonate transporter [*Fischerella* sp. PCC 9339] | 67% |
| gi\|515348246\|WP_016862598.1 | bicarbonate transporter [*Fischerella muscicola*] | 67% |
| gi\|428201884\|YP_007080473.1 | sulfate permease [*Pleurocapsa* sp. PCC 7327] | 67% |
| gi\|516317247\|WP_017713941.1 | hypothetical protein [*Prochlorothrix hollandica*] | 67% |
| gi\|427713992\|YP_007062616.1 | sulfate permease [*Synechococcus* sp. PCC 6312] | 67% |
| gi\|427729101\|YP_007075338.1 | sulfate permease [*Nostoc* sp. PCC 7524] | 66% |
| gi\|515367638\|WP_016870411.1 | bicarbonate transporter [*Fischerella muscicola*] | 66% |
| gi\|516350484\|WP_017740517.1 | bicarbonate transporter [*Scytonema hofmanni*] | 66% |
| gi\|488869995\|WP_002782234.1 | Similar to Q8YXB1_ANASP Sulfate permease family protein [*Microcystis aeruginosa*] | 66% |
| gi\|488873370\|WP_002785595.1 | Similar to Q8YXB1_ANASP Sulfate permease family protein [*Microcystis aeruginosa*] | 66% |
| gi\|553829773\|AGY61228.1 | BicA [*Microcystis aeruginosa* UvA V145] | 66% |
| gi\|428219557\|YP_007104022.1 | sulfate transporter [*Pseudanabaena* sp. PCC 7367] | 66% |
| gi\|434393346\|YP_007128293.1 | sulfate transporter [*Gloeocapsa* sp. PCC 7428] | 66% |
| gi\|518320508\|WP_019490715.1 | bicarbonate transporter [*Calothrix* sp. PCC 7103] | 66% |
| gi\|515388472\|WP_016879070.1 | bicarbonate transporter [*Chlorogloeopsis*] | 66% |
| gi\|159029320\|CAO90186.1 | unnamed protein product [*Microcystis aeruginosa* PCC 7806] | 66% |
| gi\|488833686\|WP_002746092.1 | permease family protein [*Microcystis aeruginosa*] | 66% |
| gi\|488885099\|WP_002797324.1 | Similar to Q8YXB1_ANASP Sulfate permease family protein [*Microcystis aeruginosa*] | 66% |
| gi\|488839195\|WP_002751601.1 | Similar to Q8YXB1_ANASP Sulfate permease family protein [*Microcystis aeruginosa*] | 66% |
| gi\|497073523\|WP_009459185.1 | sulfate transporter [*Fischerella*] | 66% |
| gi\|428311670\|YP_007122647.1 | sulfate permease [*Microcoleus* sp. PCC 7113] | 66% |
| gi\|493904216\|WP_006849914.1 | bicarbonate transporter [*Synechococcus* sp. WH 8109] | 66% |
| gi\|78212519\|YP_381298.1 | sulfate transporter [*Synechococcus* sp. CC9605] | 66% |
| gi\|493212811\|WP_006197225.1 | sulfate permease family protein [*Nodularia spumigena*] | 66% |
| gi\|488866692\|WP_002778931.1 | Similar to Q8YXB1_ANASP Sulfate permease family protein [*Microcystis aeruginosa*] | 66% |
| gi\|75812386\|YP_320005.1 | Sulfate transporter/antisigma-factor antagonist STAS [*Anabaena variabilis* ATCC 29413] | 66% |
| gi\|17228799\|NP_485347.1 | sulfate permease [*Nostoc* sp. PCC 7120] | 66% |
| gi\|516350212\|WP_01770245.1 | bicarbonate transporter [*Scytonema hofmanni*] | 66% |
| gi\|515857261\|WP_017287889.1 | bicarbonate transporter [*Leptolyngbya boryana*] | 66% |
| gi\|494597829\|WP_007356083.1 | sulphate transporter [*Oscillatoria*] | 66% |
| gi\|440679776\|YP_007154571.1 | sulfate transporter [*Anabaena cylindrica* PCC 7122] | 65% |
| gi\|78184466\|YP_376901.1 | sulfate transporter [*Synechococcus* sp. CC9902] | 65% |
| gi\|288942453\|YP_003444693.1 | sulfate transporter [*Allochromatium vinosum* DSM 180] | 65% |
| gi\|428214257\|YP_007087401.1 | sulfate permease [*Oscillatoria acuminata* PCC 6304] | 65% |
| gi\|497475876\|WP_009790074.1 | putative sulfate transporter [*Synechococcus* sp. BL107] | 64% |
| gi\|493212889\|WP_006197262.1 | Sulfate transporter/antisigma-factor antagonist STAS [*Nodularia spumigena*] | 64% |
| gi\|493318518\|WP_006275869.1 | Sulfate transporter family protein [*Cylindrospermopsis raciborskii*] | 64% |
| gi\|428215452\|YP_007088596.1 | sulfate permease [*Oscillatoria acuminata* PCC 6304] | 64% |
| gi\|494521879\|WP_007311332.1 | Sulfate permease [*Crocosphaera watsonii*] | 64% |
| gi\|517208820\|WP_018397638.1 | bicarbonate transporter [*filamentous cyanobacterium* ESFC-1] | 64% |
| gi\|546205868\|WP_021829404.1 | Sulfate permease [*Crocosphaera watsonii*] | 64% |
| gi\|497240927\|WP_009555169.1 | sulfate permease-like transporter, MFS superfamily [*Oscillatoriales cyanobacterium* JSC-12] | 64% |
| gi\|515870653\|WP_017301247.1 | hypothetical protein [*Nodosilinea nodulosa*] | 64% |
| gi\|220907284\|YP_002482595.1 | sulfate transporter [*Cyanothece* sp. PCC 7425] | 64% |

TABLE 3-continued

DNA and protein sequences showing significant similarity to BicA from *Synechococcus* sp. PCC 7002 determined from a BLASTP search of Genbank using accession numbers YP_001735604.1 for BicA protein. Only sequences with amino acid sequence identity of ≥60% to BicA are shown.

| Accession Numbers | Description | Percent Identity |
|---|---|---|
| gi\|495318765\|WP_008043512.1 | sulfate permease family protein [*Reinekea blandensis*] | 63% |
| gi\|479127405\|YP_005067365.1 | putative transporter [*Arthrospira platensis* NIES-39] | 63% |
| gi\|86606083\|YP_474846.1 | SulP family sulfate permease [*Synechococcus* sp. JA-3-3Ab] | 63% |
| gi\|493666202\|WP_006616548.1 | Sulfate transporter/antisigma-factor antagonist STAS [*Arthrospira platensis*] | 63% |
| gi\|493674094\|WP_006624413.1 | sulfate transporter [*Arthrospira platensis*] | 63% |
| gi\|493563138\|WP_006516526.1 | sulfate permease-like transporter, MFS superfamily [*Leptolyngbya* sp. PCC 7375] | 63% |
| gi\|493719185\|WP_006668694.1 | sulphate transporter [*Arthrospira maxima*] | 62% |
| gi\|497471609\|WP_009785807.1 | Sulfate transporter/antisigma-factor antagonist STAS [*Lyngbya* sp. PCC 8106] | 62% |
| gi\|427740015\|YP_007059559.1 | sulfate permease [*Rivularia* sp. PCC 7116] | 62% |
| gi\|515874763\|WP_017305346.1 | hypothetical protein [*Spirulina subsalsa*] | 62% |
| gi\|194476498\|YP_002048677.1 | low affinity sulfate transporter [*Paulinella chromatophora*] | 62% |
| gi\|428770180\|YP_007161970.1 | sulfate transporter [*Cyanobacterium aponinum* PCC 10605] | 61% |
| gi\|497230225\|WP_009544487.1 | sulfate transporter [*Cyanothece* sp. ATCC 51472] | 61% |
| gi\|172036604\|YP_001803105.1 | sulfate transporter [*Cyanothece* sp. ATCC 51142] | 61% |
| gi\|495552314\|WP_008276893.1 | Sulfate transporter/antisigma-factor antagonist STAS [*Cyanothece* sp. CCY0110] | 60% |

TABLE 4

DNA and protein sequences showing significant similarity to SbtA from *Synechocystis* sp. PCC 6803. Significance was inferred from a BLASTP search of Genbank using accession numbers NP_441340.1 for SbtA protein. Only sequences with amino acid sequence identity of ≥60% to SbtA are shown.

| Accession Numbers | Description | Percent Identity |
|---|---|---|
| gi\|16330612\|NP_441340.1 | hypothetical protein slr1512 [*Synechocystis* sp. PCC 6803] | 100% |
| gi\|220910410\|YP_002485721.1 | hypothetical protein Cyan7425_5063 [*Cyanothece* sp. PCC 7425] sp. PCC 7425] | 84% |
| gi\|56752470\|YP_173171.1 | sodium-dependent bicarbonate transporter [*Synechococcus elongatus* PCC 6301] | 84% |
| gi\|515519067\|WP_016952321.1 | sodium-dependent bicarbonate transporter [*Anabaena* sp. PCC 7108] | 83% |
| gi\|488855361\|WP_002767671.1 | Sodium-dependent bicarbonate transporter [*Microcystis aeruginosa*] | 83% |
| gi\|553829840\|AGY61240.1 | SbtA [*Microcystis aeruginosa* CCAP 1450/10] | 83% |
| gi\|553829806\|AGY61234.1 | SbtA [*Microcystis aeruginosa* UvA V163] | 83% |
| gi\|488869993\|WP_002782232.1 | Sodium-dependent bicarbonate transporter [*Microcystis aeruginosa*] | 83% |
| gi\|488878716\|WP_002790941.1 | Sodium-dependent bicarbonate transporter [*Microcystis aeruginosa*] | 83% |
| gi\|488822968\|WP_002735374.1 | hypothetical protein [*Microcystis aeruginosa*] | 83% |
| gi\|488873371\|WP_002785596.1 | Sodium-dependent bicarbonate transporter [*Microcystis aeruginosa*] | 83% |
| gi\|488885100\|WP_002797325.1 | Sodium-dependent bicarbonate transporter [*Microcystis aeruginosa*] | 83% |
| gi\|488866691\|WP_002778930.1 | Sodium-dependent bicarbonate transporter [*Microcystis aeruginosa*] | 83% |
| gi\|166368950\|YP_001661223.1 | sodium-dependent bicarbonate transporter [*Microcystis aeruginosa* NIES-843] | 83% |
| gi\|553829774\|AGY61229.1 | SbtA [*Microcystis aeruginosa* UvA V145] | 83% |
| gi\|495482524\|WP_008207211.1 | Sodium-dependent bicarbonate transporter [*Microcystis* sp. T1-4] | 83% |
| gi\|488845293\|WP_002757699.1 | Sodium-dependent bicarbonate transporter [*Microcystis aeruginosa*] | 82% |
| gi\|488839197\|WP_002751603.1 | Sodium-dependent bicarbonate transporter [*Microcystis aeruginosa*] | 82% |
| gi\|17229626\|NP_486174.1 | hypothetical protein all2134 [*Nostoc* sp. PCC 7120] | 82% |
| gi\|428206781\|YP_007091134.1 | hypothetical protein Chro_1748 [*Chroococcidiopsis thermalis* PCC 7203] | 82% |
| gi\|428309622\|YP_007120599.1 | permease [*Microcoleus* sp. PCC 7113] | 82% |
| gi\|434399518\|YP_007133522.1 | protein of unknown function DUF897 [*Stanieria cyanosphaera* PCC 7437] | 82% |
| gi\|513847780\|WP_016515722.1 | hypothetical protein [*Microcystis aeruginosa*] | 82% |
| gi\|218246099\|YP_002371470.1 | hypothetical protein PCC8801_1249 [*Cyanothece* sp. PCC 8801] | 81% |

TABLE 4-continued

DNA and protein sequences showing significant similarity to SbtA from *Synechocystis* sp. PCC 6803. Significance was inferred from a BLASTP search of Genbank using accession numbers NP_441340.1 for SbtA protein. Only sequences with amino acid sequence identity of ≥60% to SbtA are shown.

| Accession Numbers | Description | Percent Identity |
|---|---|---|
| gi\|515881377\|WP_017311960.1 | sodium-dependent bicarbonate transporter [*Fischerella* sp. PCC 9339] | 81% |
| gi\|427708938\|YP_007051315.1 | hypothetical protein Nos7107_3597 [*Nostoc* sp. PCC 7107] | 81% |
| gi\|75909236\|YP_323532.1 | hypothetical protein Ava_3027 [*Anabaena variabilis* ATCC 29413] | 81% |
| gi\|428297917\|YP_007136223.1 | hypothetical protein Cal6303_1190 [*Calothrix* sp. PCC 6303] | 80% |
| gi\|515864128\|WP_017294756.1 | sodium-dependent bicarbonate transporter [*Geminocystis herdmanii*] | 80% |
| gi\|427729931\|YP_007076168.1 | permease [*Nostoc* sp. PCC 7524] | 80% |
| gi\|34333991\|AAQ64628.1 | bicarbonate transporter [*Synechococcus elongatus* PCC 7942] | 79% |
| gi\|497454099\|WP_009768297.1 | putative permease [*Oscillatoriales cyanobacterium* JSC-12] | 78% |
| gi\|515859064\|WP_017289692.1 | sodium-dependent bicarbonate transporter [*Leptolyngbya boryana*] | 77% |
| gi\|428225382\|YP_007109479.1 | hypothetical protein GEI7407_1945 [*Geitlerinema* sp. PCC 7407] | 76% |
| gi\|428769062\|YP_007160852.1 | hypothetical protein Cyan10605_0670 [*Cyanobacterium aponinum* PCC 10605] | 74% |
| gi\|479129117\|YP_005069077.1 | putative Na+-dependent bicarbonate transporter [*Arthrospira platensis* NIES-39] | 74% |
| gi\|515873153\|WP_017303736.1 | sodium-dependent bicarbonate transporter [*Spirulina subsalsa*] | 73% |
| gi\|218438254\|YP_002376583.1 | hypothetical protein PCC7424_1268 [*Cyanothece* sp. PCC 7424] | 73% |
| gi\|170077096\|YP_001733734.1 | sodium-dependent bicarbonate transporter [*Synechococcus* sp. PCC 7002] | 72% |
| gi\|516257177\|WP_017661140.1 | sodium-dependent bicarbonate transporter [*Geitlerinema* sp. PCC 7105] | 72% |
| gi\|493040587\|WP_006106213.1 | conserved domain protein [*Coleofasciculus chthonoplastes*] | 72% |
| gi\|553730044\|WP_023064733.1 | hypothetical protein [*Lyngbya aestuarii*] | 70% |
| gi\|428214259\|YP_007087403.1 | permease [*Oscillatoria acuminata* PCC 6304] | 70% |
| gi\|427722211\|YP_007069488.1 | hypothetical protein Lepto7376_0209 [*Leptolyngbya* sp. PCC 7376] | 70% |
| gi\|517209127\|WP_018397945.1 | sodium-dependent bicarbonate transporter [*filamentous cyanobacterium* ESFC-1] | 70% |
| gi\|515870417\|WP_017301016.1 | sodium-dependent bicarbonate transporter [*Nodosilinea nodulosa*] | 70% |
| gi\|428781559\|YP_007173345.1 | permease [*Dactylococcopsis salina* PCC 8305] | 70% |
| gi\|518335387\|WP_019505594.1 | sodium-dependent bicarbonate transporter [*Pleurocapsa* sp. PCC 7319] | 69% |
| gi\|493560850\|WP_006514272.1 | putative permease [*Leptolyngbya* sp. PCC 7375] | 69% |
| gi\|428774738\|YP_007166525.1 | hypothetical protein PCC7418_0056 [*Halothece* sp. PCC 7418] | 69% |
| gi\|497468422\|WP_009782620.1 | hypothetical protein [*Lyngbya* sp. PCC 8106] | 69% |
| gi\|546232429\|WP_021835578.1 | putative sodium-dependent bicarbonate transporter [*Crocosphaera watsonii*] | 68% |
| gi\|497233136\|WP_009547398.1 | protein of unknown function DUF897 [*Cyanothece* sp. ATCC 51472] | 68% |
| gi\|172037852\|YP_001804353.1 | sodium dependent bicarbonate transporter [*Cyanothece* sp. ATCC 51142] | 68% |
| gi\|546217938\|WP_021831484.1 | putative sodium-dependent bicarbonate transporter [*Crocosphaera watsonii*] | 68% |
| gi\|494523485\|WP_007312938.1 | putative sodium-dependent bicarbonate transporter [*Crocosphaera watsonii*] | 68% |
| gi\|515383607\|WP_016876787.1 | sodium-dependent bicarbonate transporter [*Chlorogloeopsis*] | 68% |
| gi\|495591160\|WP_008315739.1 | putative permease [*Leptolyngbya* sp. PCC 6406] | 68% |
| gi\|493555498\|WP_006509029.1 | putative permease [*Xenococcus* sp. PCC 7305] | 68% |
| gi\|494518490\|WP_007307945.1 | Protein of unknown function DUF897 [*Crocosphaera watsonii*] | 67% |
| gi\|515895425\|WP_017326008.1 | hypothetical protein [*Synechococcus* sp. PCC 7336] | 67% |
| gi\|493209531\|WP_006195355.1 | hypothetical protein [*Nodularia spumigena*] | 67% |
| gi\|553738049\|WP_023072267.1 | permease [*Leptolyngbya* sp. Heron Island J] | 67% |
| gi\|495594993\|WP_008319572.1 | putative permease [*Leptolyngbya* sp. PCC 6406] | 67% |
| gi\|495550838\|WP_008275417.1 | sodium-dependent bicarbonate transporter [*Cyanothece* sp. CCY0110] | 67% |
| gi\|158337287\|YP_001518462.1 | hypothetical protein AM1_4164 [*Acaryochloris marina* MBIC11017] | 67% |
| gi\|498158617\|WP_010472773.1 | hypothetical protein [*Acaryochloris* sp. CCMEE 5410] | 67% |
| gi\|427736705\|YP_007056249.1 | permease [*Rivularia* sp. PCC 7116] | 66% |
| gi\|493503468\|WP_006457939.1 | conserved domain protein [*Synechococcus* sp. PCC 7335] | 66% |
| gi\|434394120\|YP_007129067.1 | protein of unknown function DUF897 [*Gloeocapsa* sp. PCC 7428] | 66% |
| gi\|428220035\|YP_007083507.1 | hypothetical protein Pse7367_3848 [*Pseudanabaena* sp. PCC 7367] | 66% |
| gi\|516317314\|WP_017714008.1 | sodium-dependent bicarbonate transporter [*Prochlorothrix hollandica*] | 65% |
| gi\|557413005\|WP_023415178.1 | hypothetical protein [*uncultured Thiohalocapsa* sp. PB-PSB1] | 62% |
| gi\|493168648\|WP_006172554.1 | hypothetical protein [*Synechococcus* sp. WH 5701] | 62% |
| gi\|427703739\|YP_007046961.1 | permease [*Cyanobium gracile* PCC 6307] | 61% |
| gi\|494359788\|WP_007194431.1 | protein of unknown function DUF897 [*Thiocapsa marina*] | 61% |
| gi\|493967528\|WP_006910814.1 | sodium-dependent bicarbonate transporter [*Cyanobium* sp. PCC 7001] | 60% |

As used herein, "percent homology" of two amino acid sequences or of two nucleic acid sequences is determined using the algorithm of Karlin and Altschul (1990) *Proc. Natl. Acad. Sci., U.S.A.* 87: 2264-2268. Such an algorithm is incorporated into the NBLAST and XBLAST programs of Altschul et al. (1990) *J. Mol. Biol.* 215: 403-410. BLAST nucleotide searches are performed with the NBLAST program, score=100, word length 12, to obtain nucleotide sequences homologous to a nucleic acid molecule of the invention. BLAST protein searches are performed with the XBLAST program, score=50, word length=3, to obtain amino acid sequences homologous to a reference polypeptide (e.g., SEQ ID NO:5). To obtain gapped alignments for comparison purposes, Gapped BLAST is utilized as described in Altschul et al. (1997) *Nucleic Acids Res.* 25: 3389-3402. When utilizing BLAST and Gapped BLAST programs, the default parameters are typically used. (See http://www.ncbi.nlm.nih.gov)

In addition, polynucleotides that are substantially identical to a polynucleotide encoding a SbtA, BicA, CCP1, or LCIA polypeptide are included. By "substantially identical" is meant a polypeptide or polynucleotide having a sequence that is at least about 85%, specifically about 90%, and more specifically about 95% or more identical to the sequence of the reference amino acid or nucleic acid sequence. For polypeptides, the length of the reference polypeptide sequence will generally be at least about 16 amino acids, or specifically at least about 20 amino acids, more specifically at least about 25 amino acids, and most specifically at least about 35 amino acids. For nucleic acids, the length of the reference nucleic acid sequence will generally be at least about 50 nucleotides, specifically at least about 60 nucleotides, more specifically at least about 75 nucleotides, and most specifically at least about 110 nucleotides.

Typically, homologous sequences can be confirmed by hybridization, wherein hybridization under stringent conditions. Using the stringent hybridization (i.e., washing the nucleic acid fragments twice where each wash is at room temperature for 30 minutes with 2× sodium chloride and sodium citrate (SCC buffer; 1.150. mM sodium chloride and 15 mM sodium citrate, pH 7.0) and 0.1% sodium dodecyl sulfate (SDS); followed by washing one time at 50° C. for 30 minutes with 2×SCC and 0.1% SDS; and then washing two times where each wash is at room temperature for 10 minutes with 2×SCC), homologous sequences can be identified comprising at most about 25 to about 30% base pair mismatches, or about 15 to about 25% base pair mismatches, or about 5 to about 15% base pair mismatches.

Polynucleotides encoding SbtA, BicA, CCP1, or LCIA polypeptide sequences allow for the preparation of relatively short DNA (or RNA) sequences having the ability to specifically hybridize to such gene sequences. The short nucleic acid sequences may be used as probes for detecting the presence of complementary sequences in a given sample, or may be used as primers to detect, amplify or mutate a defined segment of the DNA sequences encoding a SbtA, BicA, CCP1, or LCIA polypeptide. A nucleic acid sequence employed for hybridization studies may be greater than or equal to about 14 nucleotides in length to ensure that the fragment is of sufficient length to form a stable and selective duplex molecule. Such fragments are prepared, for example, by directly synthesizing the fragment by chemical means, by application of nucleic acid reproduction technology, such as PCR technology, or by excising selected nucleic acid fragments from recombinant plasmids containing appropriate inserts and suitable restriction sites.

The term bicarbonate transporter includes polynucleotides that encode the SbtA, BicA, CCP1, or LCIA polypeptides or full-length proteins that contain substitutions, insertions, or deletions into the polypeptide backbone. Related polypeptides are aligned with SbtA, BicA, CCP1, or LCIA by assigning degrees of homology to various deletions, substitutions and other modifications. Homology can be determined along the entire polypeptide or polynucleotide, or along subsets of contiguous residues. The percent identity is the percentage of amino acids or nucleotides that are identical when the two sequences are compared. The percent similarity is the percentage of amino acids or nucleotides that are chemically similar when the two sequences are compared. SbtA, BicA, CCP1, or LCIA, and homologous polypeptides are preferably greater than or equal to about 75%, preferably greater than or equal to about 80%, more preferably greater than or equal to about 90% or most preferably greater than or equal to about 95% identical.

A homologous polypeptide may be produced, for example, by conventional site-directed mutagenesis of polynucleotides (which is one avenue for routinely identifying residues of the molecule that are functionally important or not), by random mutation, by chemical synthesis, or by chemical or enzymatic cleavage of the polypeptides.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria.

Reference herein to either the nucleotide or amino acid sequence of SbtA, BicA, CCP1, or LCIA also includes reference to naturally occurring variants of these sequences. Non-naturally occurring variants that differ from SEQ ID NOs:1, 3, 5, or 7 (nucleotide) and 2, 4, 6, or 8 (amino acid) and retain biological function are also included herein. Preferably the variants comprise those polypeptides having conservative amino acid changes, i.e., changes of similarly charged or uncharged amino acids. Genetically encoded amino acids are generally divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. As each member of a family has similar physical and chemical properties as the other members of the same family, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule. Whether an amino acid change results in a functional polypeptide can readily be determined by assaying the properties of transgenic plants containing the SbtA, BicA, CCP1, or LCIA derivatives.

Reference to SbtA, BicA, CCP1, or LCIA also refers to polypeptide derivatives of SbtA, BicA, CCP1, or LCIA. As used herein, "polypeptide derivatives" include those polypeptides differing in length from a naturally-occurring SbtA, BicA, CCP1, or LCIA and comprising about five or more amino acids in the same primary order as is found in SbtA, BicA, CCP1, or LCIA. Polypeptides having substantially the same amino acid sequence as ASbtA, BicA, CCP1, or LCIA but possessing minor amino acid substitutions that do not substantially affect the ability of SbtA, BicA, CCP1, or LCIA polypeptide derivatives to interact with SbtA, BicA, CCP1, or LCIA-specific molecules, respectively, such as antibodies, are within the definition of SbtA, BicA, CCP1, or LCIA polypeptide derivatives. Polypeptide derivatives also include glycosylated forms, aggregative conjugates with other molecules and covalent conjugates with unrelated chemical moieties.

In one embodiment, the bicarbonate transporter (e.g., SbtA, BicA, CCP1, or LCIA genes or their homologs) are expressed in vectors suitable for in vivo expression such as, for example, plant expression systems. The bicarbonate transporter polynucleotides are inserted into a recombinant expression vector or vectors. The term "recombinant expression vector" refers to a plasmid, virus, or other means known in the art that has been manipulated by insertion or incorporation of the bicarbonate transporter genetic sequence. The term "plasmids" generally is designated herein by a lower case p preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors are transformed into a suitable host cell to form a host cell vector system for the production of a polypeptide.

The term recombinant polynucleotide or nucleic acid refers to a polynucleotide that is made by the combination of two otherwise separated segments of sequence accomplished by the artificial manipulation of isolated segments of polynucleotides by genetic engineering techniques or by chemical synthesis. In so doing, one may join together polynucleotide segments of desired functions to generate a desired combination of functions.

The terms "isolated" or "purified", used interchangeably herein, refers to a nucleic acid, a polypeptide, or other biological moiety that is removed from components with which it is naturally associated. The term "isolated" can refer to a polypeptide that is separate and discrete from the whole organism with which the molecule is found in nature or is present in the substantial absence of other biological macro-molecules of the same type. The term "isolated" with respect to a polynucleotide can refer to a nucleic acid molecule devoid, in whole or part, of sequences normally associated with it in nature; or a sequence, as it exists in nature, but having heterologous sequences in association therewith; or a molecule disassociated from the chromosome. Purity and homogeneity are typically determined using analytical chemistry techniques, for example polyacrylamide gel electrophoresis or high performance liquid chromatography. In some embodiments, the term "purified" means that the nucleic acid or protein is at least 85% pure, specifically at least 90% pure, more specifically at least 95% pure, or yet more specifically at least 99% pure.

The term transgene refers to a recombinant polynucleotide or nucleic acid that comprises a coding sequence encoding a protein or RNA molecule.

The bicarbonate transporter polynucleotides are inserted into a vector adapted for expression in a plant, bacterial, yeast, insect, amphibian, or mammalian cell that further comprises the regulatory elements necessary for expression of the nucleic acid molecule in the plant, bacterial, yeast, insect, amphibian, or mammalian cell operatively linked to the nucleic acid molecule encoding a bicarbonate transporter. Suitable vectors for plant expression include T-DNA vectors. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns (if introns are present), maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included. If a promoter is inducible, there are sequences present that mediate regulation of expression so that the associated sequence is transcribed only when an inducer (e.g., light) is available to the plant or plant tissue. An exemplary promoter is the 35S cauliflower mosaic virus (CaMV) promoter to provide basal expression and avoid overexpression in transgenic plants.

With respect to a coding sequence, the term "plant-expressible" means that the coding sequence (nucleotide sequence) can be efficiently expressed by plant cells, tissue and/or whole plants. As used herein, a plant-expressible coding sequence has a GC composition consistent with acceptable gene expression in plant cells, a sufficiently low CpG content so that expression of that coding sequence is not restricted by plant cells, and codon usage that is consistent with that of plant genes. Where it is desired that the properties of the plant-expressible gene are identical to those of the naturally occurring gene, the plant-expressible homolog will have a synonymous coding sequence or a substantially synonymous coding sequence. A substantially synonymous coding sequence is one in that there are codons that encode similar amino acids to a comparison sequence, or if the amino acid substituted is not similar in properties to the one it replaces, that change has no significant effect on enzymatic activity for at least one substrate of that enzyme. As discussed herein, it is well understood that in most cases, there is some flexibility in amino acid sequence such that function is not significantly changed. Conservative changes in amino acid sequence, and the resultant similar protein can be readily tested using procedures such as those disclosed herein. Where it is desired that the plant-expressible gene have different properties, there can be variation in the amino acid sequence as compared to the wild-type gene, and the properties of enhanced photosynthesis can be readily determined as described herein.

"Plant-expressible transcriptional and translational regulatory sequences" are those that can function in plants, plant tissue and/or plant cells to effect the transcriptional and translational expression of the nucleotide sequences with that they are associated. Included are 5' sequences that qualitatively control gene expression (turn on or off gene expression in response to environmental signals such as light, or in a tissue-specific manner) and quantitative regulatory sequences that advantageously increase the level of downstream gene expression. An example of a sequence motif that serves as a translational control sequence is that of the ribosome binding site sequence. Polyadenylation signals are examples of transcription regulatory sequences positioned downstream of a target sequence. Exemplary flanking sequences include the 3' flanking sequences of the nos gene of the *Agrobacterium tumefaciens* Ti plasmid. The upstream nontranslated sequence of a bacterial merA coding sequence can be utilized to improve expression of other sequences in plants as well.

The plant-expressible transcription regulatory sequence optionally comprises a constitutive promoter to drive gene expression throughout the whole plant or a majority of plant tissues. In one embodiment, the constitutive promoter drives gene expression at a higher level than the endogenous plant gene promoter. In one embodiment, the constitutive promoter drives gene expression at a level that is at least two-fold higher, specifically at least five-fold higher, and more specifically at least ten-fold higher than the endogenous plant gene promoter. Suitable constitutive promoters include plant virus promoters such as the cauliflower mosaic virus (CaMV) 35S and 19S promoters. An exemplary plant virus promoter is the cauliflower mosaic virus 35S promoter. Suitable constitutive promoters further include promoters for plant genes that are constitutively expressed such as the plant ubiquitin, Rubisco, and actin promoters such as the ACT1 and ACT2 plant actin genes. Exemplary plant gene promoters include the ACT2 promoter from *Arabidopsis* (locus AT3G18780; SEQ ID. NO:12) and the ACT1 promoter from rice (GenBank Accession no. S44221.1; SEQ ID. NO:13).

Where a regulatory element is to be coupled to a constitutive promoter, generally a truncated (or minimal) promoter is used, for example, the truncated 35S promoter of Cauliflower Mosaic Virus. Truncated versions of other constitutive promoters can also be used to provide CAAT and TATA-homologous regions; such promoter sequences can be derived from those of *Agrobacterium tumefaciens* T-DNA genes such as nos, ocs and mas and plant virus genes such as the CaMV 19S gene or the ACT2 gene of *Arabidopsis*. Translational control sequences specifically exemplified herein are the nucleotides between 8 and 13 upstream of the ATG translation start codon for bacterial signals and from nucleotides 1 to 7 upstream of the ATG translation start codon for plants.

A minimal promoter contains the DNA sequence signals necessary for RNA polymerase binding and initiation of transcription. For RNA polymerase II promoters the promoter is identified by a TATA-homologous sequences motif about 20 to 50 base pairs upstream of the transcription start site and a CAAT-homologous sequence motif about 50 to 120 base pairs upstream of the transcription start site. By convention, the nucleotides upstream of the transcription start with increasingly large numbers extending upstream of (in the 5' direction) from the start site. In one embodiment, transcription directed by a minimal promoter is low and does not respond either positively or negatively to environmental or developmental signals in plant tissue. An exemplary minimal promoter suitable for use in plants is the truncated CaMV 35S promoter, that contains the regions from −90 to +8 of the 35S gene. Where high levels of gene expression are desired, transcription regulatory sequences that upregulate the levels of gene expression may be operatively linked to a minimal promoter is used thereto. Such quantitative regulatory sequences are exemplified by transcription enhancing regulatory sequences such as enhancers.

In one embodiment, the plant-expressible transcription regulatory sequence comprises a tissue or organ-specific promoter to drive gene expression in selected organs such as roots or shoots and tissues therein. In one embodiment, the organ-specific promoter drives gene expression in below ground tissues such as roots and root hairs. In one embodiment, the organ-specific promoter drives gene expression in above ground tissues such as shoots and leaves. An exemplary leaf-specific promoter is the SRS1 promoter. In one embodiment, the organ-specific promoter drives gene expression in floral and reproductive tissues.

The plant-expressible transcription regulatory sequence optionally comprises an inducible promoter to drive gene expression in response to selected stimuli. Suitable inducible promoters include a light inducible promoter such as the SRS1 promoter, and the chlorophyll A/13 binding protein light-inducible transcription regulatory sequences.

The choice of vector used for constructing the recombinant DNA molecule depends on the functional properties desired, e.g., replication, protein expression, and the host cell to be transformed. In one embodiment, the vector comprises a prokaryotic replicon, i.e., a DNA sequence having the ability to direct autonomous replication and maintenance of the recombinant DNA molecule extra-chromosomally when introduced into a prokaryotic host cell, such as a bacterial host cell. In addition, the vector may also comprise a gene whose expression confers a selective advantage, such as a drug resistance, to the bacterial host cell when introduced into those transformed cells. Suitable bacterial drug resistance genes are those that confer resistance to ampicillin or tetracycline, among other selective agents. The neomycin phosphotransferase gene has the advantage that it is expressed in eukaryotic as well as prokaryotic cells.

Vectors typically include convenient restriction sites for insertion of a recombinant DNA molecule. Suitable vector plasmids include pUC8, pUC9, pBR322, and pBR329 available from BioRad Laboratories (Richmond, Calif.) and pPL, pK and K223 available from Pharmacia (Piscataway, N.J.), and pBLUESCRIPT® and pBS available from Stratagene (La Jolla, Calif.). Suitable vectors include, for example, Lambda phage vectors including the Lambda ZAP vectors available from Stratagene (La Jolla, Calif.). Other exemplary vectors include pCMU. Other appropriate vectors may also be synthesized, according to known methods; for example, vectors pCMU/K$^b$ and pCMUII which are modifications of pCMUIV.

Suitable expression vectors capable of expressing a recombinant nucleic acid sequence in plant cells and capable of directing stable integration within the host plant cell include vectors derived from the tumor-inducing (Ti) plasmid of *Agrobacterium tumefaciens*, and several other expression vector systems known to function in plants. See for example, Verma et al., No. WO87/00551, incorporated herein by reference. Other suitable expression vectors include gateway cloning-compatible plant destination vectors for expression of proteins in transgenic plants, e.g., the pEarleygate series (Earley et al. The Plant Journal Volume 45, Issue 4, pages 616-629, February 2006).

Expression and cloning vectors optionally contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Suitable selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend, in part, on the host cell.

One of the most commonly used markers for the selection of transgenic plants is resistance to glufosinate ammonium, an herbicide that is sold under a variety of trade names including Basta and Finale. Resistance to glufosinate ammonium is conferred by the bacterial bialophos resistance gene (BAR) encoding the enzyme phosphinotricin acetyl transferase (PAT). The major advantage of glufosinate ammonium selection is that it can be performed on plants growing in soil and does not require the use of sterile techniques.

In one embodiment, the bicarbonate transporter coding sequence is cloned into a vector suitable for expression in *Camelina* under the control of different constitutive promoters including the CaMV 35S promoter and the actin promoters from *Arabidopsis* and rice. In one embodiment, the bicarbonate transporter coding sequence is regulated by an organ or tissue-specific or an inducible promoter. An exemplary tissue-specific promoter is the leaf-specific SRS1 promoter. In one embodiment, the bicarbonate transportere coding sequence is cloned into a plant expression cassette construct or vector comprising a promoter, convenient cloning sites and the nos transcription terminator (NOSt). In one embodiment, the bicarbonate transporter is cloned into a plant expression cassette in a pEarlygate plasmid.

Transformation of a host cell with an expression vector or other DNA is carried out by conventional techniques as are well known to those skilled in the art. By "transformation" is meant a permanent or transient genetic change induced in a cell following incorporation of new DNA (i.e., DNA exogenous to the cell). Where the cell is a plant cell, a permanent genetic change is generally achieved by introduction of the DNA into the genome of the cell. By "transformed cell" or "host cell" is meant a cell (e.g., prokaryotic or eukaryotic) into which (or into an ancestor of which) has been introduced, by means of recombinant DNA techniques, a DNA molecule encoding a bicarbonate transporter (e.g., a SbtA, BicA, CCP1, or LCIA polypeptide), or fragment thereof.

Recombinant host cells, in the present context, are those that have been genetically modified to contain an isolated DNA molecule. The DNA can be introduced by a means that is appropriate for the particular type of cell, including without limitation, transfection, transformation, lipofection, or electroporation.

Also included herein are transgenic plants that have been transformed with a bicarbonate transporter gene. A "transgenic plant" is one that has been genetically modified to contain and express recombinant DNA sequences, either as regulatory RNA molecules or as proteins. As specifically exemplified herein, a transgenic plant is genetically modified to contain and express a recombinant DNA sequence operatively linked to and under the regulatory control of transcriptional control sequences that function in plant cells or tissue or in whole plants. As used herein, a transgenic plant also encompasses progeny of the initial transgenic plant where those progeny contain and are capable of expressing the recombinant coding sequence under the regulatory control of the plant-expressible transcription control sequences described herein. Seeds containing transgenic embryos are encompassed within this definition.

Individual plants within a population of transgenic plants that express a recombinant gene may have different levels of gene expression. The variable gene expression is due to multiple factors including multiple copies of the recombinant gene, chromatin effects, and gene suppression. Accordingly, a phenotype of the transgenic plant may be measured as a percentage of individual plants within a population. In one embodiment, greater than or equal to about 25% of the transgenic plants express the phenotype. Specifically, greater than or equal to about 50% of the transgenic plants express the phenotype. More specifically, greater than or equal to about 75% of the transgenic plants express the phenotype. The phenotype is increased CO2 assimilation, reduced transpiration rate, increased water use efficiency, increased nitrogen use efficiency, or increased seed yield.

The transgenic plant is transformed with a recombinant polynucleotide or nucleic acid molecule comprising a bicarbonate transporter coding sequence operatively linked to a plant-expressible transcription regulatory sequence. Suitable bicarbonate transporter coding sequences include sequences that are homologous to a bicarbonate transporter gene. Exemplary bicarbonate transporter genes include *Synechocystis* PCC6803 SbtA (SEQ ID NO:1), *Synechococcus* PCC7002 BicA (SEQ ID NO:3), *Chlamydomonas reinhardtii* CCP1 (SEQ ID NO:5), and *Chlamydomonas reinhardtii* LCIA (SEQ ID NO:7). The transgenic plant expresses a heterologous bicarbonate transporter protein which localizes to the plant chloroplast envelope membranes, e.g., the inner envelope membrane. In one embodiment, the bicarbonate transporter protein is homologous to the CCP1 protein. Suitable bicarbonate transporter proteins include bicarbonate transporter proteins from cyanobacteria. Exemplary bicarbonate transporter proteins include *Synechocystis* PCC6803 SbtA (SEQ ID NO:2), *Synechococcus* PCC7002 BicA (SEQ ID NO:4), *Chlamydomonas reinhardtii* CCP1 (SEQ ID NO:6), and *Chlamydomonas reinhardtii* LCIA (SEQ ID NO:8).

The present inventors have transformed plants with recombinant DNA molecules that encode a heterologous bicarbonate transporter in the nuclear genome. The expressed recombinant bicarbonate transporter localizes to the chloroplast inner envelope membrane. Transgenic plants and plant cells expressing the recombinant heterologous bicarbonate transporter gene show enhanced $CO_2$ assimilation and reduced transpiration rates compared to wild type plants of the same species not comprising the recombinant heterologous bicarbonate transporter. The transgenic plants also show increased seed yield compared to wild type plants of the same species not comprising the recombinant heterologous bicarbonate transporter.

A recombinant DNA construct including a plant-expressible gene or other DNA of interest is inserted into the genome of a plant by a suitable method. Suitable methods include, for example, *Agrobacterium tumefaciens*-mediated DNA transfer, direct DNA transfer, liposome-mediated DNA transfer, electroporation, co-cultivation, diffusion, particle bombardment, microinjection, gene gun, calcium phosphate coprecipitation, viral vectors, and other techniques. Suitable plant transformation vectors include those derived from a Ti plasmid of *Agrobacterium tumefaciens*. In addition to plant transformation vectors derived from the Ti or root-inducing (Ri) plasmids of *Agrobacterium*, alternative methods can be used to insert DNA constructs into plant cells. A transgenic plant can be produced by selection of transformed seeds or by selection of transformed plant cells and subsequent regeneration.

In one embodiment, the bicarbonate transporter coding sequence is subcloned under the control of the CaMV 35S promoter and the 3' OCS terminator into the plant expression T-DNA binary vector pEarleyGate 100. This coding sequence and promoter are previously shown to be strongly transcriptionally expressed in most plant tissues. *Camelina sativa* is transformed using vacuum infiltration technology, and the T1 generation seeds are screened for BASTA resistance. Transgenic plants transformed with an isolated bicarbonate transporter polynucleotide are produced. In one embodiment, the plant also expresses a second bicarbonate transporter coding sequence.

In one embodiment, the transgenic plants are grown (e.g., on soil) and harvested. In one embodiment, above ground tissue is harvested separately from below ground tissue. Suitable above ground tissues include shoots, stems, leaves, flowers, grain, and seed. Exemplary below ground tissues include roots and root hairs. In one embodiment, whole plants are harvested and the above ground tissue is subsequently separated from the below ground tissue.

The invention is further illustrated by the following non-limiting examples. Any variations in the exemplified compositions and methods that occur to the skilled artisan are intended to fall within the scope of the present invention.

EXAMPLES

Example 1

Construction of Bicarbonate Transporter Expression Vectors and Plant Transformation Construction of SbtA Gene Fusions and Confirmation of Targeting to Chloroplasts.

Gene constructs were designed to target SbtA (*Synechocystis* PCC6803) bicarbonate transporter from cyanobacteria to chloroplasts. Each construct encoded in-frame fusions of the chloroplast transit peptide of atTic20 from *Arabidopsis thaliana* (110 amino acids) to the N-termini of SbtA to target the proteins to chloroplasts when expressed from the *Camelina* nuclear genome (FIG. 1). atTic20 is a well characterized chloroplast inner envelope membrane protein (Chen et al., 2000, Plant Physiol. 122: 813-822). In addition, the genes contained C-terminal fusions to the c-Myc epitope tag to facilitate confirmation of expression and localization in transgenic plants. An exemplary SbtA (atTic20TP_SbtA_cMyc) DNA construct is provided as SEQ ID NO: 11.

The SbtA (atTic20TP_SbtA_cMyc) construct was inserted into the pUC18 derived vector, pJexpress414, containing upstream bacteriophage T7 promoter and downstream T7 terminator sequences to allow for in vitro translation of the constructs using a T7 coupled transcription-translation system.

Figure 2:
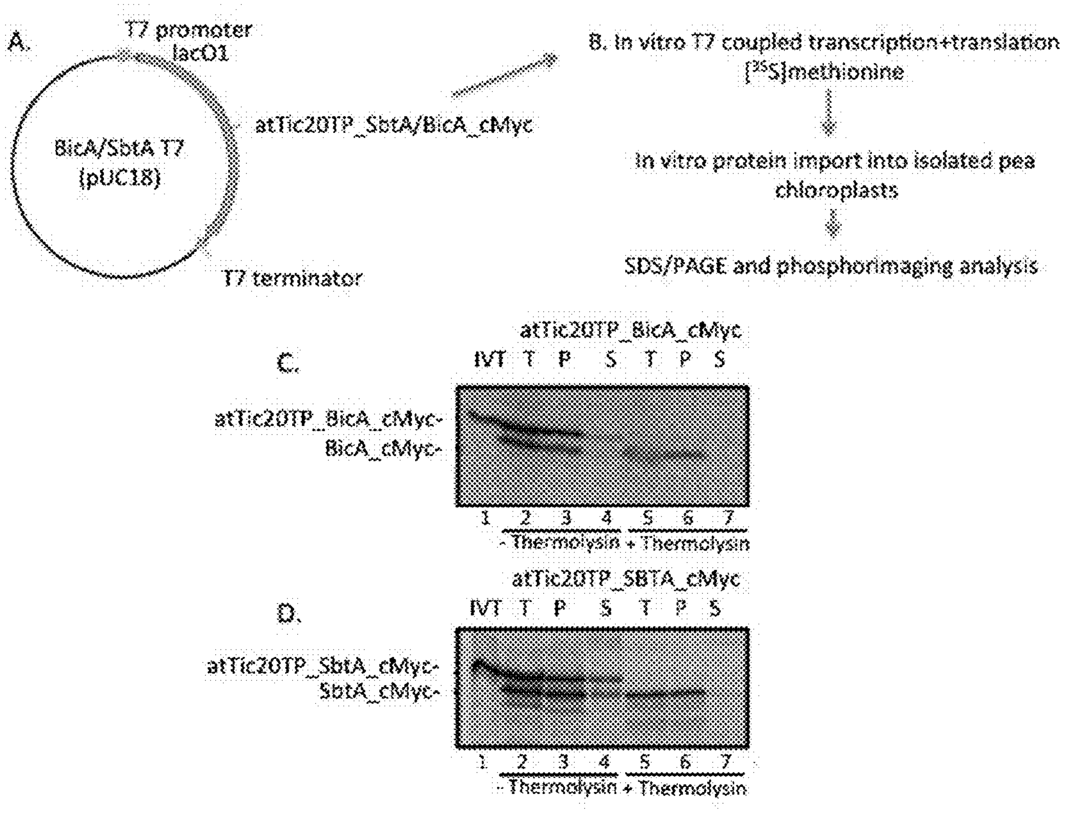
FIG. 2 shows in vitro import of atTic20TP_SbtA_cMyc or atTic20TP_BicA_cMyc into isolated chloroplasts. A. Plasmid constructs used for in vitro expression of fusion proteins, abbreviated BicA/SbtA T7 (pUC18) to indicate that either Bic A or SbtA is present in the plasmid In the diagram, "T7 promoter" represents the T7 bacteriophage transcriptional promoter; "lacO1" represents the lactose operon operator sequence; and "T7 terminator" represents the T7 bacteriophage transcription terminator. B. An abbreviated flow chart of the in vitro expression and chloroplast protein import assays. C. Results from in vitro import of the [$^{35}$S]atTic20TP_BicA_cMyc fusion protein. In vitro translated proteins (lane 1) were incubated with isolated chloroplasts under conditions that promote protein import. D. Results from in vitro import of the [$^{35}$S] atTic20TP_SbtA_cMyc fusion protein. In vitro translated proteins (lane 1) were incubated with isolated chloroplasts under conditions that promote protein import. The protein associates with chloroplasts and is partially processed to its mature forms (lane 2). Treatment of chloroplast with thermolysin following import (lanes 5-7) demonstrates that the mature form has been imported. Fractionation of chloroplasts into membrane and stromal fractions demonstrates that the protein is localized to chloroplast membranes (compare lanes 3 to 4 and 6 to 7).

The construct was translated in the presence of [$^{35}$S] methionine and incubated with isolated pea chloroplasts to investigate their ability to properly target to chloroplasts and associate with envelope membranes. Analysis of the protein import reactions (FIG. 2) demonstrates that the in vitro translation products (lane 1) were imported into isolated chloroplasts, as evidenced by the cleavage of the atTic20 transit peptide to yield a higher mobility species (lane 2). Treatment of the chloroplast following import with thermolysin to digest protein that remained outside the chloroplasts demonstrated that the processed forms of both proteins were protected from proteolysis and therefore fully imported (compare lanes 2 and 5). To confirm that the transporters were integrated into chloroplast membranes, the stroma and membrane fractions were separated by alkaline extraction and differential sedimentation. The transporter fractionated with the membrane pellet fractions (compare lanes 6 and 7) consistent with proper insertion.

Figure 4:
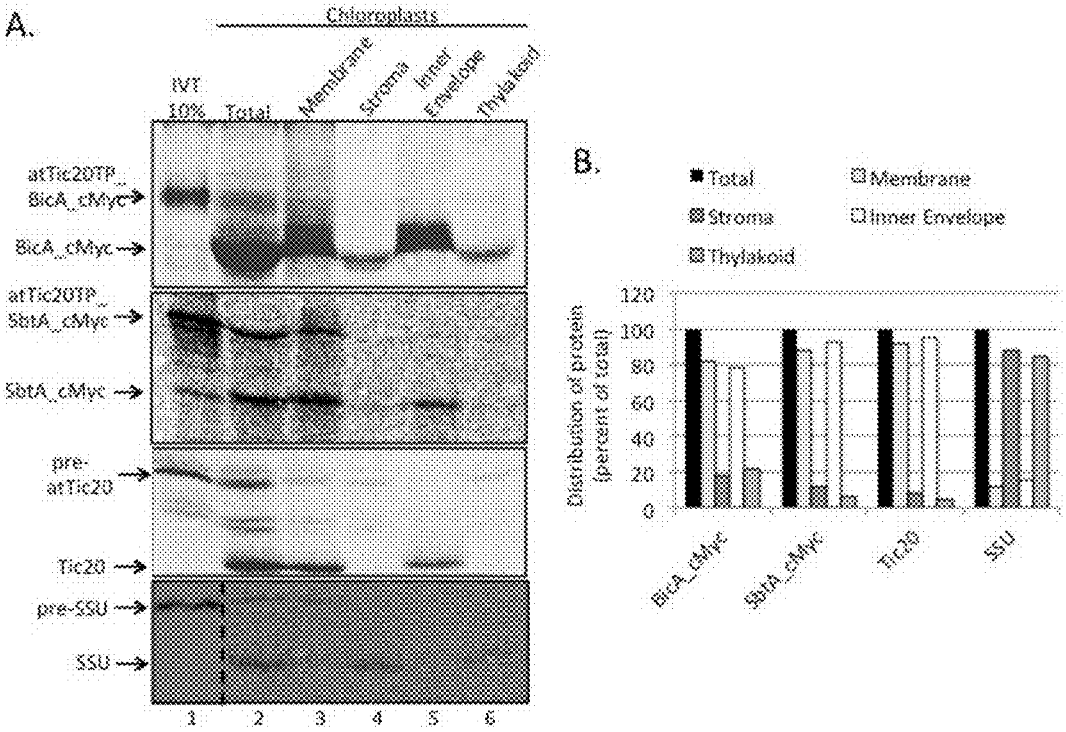
FIG. 4 shows in vitro import and localization of atTic20TP_SbtA_cMyc in isolated chloroplasts. A. In vitro translated [$^{35}$S]atTic20TP_SbtA_cMyc or [$^{35}$S] atTic20TP_BicA_cMyc fusion proteins (lane 1) was incubated with isolated chloroplasts under conditions that promote protein import. Both proteins associate with chloroplasts and are processed to their mature forms (lane 2) and associate with chloroplast membranes (lane 3). Fractionation of the chloroplasts into total membranes (lane 3), stroma (lane 4), inner envelope (lane 5), and thylakoid membranes (lane 6) demonstrate primary association of SbtA_cMyc or BicA_cMyc with inner envelope membranes (lane 5). The distribution is indistinguishable from atTic20, an authentic inner membrane protein (third panel), whereas the small subunit of Rubisco fractionates exclusively with the stroma (fourth panel). B. Quantitative analysis of the distribution of each imported protein in chloroplast fractions relative to the amount found in total chloroplasts confirms BicA_cMyc or SbtA_cMyc localization to the inner envelope. From left to right for each protein the fractions are: total, membrane, stroma, inner envelope, and thylakoid.

[$^{35}$S]methionine-labeled atTic20TP_SbtA_cMyc was imported into isolated pea chloroplasts, and the chloroplasts were subsequently fractionated to yield inner envelope, stromal and thylakoid fractions. The distribution was compared to those of imported atTic20, an authentic inner envelope membrane protein, and the small subunit of Rubisco (SSU), a known stromal protein. FIG. 4 shows that atTic20TP_SbtA_cMyc was imported, processed to its mature form (SbtA_cMyc), and primarily associated with the membrane fraction (FIG. 4A, second panel, compare lanes 1, 2 and 3). SbtA_cMyc fractionated primarily with the inner envelope membrane (FIG. 4A, second panel, compare lanes 4-6 and FIG. 4B). Greater than 75% of protein was associated with the inner envelope (FIG. 4B). This pattern of distribution was similar to that of imported pre-atTic20 (FIG. 4A, third panel and 4B), demonstrating that SbtA_cMyc are properly localized to the inner envelope membrane. By contrast, imported SSU localized almost exclusively to the stromal fraction (FIG. 4A. bottom panel and 4B). The results with the in vitro import assays are unequivocal, and therefore we have targeted the SbtA bicarbonate transporter to the inner envelope membrane of chloroplasts.

Construction of Transformation Vectors for Introducing SbtA Fusion into Plants by Nuclear Transformation.

Individual single-gene constructs encoding atTic20TP_SbtA_cMyc were inserted into a binary plant transformation vector based on pEarleyGate 100 (pEG100) containing a modified 35S cauliflower mosaic virus (CaMV) promoter to provide basal expression and avoid overexpression in transgenic plants. These constructs (FIG. 3; "pEG100 SbtA") were transformed into *Camelina sativa* by *Agrobacterium*-mediated, floral dip transformation based on established methods (Lu & Kang, 2008, Plant Cell Rep, 27, 273-278). 45-50 plants for each vector were transformed. Seed from the T0 plants was collected.

Figure 5:
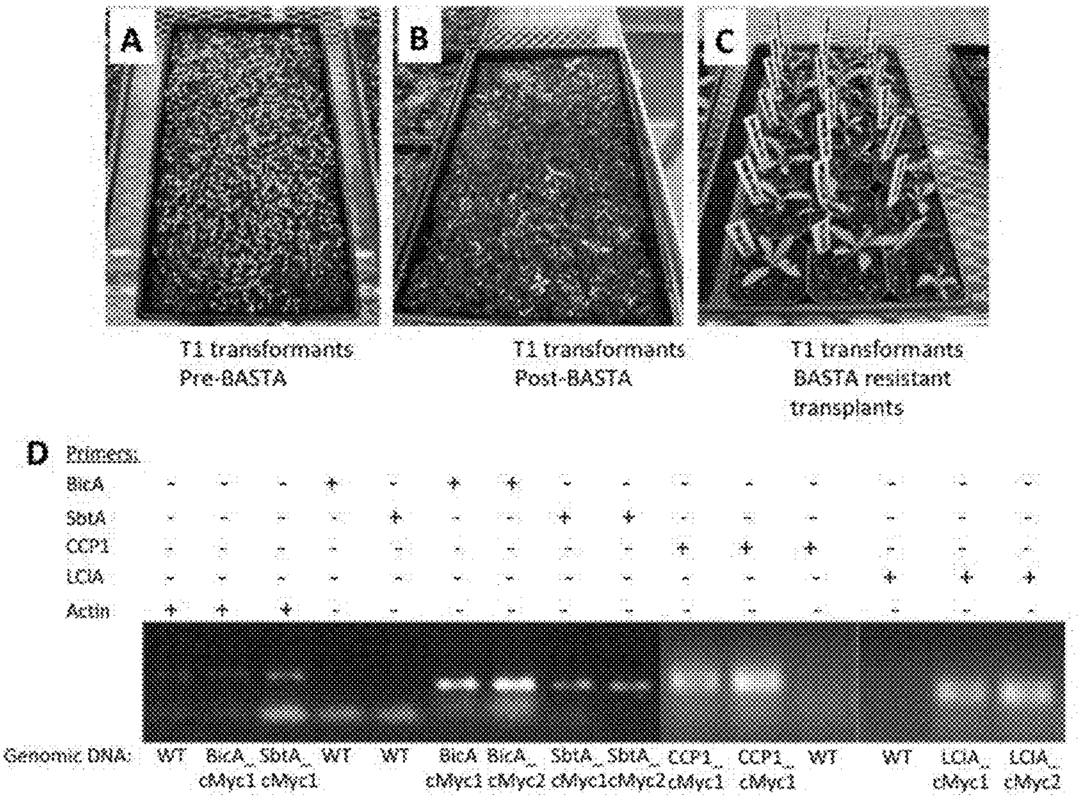
FIG. 5 shows selection of atTic20TP_SbtA_cMyc, atTic20TP_BicA_cMyc, CCP1_cMyc, and LCIA_cMyc T1 transformants. A. An example of T1 seed from transformed *camelina* germinated on soil prior to treatment with BASTA. B. The same plants as in A following three treatments with 200 mg/L BASTA. BASTA resistant transformants are apparent. C. An example of transplanted BASTA resistant lines. D. PCR-based genotyping of representative atTic20TP_SbtA_cMyc, atTic20TP_BicA_cMyc, CCP1_cMyc, and LCIA_cMyc T1 transformants demonstrates the presence of the transgenes. No transgenes are detected in wild type plants. Primers amplifying a gene encoding actin were used as a control for the PCR reaction.

The T1 seedlings from these plants were screened using the BASTA selectable marker present in the T-DNA insertion. FIG. 5 illustrates an example of the successful selection of T1 seedlings by the application of 200 mg/L BASTA herbicide (FIG. 5, compare A and B). BASTA-resistant plants were transplanted (FIG. 5C) and genotyping using PCR of genomic DNA from the T1 lines with gene specific primers (SbtA) or control primers (Actin) confirmed the lines as atTic20TP_SbtA_cMyc transformants (see example in FIG. 5D). Wild type *Camelina* genomic DNA was positive for the actin control, but lacked the transgenes (FIG. 5D).

Figure 7:
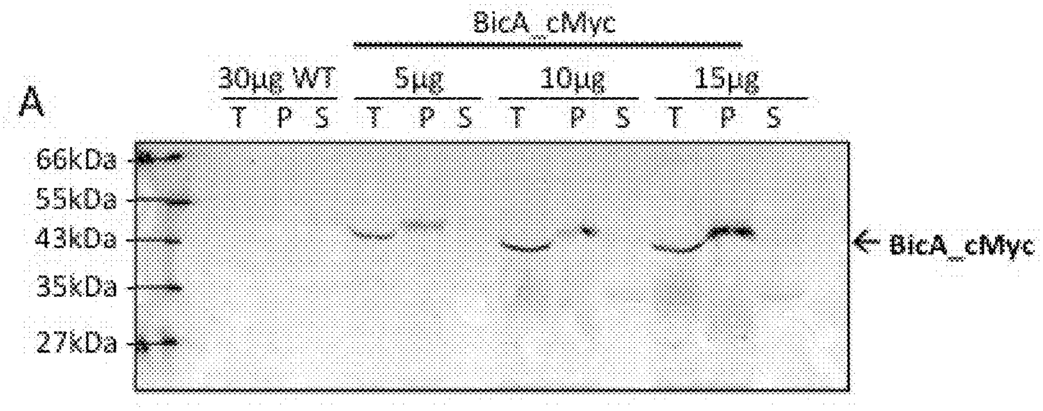
FIG. 7 shows photographs of results for total (T), membrane (P), and soluble stromal (S) fractions from 10 μg of pea chloroplasts and 5 to 30 μg of *camelina* chloroplasts immunoblotted with an anti-cMyc antibody to detect BicA_cMyc (A) or SbtA_cMyc (B).
Figure 7:
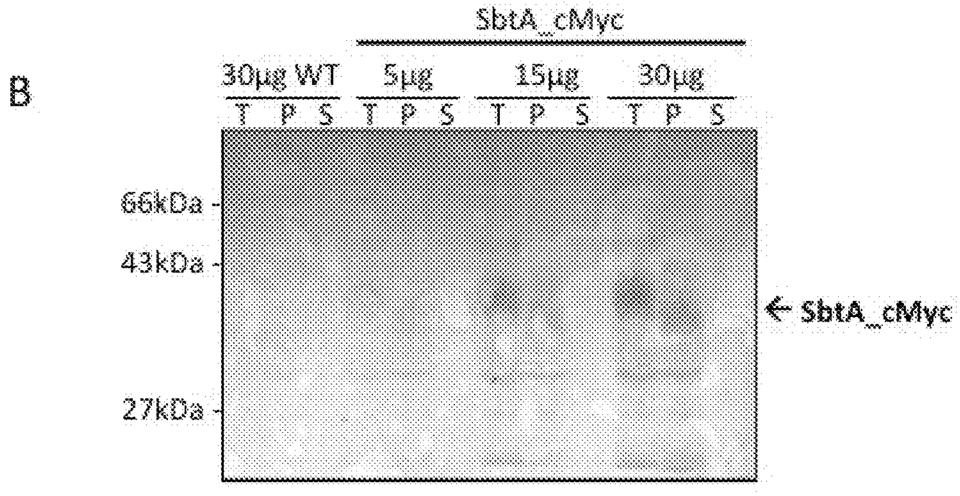

*Camelina* chloroplasts were isolated from a line expressing SbtA_cMyc from the atTic20TP_SbtA_cMyc construct. After fractionating the chloroplasts, immunoblot experiments with anti-cMyc antibodies showed that the transgenic protein is localized to chloroplasts, processed to its mature form, and associated with chloroplast membranes (FIG. 7B). Homozygous T3 transgenic lines for photosynthesis analysis are selected.

Generation of *Camelina* Nuclear Transformants Expressing BicA from Cyanobacteria Constructs expressing cyanobacterial BicA bicarbonate transporter analogous to those described above for SbtA were created in pEG100 (See FIG. 1 and FIG. 3).

These constructs ("pEG100 BicA_cMyc") were transformed into *Camelina sativa* by *Agrobacterium*-mediated, floral dip transformation based on established methods. 45-50 plants for each vector were transformed, and seed from the T0 plants was collected. The T1 seedlings from these plants were screened using the BASTA (glufosinate ammonium) selectable marker present in the T-DNA insertion as described above. T1 transformed plants were confirmed by PCR of genomic DNA (FIG. 5D). *Camelina* chloroplasts were isolated from a line expressing BicA from the atTic20TP_BicA_cMyc construct. After fractionating the chloroplasts, immunoblot experiments with anti-cMyc antibodies showed that the transgenic protein is localized to chloroplasts, processed to its mature form, and associated with chloroplast membranes (FIG. 7A).

Subsequently, homozygous T3 transgenic lines for photosynthesis analysis are selected.

Generation of *Camelina* Nuclear Transformants Expressing CCP1 Bicarbonate Transporter from *Chlamydomonas*

CCP1 genes from *Chlamydomonas* are attractive alternatives to SbtA as transporters to increase chloroplast [$CO_2$]. CCP1 has been shown to increase low [$CO_2$] tolerance and should contain all plant-specific information for chloroplast targeting.

We inserted CCP1 fused to the cMyc epitope tag into the pEG100 binary vector (FIG. 3) and transformed *Camelina* plants. T1 transformants were screened using BASTA selection (see FIG. 5A-C as an example) and the genotypes confirmed by PCR (FIG. 5D).

Figure 6:
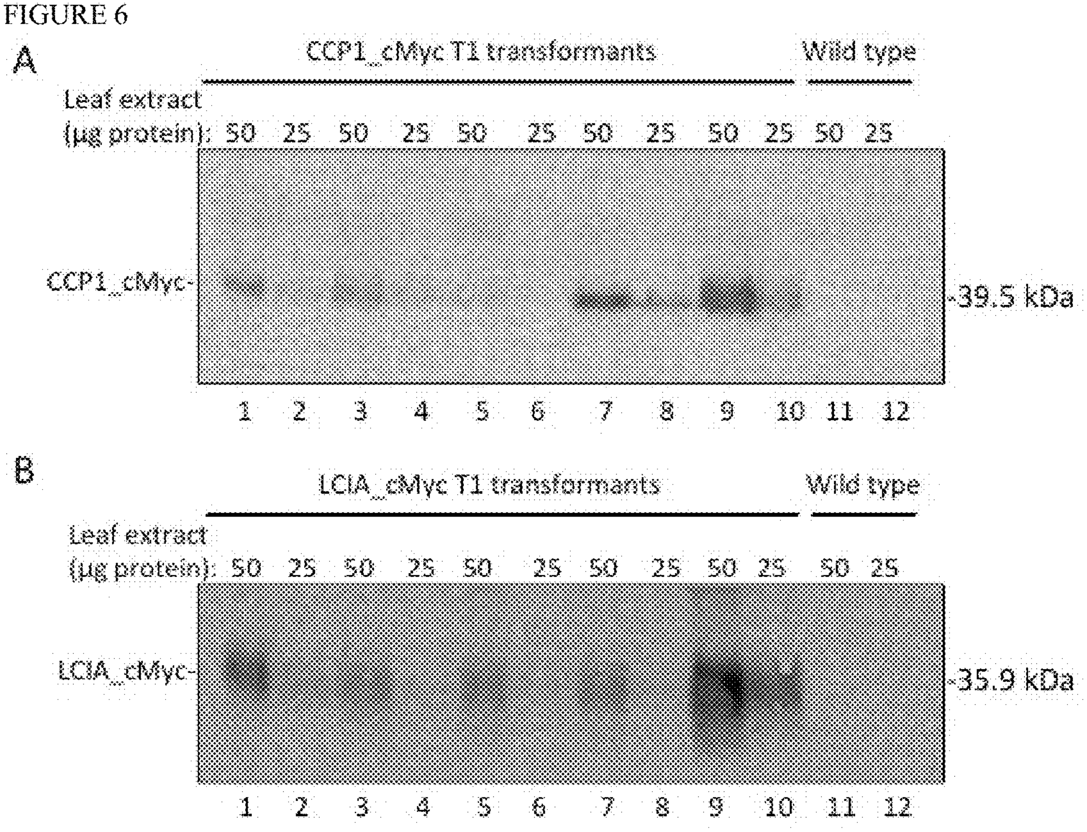
FIG. 6 shows expression of CCP1_cMyc or LCIA_cMyc in transformed *Camelina*. Leaf extracts from five-week-old T1 CCP1_cMyc transformants or T1 LCIA_cMyc transformants were resolved by SDS-PAGE and immunoblotted with anti-cMyc to detect expression of the CCP1_cMyc (A) or LCIA_cMyc (B) proteins. Proteins of the predicted molecular size were detected at varying expression levels in five independent T1 lines for each construct but not in wild type extracts.

The CCP1_cMyc lines showed a rapid pace of T1 maturation. Expression of the transgenes was tested by immunoblotting of T1 plant extracts using commercially available cMyc monoclonal antibodies. Leaf extracts were prepared from 5 randomly chosen T1 transformants and control wild type plants at 5 weeks of age (FIG. 6A). Extracts corresponding to 25 μg and 50 μg protein from each line were resolved by SDS-PAGE and immunoblotted for the presence of CCP1_cMyc. FIG. 6 demonstrates that all the T1 lines of CCP1_cMyc (FIG. 6A) examined are expressing immunoreactive proteins of the predicted molecular mass. The wild type controls do not exhibit immunoreactivity. The lines exhibit considerable variability in protein expression, providing a range of plants for phenotypic analyses of the effects of the genes on photosynthetic parameters. T2 seed from the T1 transformants was collected.

Homozygous T3 lines for the CCP1 *Camelina* lines expressing CCP1_cMyc were selected. Select homozygous lines have been analyzed for the effects of the transporter on photosynthesis ($CO_2$ assimilation), water and nitrogen use efficiency, and seed yields as described below.

Generation of *Camelina* nuclear transformants expressing LCIA from *Chlamydomonas*

Figure 3:
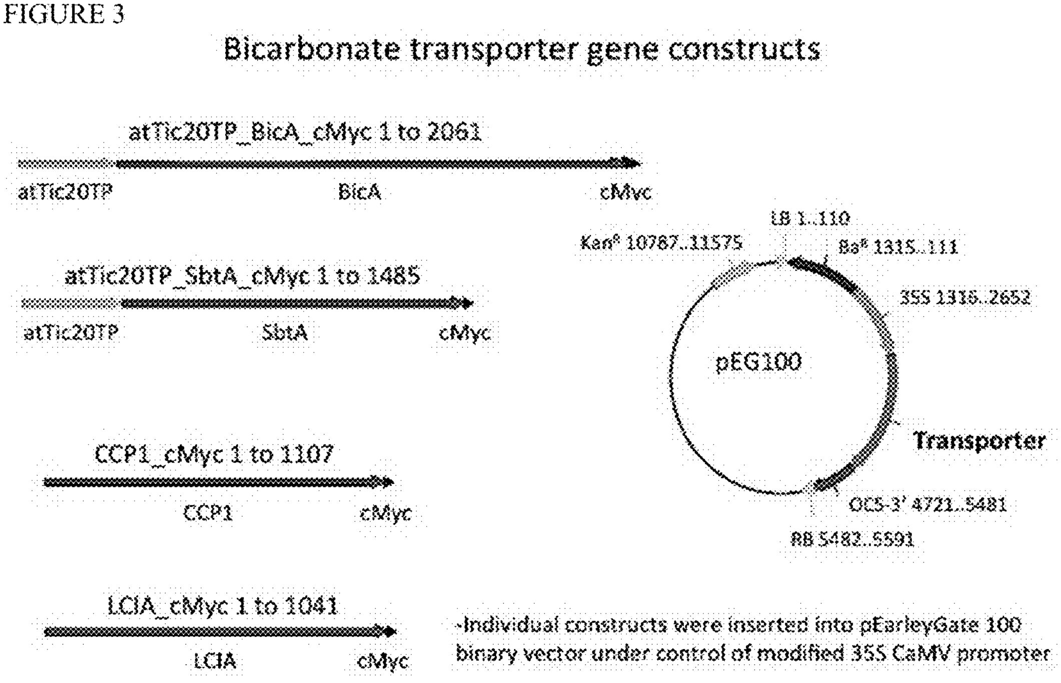
FIG. 3 shows schematic diagrams of the single gene constructs encoding atTic20TP_BicA_cMyc, atTic20TP_SbtA_cMyc, CCP1_cMyc or LCIA_cMyc that were cloned into the binary vector, pEarleyGate 100 (right), and used for nuclear transformation of *Camelina*. In these diagrams, "Kan$^R$" represents the kanamycin resistance gene; "LB" represents the T-DNA (transfer DNA) left border sequence; "Ba$^R$" represents tht BASTA resistance gene; "35S" represents the 35S Cauliflower mosaic virus promoter; "OCS" represents the octopine synthase transcriptional terminator; and "RB" represents the T-DNA right border sequence.

Constructs expressing LCIA from *Chlamydomonas* analogous to those described above for CCP1 expression were created in pEG100 (FIG. 3).

These constructs were transformed into *Camelina sativa* by *Agrobacterium*-mediated, floral dip transformation based on established methods. 45-50 plants for each vector were transformed. Seed from the T0 plants was collected.

T1 transformants were screened using BASTA selection (see FIG. 5A-C as an example) and the genotypes confirmed by PCR (FIG. 5D). Homozygous T3 lines for the LCIA *Camelina* lines expressing the individual LCIA gene from *Chlamydomonas* are selected and subsequently analyzed for various functions.

Expression of the transgenes was tested by immunoblotting of T1 plant extracts using commercially available cMyc monoclonal antibodies. Leaf extracts were prepared from 5 randomly chosen T1 transformants and control wild type plants at 5 weeks of age (FIG. 6B). Extracts corresponding to 25 μg and 50 μg protein from each line were resolved by SDS-PAGE and immunoblotted for the presence of LCIA_cMyc. FIG. 6 demonstrates that all the T1 lines of LCIA_cMyc (FIG. 6B) examined are expressing immunoreactive proteins of the predicted molecular mass. The wild type controls do not exhibit immunoreactivity.

Generation of Stacked Constructs and Plant Transformants Expressing the Stacked Constructs In addition to the single gene expression constructs, several "stacked" expression constructs were generated in which multiple bicarbonate transporter genes were expressed. Construction was analogous to that described above for the cyanobacterial transporters or the *chlamydomonas* transporters, as appropriate for the particular genes being "stacked" in the expression vectors for transformation into plants.

In particular, stacked gene constructs expressing both BicA and SbtA from cyanobacteria were made and subsequently transformed into *Camelina sativa.*

Additionally, stacked gene constructs expressing both CCP1 and LCIA from *Chlamydomonas* were made and subsequently transformed into *Camelina sativa.*

The T3 plant generation from each stacked construct has been isolated and tested A summary of the status of relevant *Camelina* transgenic lines is provided in the table below.

TABLE 5

Summary of individual and co-expressed bicarbonate transporter transgenic lines.

| | Transformant (Construct) | Expression cassettes | Generation | # of independent lines selected for further study | Confirmation of expression | Genotype |
|---|---|---|---|---|---|---|
| Single gene constructs | $Camelina^{BicA}$ (atTic20TP_BicA_cMyc) | CaMV35S prom, $Ba^r$, OCS term | T3 | 10 | YES Immuno-blotting | Homozygous |
| | $Camelina^{SbtA}$ (atTic20TP_SbtA_cMyc) | CaMV35S prom, $Ba^r$, OCS term | T3 | 10 | YES Immuno-blotting | Homozygous |
| | $Camelina^{LCIA}$ (LCIA_cMyc) | CaMV35S prom, Bar, OCS term | T3 | 10 | YES Immuno-blotting | Homozygous |
| | $Camelina^{CCP1}$ (CCP1_cMyc) | CaMV35S prom, Bar, OCS term | T3 | 10 | YES Immuno-blotting | Homozygous |
| Stacked gene constructs | $Camelina^{BicA:SbtA}$ (atTic20TP_BicA_cMyc + atTic20TP_SbtA_cMyc) | RCA prom, $Hyg^r$, dsRed, Nos/Act term Stacked genes | T3 | 10 | YES RT-PCR and Immuno-blotting | Homozygous |
| | $Camelina^{CCP1:LCIA}$ (CCP1_cMyc + LCIA_cMyc) | RCA prom, $Hyg^r$, dsRed, Nos/Act term Stacked genes | T3 | 10 | YES RT-PCR and Immuno-blotting | Homozygous |

Example 2

Functional Testing of Plant Transformants

Photosynthetic Parameters in CCP1 *Camelina* Transgenic Lines and Wild Type Plants Grown Under Identical Conditions.

Four homozygous T3 lines each of the individual CCP1 *Camelina* transformants were examined to determine their detailed photosynthetic and bicarbonate transport properties. All measurements were performed on a minimum of three biological replicates (three plants) for each line. We did identify significant differences in several CCP1 *Camelina* lines compared to wild type plants.

Net photosynthesis, intercellular $CO_2$ ($C_i$), stomatal conductance, and transpiration were measured using a portable photosynthesis system with a 3 cm×2 cm sampling chamber (LI-6400XT, Li-COR Inc., Lincoln, Nebr., USA). Gas exchange was measured on 4-5 week old plants before flowering.

Figure 8:
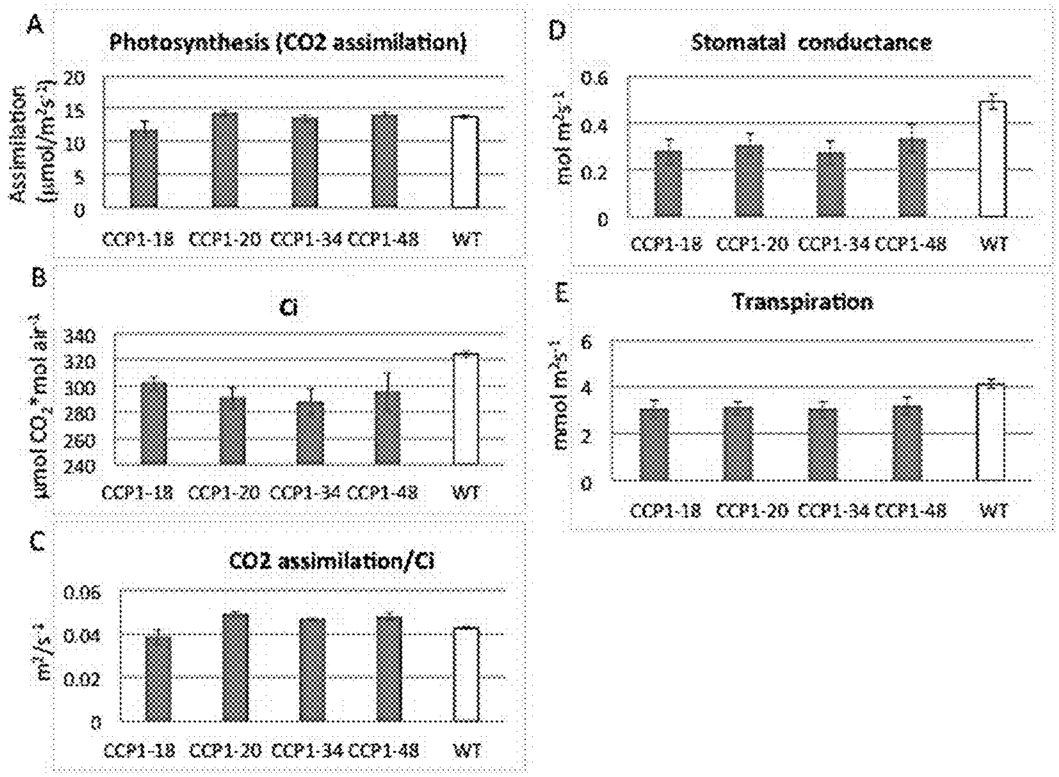
FIG. 8 shows graphs of in planta $CO_2$ assimilation, substomatal $CO_2$ concentration, stomatal conductance, and transpiration in *Camelina* T3 homozygous lines expressing CCP1_cMyc. (A) $CO_2$ assimilation at constant 400 μmol/m$^2$ atmospheric $CO_2$ and constant light. (B) substomatal $CO_2$ concentration, Ci, of plants in A, (C) Ratio of $CO_2$ assimilation from A to the Ci from B. (D) Stomatal conductance of leaves from A. (E) Transpiration rate of leaves from A at constant 50% humidity. The error bars represent standard error of the mean.

At constant $CO_2$ concentration of 400 μmol/$m^2$ (average $C_i$ of 213 μmol/$m^2$), we observed minimal differences in assimilation rates for the CCP1 *Camelina* in planta (FIG. 8A). However, we observed significant differences in the $C_i$ (FIG. 8B), stomatal conductance (FIG. 8D), and transpiration rates (FIG. 8E) of individual CCP1 *Camelina* lines compared with wild type. Stomatal conductance decreased between 27-32%, and transpiration decreased by 30-31% in the transgenic lines compared to wild type plants. When the assimilation rates were corrected for $C_i$, lines CCP1-20, CCP1-34, and CCP1-48 exhibited assimilation/Ci increases of 19%, 14%, and 17%, respectively (FIG. 8C).

These data suggest these transgenic plants are responding to higher $CO_2$ transport capacity by decreasing transpiration and gas exchange (i.e. closing stomata).

Water Use Efficiency (WUE) and Nitrogen Use Efficiency (NUE)

Based on the significantly decreased stomatal conductance and transpiration observed for CCP1 *Camelina* transgenic plants (FIG. 8), we set up a phenotypic test to compare CCP1-20 and wild type plants with respect to water use efficiency. The rationale is based on the expectation that decreased transpiration would lead to decreased water use and increased tolerance to reduced irrigation.

Figure 9:
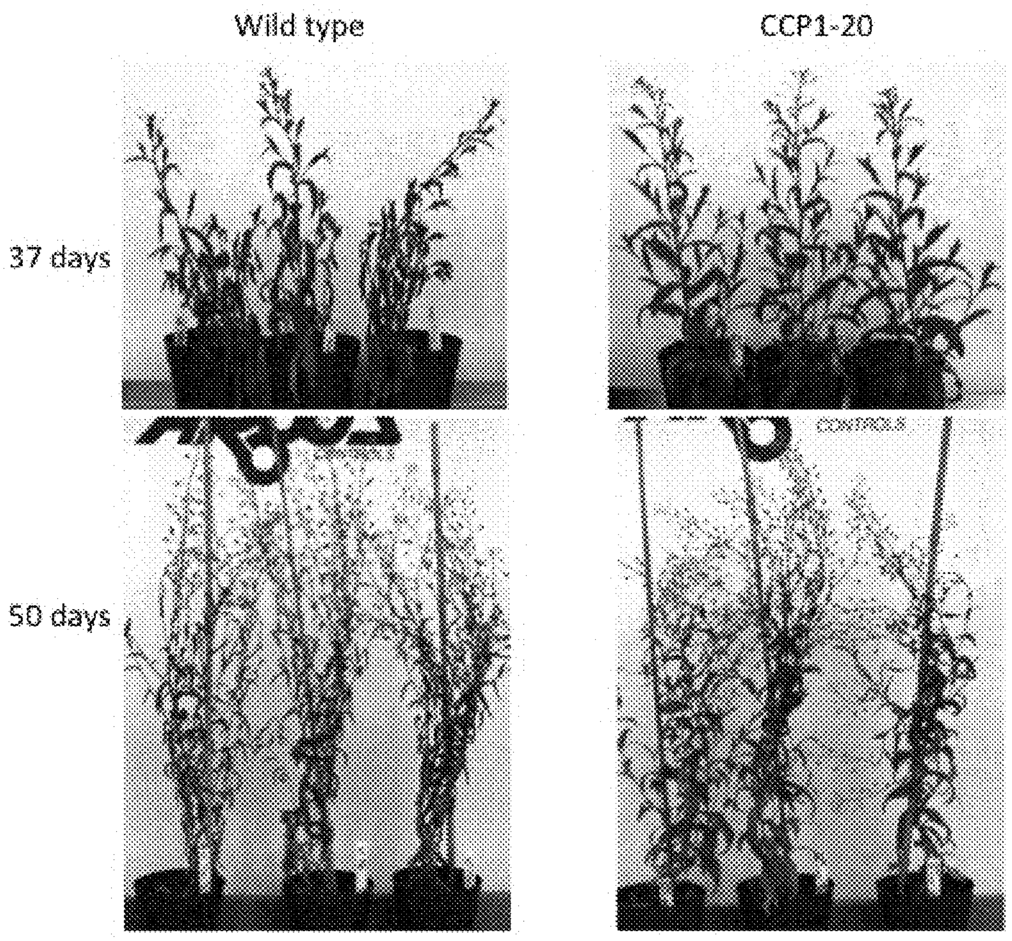
FIG. 9 show photographs of 37 and 50 day-old *Camelina* CCP1-20 plants compared to wild type (Wild type) plants when water is withheld over a 7-day period.

Transgenic and WT seedlings were germinated on Pro-mix growth medium and two weeks old seedlings were transplanted to 5" pots. As a first qualitative measure of WUE, we grew CCP1-20 and wild type plants to the stage of flower initiation (37 days) or the initiation of seed maturation (50 days) and completely withheld watering for 7 days, with daily observation for symptoms of wilting. CCP1-20 exhibited a marked increase in drought tolerance at both stages (FIG. 9). CCP1-20 plants remained healthy, whereas wild type plants were wilted and began drying after 7 days of water deprivation.

The water use efficiency (WUE) and nitrogen use efficiency (NUE) of these plants was examined to test the hypotheses that increased $CO_2$ assimilation would result in changes in gas exchange as a consequence of lower $CO_2$ demand and a decrease in nitrogen demand as a consequence of reduced rubisco synthesis.

Figure 10:
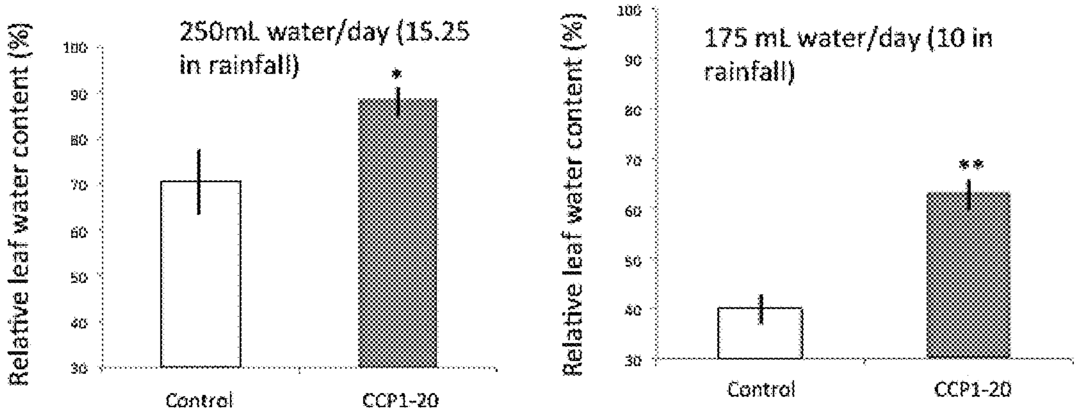
FIG. 10 shows graphs of leaf water content under limiting conditions in *Camelina* CCP1-20 and wild type (control) plants watered at 250 ml/day or 175 ml/day. Watering values correspond to typical range of field values. The symbols ** and * indicate significance at P=0.01 and P=0.05 in a two tailed t-test, respectively.

WUE was measured quantitatively by determining the leaf water content of wild type and CCP1-20 plants, which were grown under a defined water regimen. Relative leaf water content was measured on leaves of equal size as described in Barrs (Australian Journal of Biological Sciences, 1962, 15:413-428). Water content between WT and CCP1-20 were not significantly different under standard green house conditions. Differences in water content were detectable at ≤250 ml/day water. FIG. 10 shows the leaf water content at 250 ml/day and 175 ml/day water. These values were chosen because they correspond to ~15 in and ~10 in rainfall amounts during the growing season, respectively (*Spring Camelina Production Guide* 2009). Field trials of WT plants demonstrate a 50% increase in yields when rainfall increased from 10 to 15 in/season (*Spring Camelina Production Guide* 2009). CCP1-20 plants exhibited a 25% and 71% increase in water content relative to WT at 250 ml/day and 175 ml/day water, respectively. The water content at 175 ml/day was only 27% below that observed under standard greenhouse conditions. These data demonstrate a significant increase in WUE by CCP1-20 plants.

Figure 11:
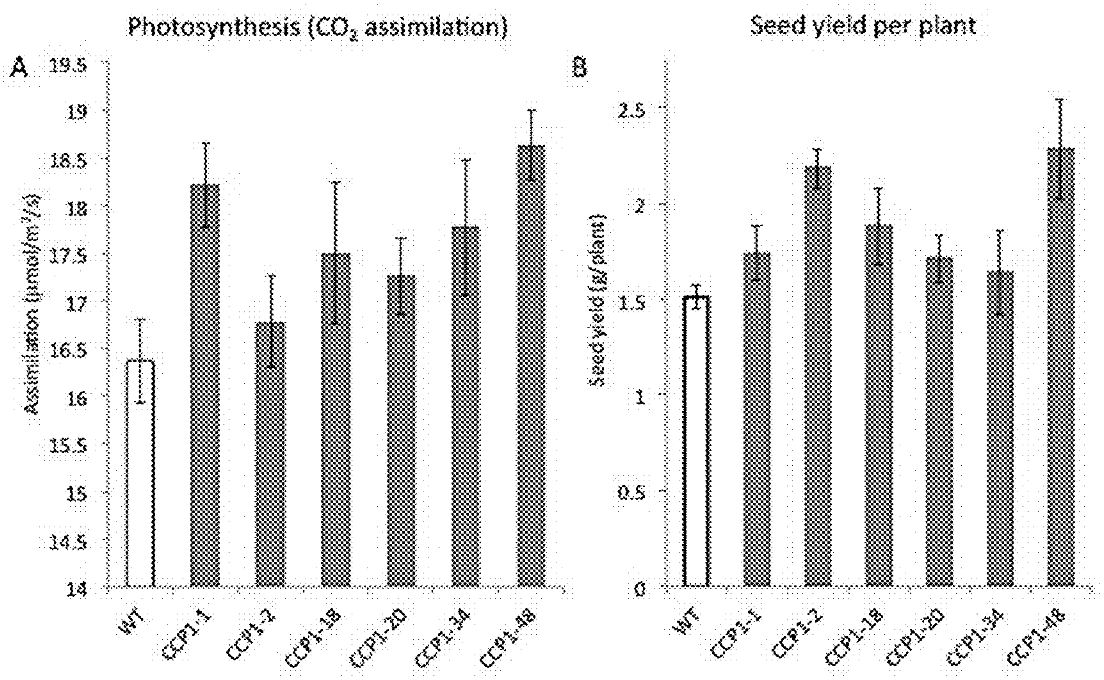
FIG. 11 shows graphs of $CO_2$ assimilation rates (A) and seed yields (B) for representative CCP1 *Camelina* lines under limiting water treatments. Seed yields were quantified as seed weight per plant.

Measurement of $CO_2$ assimilation at constant atmospheric $[CO_2]$ in a larger representative set of CCP1 lines under water limiting conditions, shows increases in assimilation between 2-14% relative to wild type plants (FIG. 11A). Seed yields in CCP1 *Camelina* plants, as measured by seed weight per plant, increased between 7-50% in all lines under these conditions, except CCP1-34 (FIG. 11B). No significant differences in oil content of seed were detected in the all CCP1 transgenic lines compared to wild type plants (data not shown).

Figure 12:
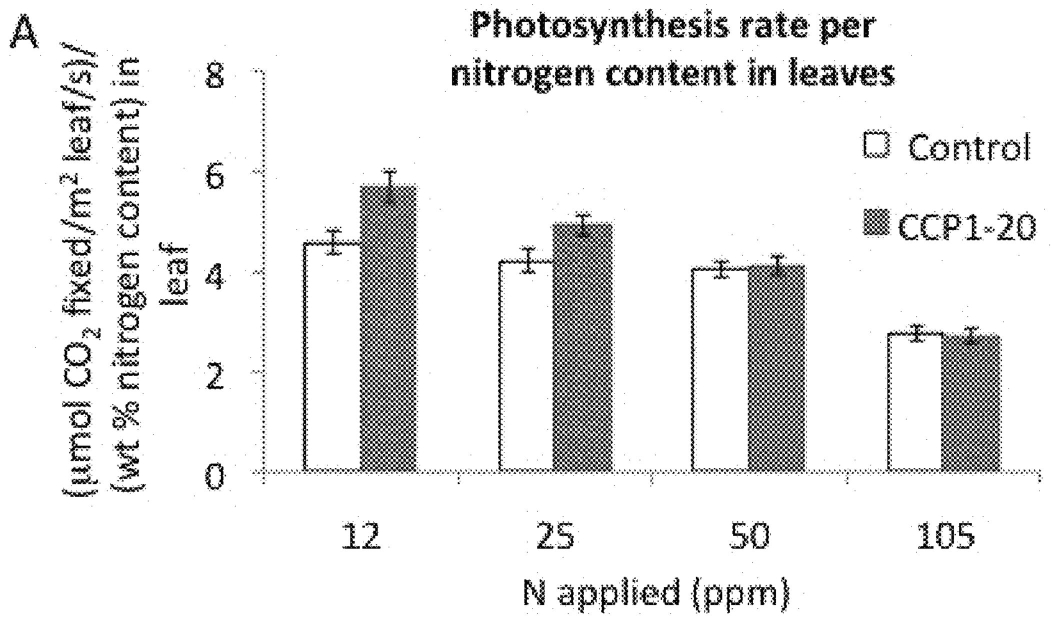
FIG. 12 shows graphs of nitrogen use efficiency (A) and carbon/nitrogen ratio (B) for CCP1-20 and wild type (Control) plants under varying nitrogen fertilizer applications.
Figure 12:
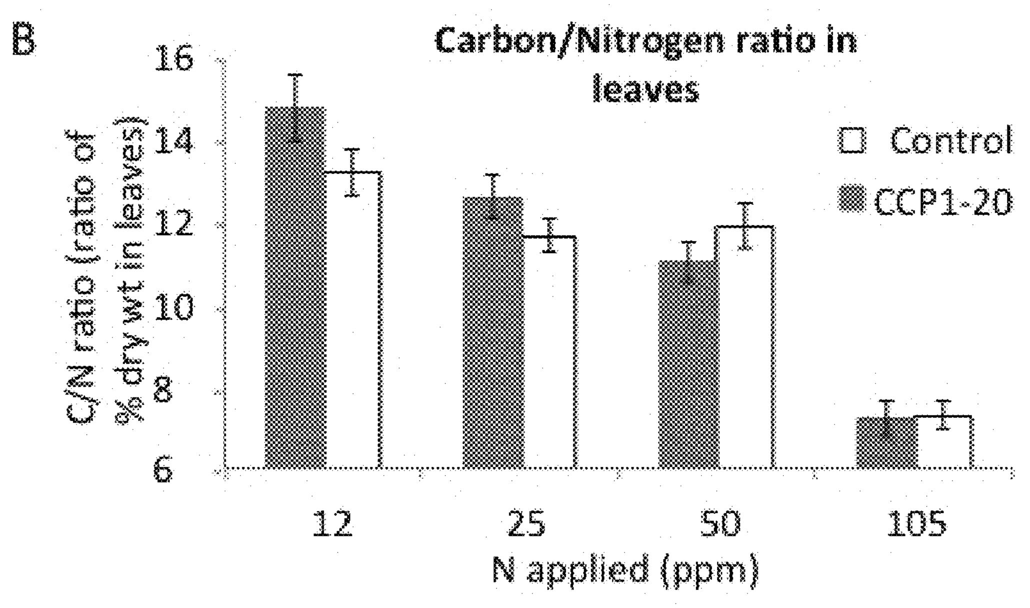

Nitrogen use efficiency (NUE) was measured using two parameters (FIG. 12). First, $CO_2$ assimilation rates were measured as a function of leaf nitrogen content (FIG. 12A). Two weeks old WT and transgenic plants were transplanted to 5' pots filled with vermiculite. The plants were treated with Hoagland's nutrient solution containing different concentrations of nitrogen as indicated. Net photosynthesis was measured on mature leaves of 4 weeks old plants. Then the leaves were harvested, dried and the total nitrogen content was determined by catalytic combustion. CCP1-20 exhibited a 29% increase in NUE at 12 ppm nitrogen fertilization application compared to wild type. The difference in NUE between CCP1-20 and wild type plants decreased to 19% at 25 ppm nitrogen and was indistinguishable at higher nitrogen applications. 12 ppm and 25 ppm nitrogen correspond to field applications of 24 lb/acre and 50 lb/acre in soil, respectively. The recommended application rate in the field is 30 lb/acre (*Spring Camelina Production Guide* 2009). A 15% difference in the carbon/nitrogen content ratio was observed between CCP1-20 and wild type at 12 ppm nitrogen (FIG. 12B), consistent with the increase NUE in CCP1-20. Our standard greenhouse application is ~200 ppm nitrogen. These data demonstrate that CCP1-20 exhibits a significant increase in NUE relative to wild type plants. The difference is most apparent under conditions that attempt to mimic field conditions.

Figure 13:
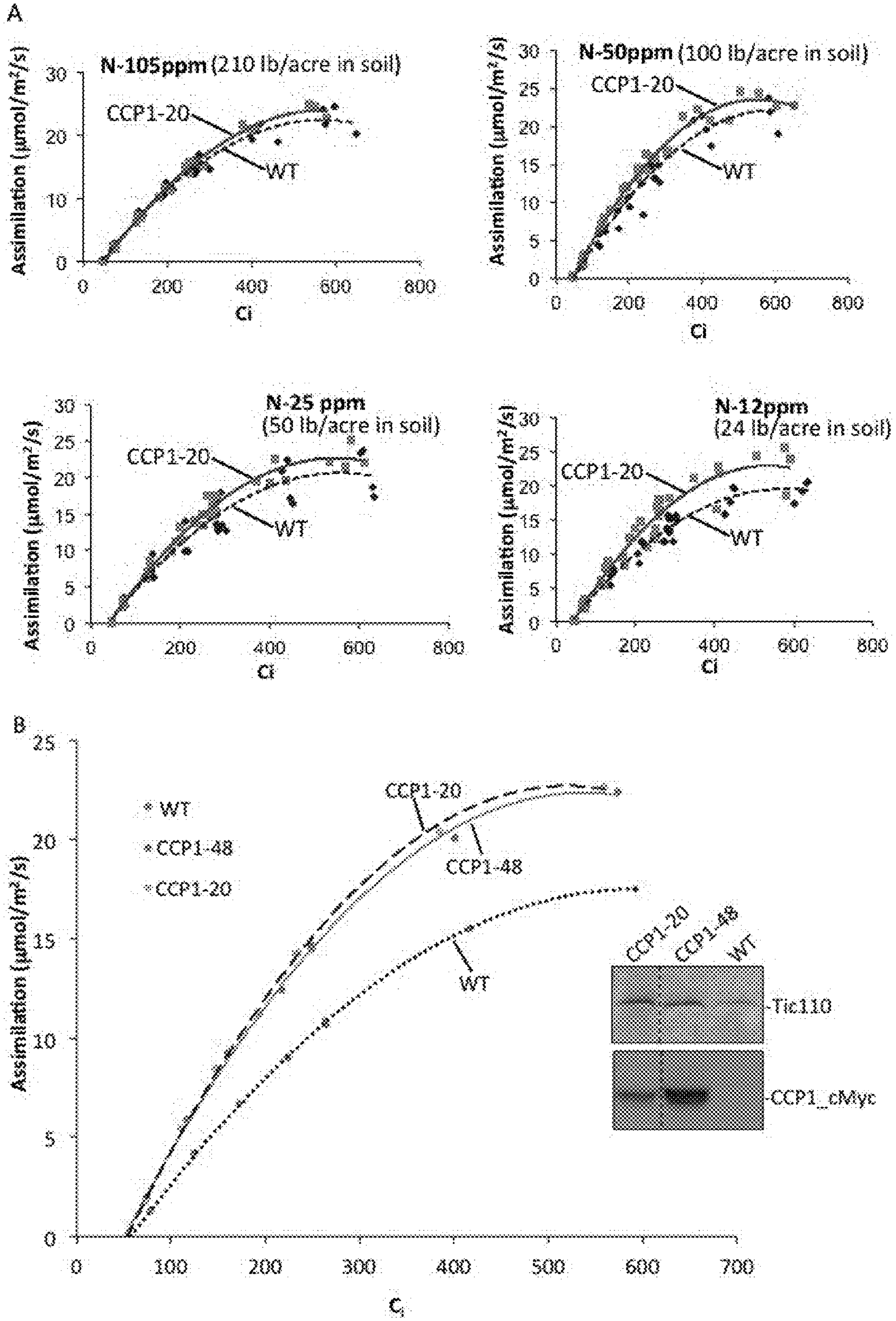
FIG. 13 shows A/$C_i$ curves of wild type (WT) *Camelina* and T3 homozygous CCP1 *Camelina* grown under varying nitrogen. (A) A/$C_i$ (net $CO_2$ assimilation rate, A, versus calculated substomatal $CO_2$ concentration, Ci) curves for *Camelina* line CCP1-20 and wild type plants grown under varying nitrogen fertilizer rates as indicated. (B) A/Ci curves for WT *Camelina* and two independent homozygous CCP1_cMyc transformed lines expressing CCP1_cMyc. The best fit trend line is shown for each scatter plot. Expression levels of CCP1_cMyc in the two lines are shown in the inset.

We also analyzed photosynthetic parameters in wild type and CCP1-20 plants grown under varying nitrogen fertilizer applications using an $A/C_i$ curve (net $CO_2$ assimilation rate, A, versus calculated substomatal $CO_2$ concentration, Ci). Measurements were performed in planta with the LI-6400XT. The $CO_2$ assimilation rate remained nearly constant for CCP1-20 at all nitrogen concentrations, but decreased for wild type at nitrogen concentrations below 50 ppm (FIG. 13A). At 25 and 12 ppm nitrogen, the CCP1-20 plants exhibited 21% and 35% higher assimilation rate compared to wild type plants, respectively (FIG. 13A). We also generated an A/Ci curve at 12 ppm nitrogen fertilization for a second line, CCP1-48, to support the increased nitrogen use efficiency observed with CCP1-20. Both lines (CCP1-20 and CCP1-48) showed similar A/Ci curves, with 30% increases in $CO_2$ assimilation rate relative to wild type plants observed at 400 ppm $C_i$ (FIG. 13B).

Figure 14:
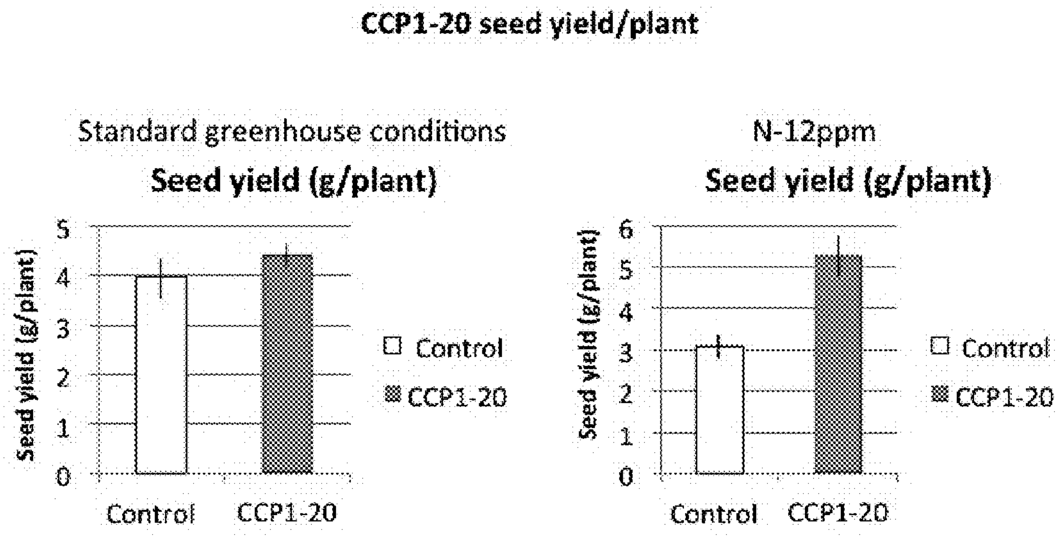
FIG. 14 shows graphs of seed yields from CCP1-20 *Camelina* and wild type (Control) plants grown under nitrogen sufficient (≥100 ppm nitrogen; labeled "standard greenhouse conditions") or reduced nitrogen (12 ppm nitrogen). Seed yields were measured as total seed weight per plant. Each sample represents the average of a minimum of 10 plants. The error bars represent standard error of the mean.

The increased NUE at lower nitrogen fertilizer applications translated into a significant increase in seed yield. CCP1-20 seed yields (seed wt/plant) were 56% higher than wild type at 12 ppm nitrogen (FIG. 14). No significant differences in seed yield between wild type and CCP1-20 were observed under standard greenhouse fertilizer conditions (≥100 ppm N)(FIG. 14).

Biomass and Seed Yields of CCP1 Transgenic Lines in Field Trials in Western Massachusetts Representative CCP1 *Camelina* lines CCP11-18, CCP1-20, and CCP1-48 were tested in field trials in western Massachusetts using 25 sq. ft. plots. Planting was initiated on May 23. Harvest of the CCP1 *Camelina* lines was initiated on July 29 and completed on August 11. Harvest of the wild type control plots was initiated on August 4 and completed on August 25.

Figure 15:
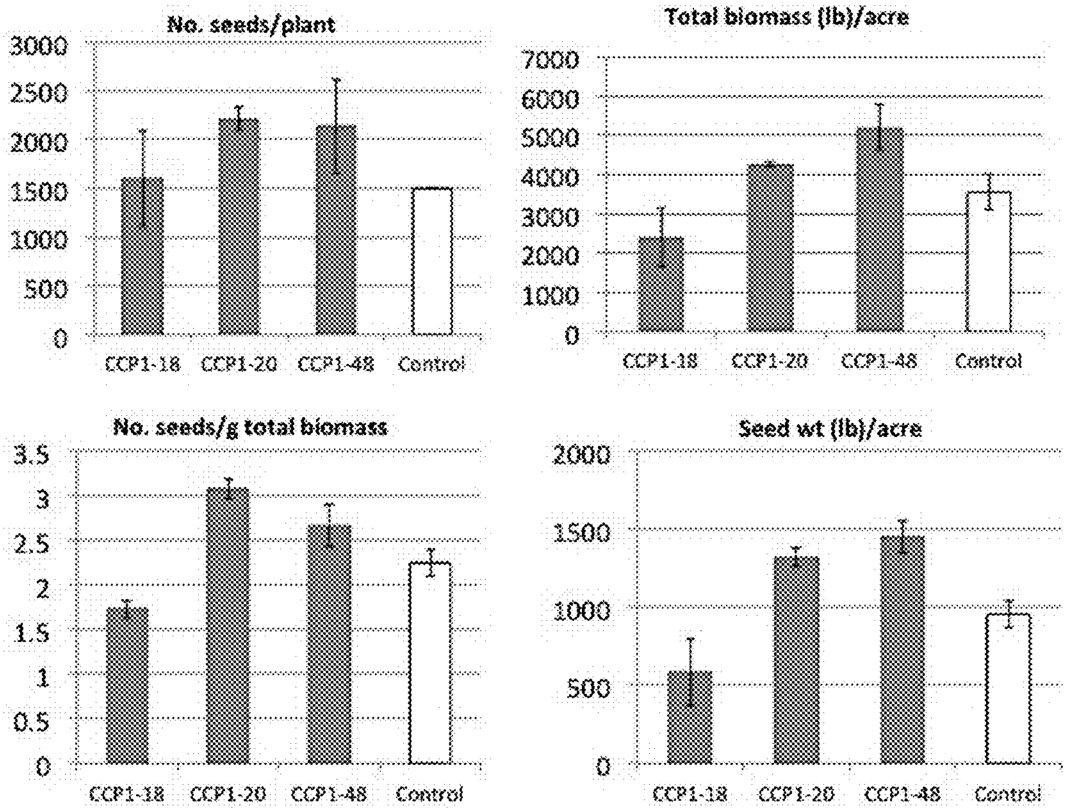
FIG. 15 presents biomass yield data from the field test of the CCP1 *Camelina* lines relative to the wild type (Control) plants.

The CCP1-20 and CCP1-48 lines consistently exhibited higher biomass yields, including higher numbers of seeds per plant, number of seeds per total biomass, and total seed and biomass weights per acre (FIG. 15). The increases were consistent with observations in the green house and growth chambers for both of these lines. The seed weight per acre increased by 38% and 51.5% in CCP1-20 and CCP1-48, respectively. The CCP1-18 line significantly underperformed in the field due to low seedling establishment, and showed a 39% decrease in seed wt per acre.

Figure 16:
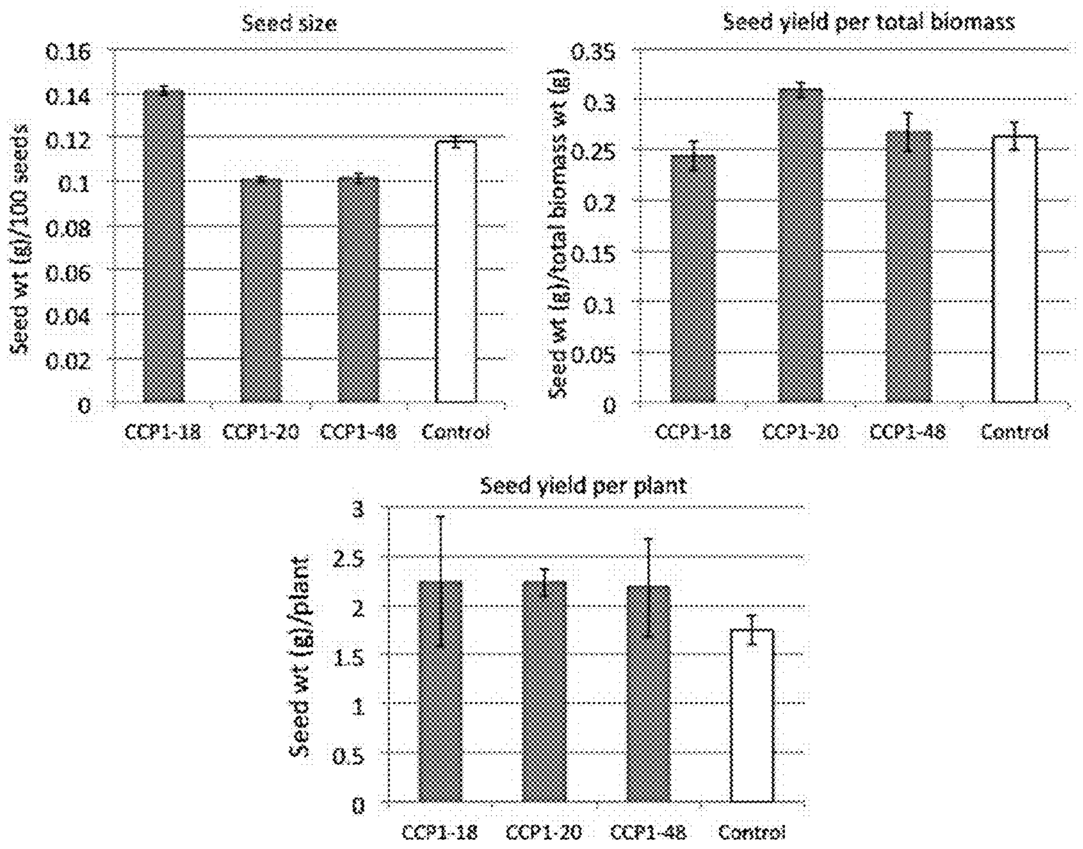
FIG. 16 presents seed yield data from the field test of the bicarbonate transporter lines relative to the wild type (Control) plants.

CCP1-20, and CCP1-48 exhibited slightly reduced seed sizes (seed wt/100 seeds) (FIG. 16), demonstrating that the overall increase in seed yields was due largely to an increase in the number of seeds produced per plant. These data also are consistent with green house studies.

Figure 17:
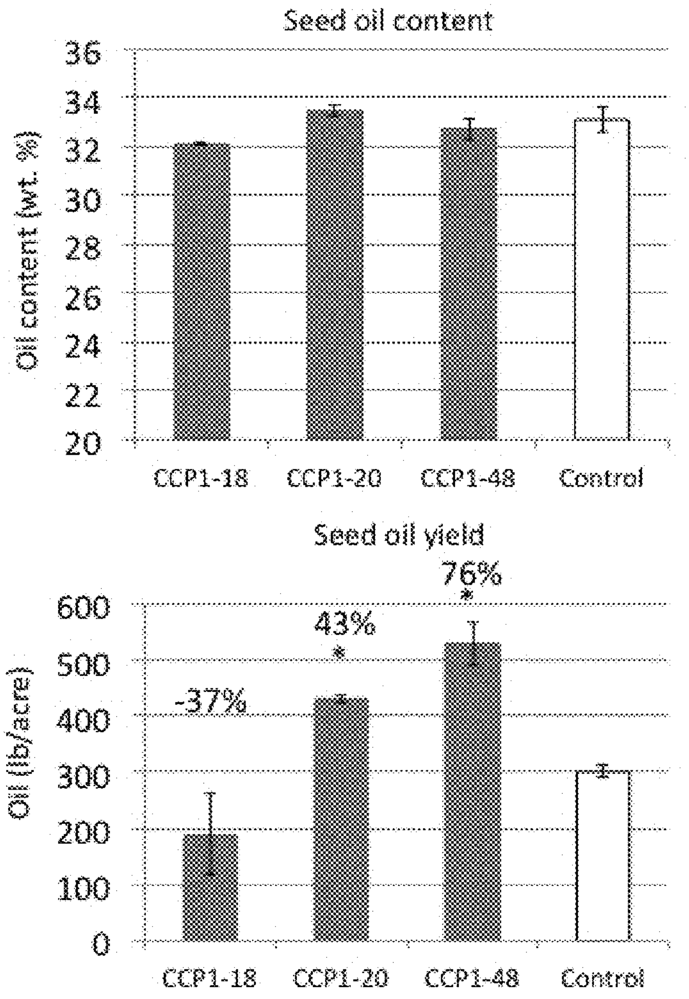
FIG. 17 presents oil yield data from the field test of the bicarbonate transporter lines relative to the wild type (Control) plants. The symbol * indicates significance at P=0.05 in a t-test for two samples assuming unequal variances.

Oil content of the seeds for all of the transgenics was indistinguishable from wild type controls, with content ranging from 32-34% (wt/wt) oil (FIG. 17). The overall oil yield (lb./acre) increased by 43% and 76%, in CCP1-20 and CCP1-48, respectively. Consistent with its underperformance, line CCP1-48 showed a 37% decrease in oil yield.

As demonstrated by the planting and harvesting schedules for the field trials, lines expressing the CCP1 construct matured one to two weeks ahead of control lines. This suggests that this trait also might influence the life cycle of *Camelina* and/or induce early senescence in the transgenic plants.

Photosynthetic Parameters in SbtA or BicA Transgenic Lines and Wild Type Plants Grown Under Identical Conditions.

Figure 18:
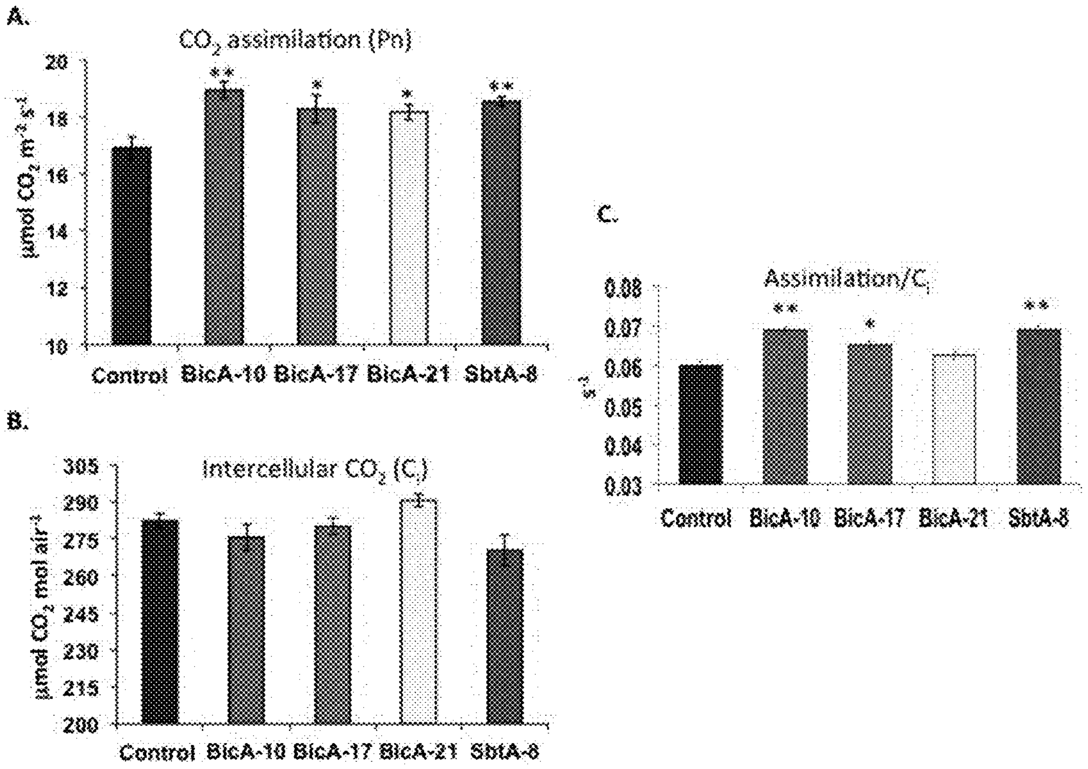
FIG. 18 presents graphs of in planta $CO_2$ assimilation and internal [$CO_2$] in BicA or SbtA *Camelina* T3 homozygous lines and wild type (Control) plants. A. $CO_2$ assimilation at constant 400 μmol/$m^2$ atmospheric $CO_2$ and constant light. B. Substomatal $CO_2$ ($C_i$) in transgenic lines. C. Ratio of $CO_2$ assimilation to Ci. Light levels are 600 μmol $m^{-2}$ $s^{-1}$. Plants were grown in 2 gal pots. Measurements were taken on 5 week old plants. The error bars represent standard error of the mean. ** and * indicate significance at P=0.01 and P=0.05 in two tailed t test, respectively.

We also analyzed photosynthetic parameters in homozygous *Camelina* BicA and SbtA T3 homozygous lines expressing the BicA and SbtA microbial bicarbonate transporters. Several lines exhibited significantly increased $CO_2$ assimilation (FIG. 18A). When adjusted from $C_i$ (FIG. 18B), SbtA-8 and BicA-10 exhibited statistically significant increases in assimilation of 15% compared to wild type plants (FIG. 18C) at constant $C_i$ of 275 $\mu$mol $CO_2$ mol $air^{-1}$.

Example 3

Transforming Various Crops with the Vectors

*Agrobacterium*-Mediated Transformation of Maize

The vectors provided in the invention can be used for *Agrobacterium*-mediated transformation of maize following a previously described procedure (Frame et al., 2006, *Agrobacterium* Protocols Wang K., ed., Vol. 1, pp 185-199, Humana Press).

Plant material: Plants grown in a greenhouse are used as an explant source. Ears are harvested 9-13 d after pollination and surface sterilized with 80% ethanol.

Explant isolation, infection and co-cultivation: Immature zygotic embryos (1.2-2.0 mm) are aseptically dissected from individual kernels and incubated in *A. tumefaciens* strain EHA101 culture (grown in 5 ml N6 medium supplemented with 100 μM acetosyringone for stimulation of the bacterial vir genes for 2-5 h prior to transformation) at room temperature for 5 min. The infected embryos are transferred scutellum side up on to a co-cultivation medium (N6 agar-solidified medium containing 300 mg/l cysteine, 5 μM silver nitrate and 100 μM acetosyringone) and incubated at 20° C., in the dark for 3 d. Embryos are transferred to N6 resting medium containing 100 mg/l cefotaxime, 100 mg/l vancomycin and 5 μM silver nitrate and incubated at 28° C., in the dark for 7 d.

Callus selection: All embryos are transferred on to the first selection medium (the resting medium described above supplemented with 1.5 mg/l bialaphos) and incubated at 28° C., in the dark for 2 weeks followed by subculture on a selection medium containing 3 mg/l bialaphos. Proliferating pieces of callus are propagated and maintained by subculture on the same medium every 2 weeks.

Plant regeneration and selection: Bialaphos-resistant embryogenic callus lines are transferred on to regeneration medium I (MS basal medium supplemented with 60 g/l sucrose, 1.5 mg/l bialaphos and 100 mg/l cefotaxime and solidified with 3 g/l Gelrite) and incubated at 25° C., in the dark for 2 to 3 weeks. Mature embryos formed during this period are transferred on to regeneration medium II (the same as regeneration medium I with 3 mg/l bialaphos) for germination in the light (25° C., 80-100 $\mu E/m^2/s$ light intensity, 16/8-h photoperiod). Regenerated plants are ready for transfer to soil within 10-14 days.

*Agrobacterium*-Mediated Transformation of *Sorghum*

The vectors provided in the invention can be used for *sorghum* transformation following a previously described procedure (Zhao, 2006, *Agrobacterium* Protocols Wang K., ed., Vol. 1, pp 233-244, Humana Press).

Plant material: Plants grown under greenhouse, growth chamber or field conditions are used as an explant source. Immature panicles are harvested 9-12 d post pollination and individual kernels are surface sterilized with 50% bleach for 30 min followed by three washes with sterile distilled water.

Explant isolation, infection and co-cultivation: Immature zygotic embryos (1-1.5 mm) are aseptically dissected from individual kernels and incubated in *A. tumefaciens* strain LBA4404 suspension in PHI-I liquid medium (MS basal medium supplemented with 1 g/l casamino acids, 1.5 mg/l 2,4-D, 68.5 g/l sucrose, 36 g/l glucose and 100 μM acetosyringone) at room temperature for 5 min. The infected embryos are transferred with embryonic axis down on to a co-cultivation PHI-T medium (agar-solidified modified PHI-I medium containing 2.0 mg/l 2,4-D, 20 g/l sucrose, 10 g/l glucose, 0.5 g/l MES, 0.7 g/l proline, 10 mg/l ascorbic acid and 100 μM acetosyringone) and incubated at 25° C., in the dark for 3 d. For resting, embryos are transferred to the same medium (without acetosyringone) supplemented with 100 mg/l carbenicillin and incubated at 28° C., in the dark for 4 d.

Callus selection: Embryos are transferred on to the first selection medium PHI-U (PHI-T medium described above supplemented with 1.5 mg/l 2,4-D, 100 mg/l carbenicillin and 5 mg/l PPT without glucose and acetosyringone) and incubated at 28° C., in the dark for 2 weeks followed by subculture on a selection medium containing 10 mg/l PPT. Proliferating pieces of callus are propagated and maintained by subculture on the same medium every 2 weeks for the remainder of the callus selection process of 10 weeks.

Plant regeneration and selection: Herbicide-resistant callus is transferred on to regeneration medium I (PHI-U medium supplemented with 0.5 mg/l kinetin) and incubated at 28° C., in the dark for 2 to 3 weeks for callus growth and embryo development. Cultures are transferred on to regeneration medium II (MS basal medium with 0.5 mg/l zeatin, 700 mg/l proline, 60 g/l sucrose and 100 mg/l carbenicillin) for shoot formation (28° C., in the dark). After 2-3 weeks, shoots are transferred on to a rooting medium (regeneration II medium supplemented with 20 g/l sucrose, 0.5 mg/l NAA and 0.5 mg/l IBA) and grown at 25° C., 270 $\mu E/m^2/s$ light intensity with a 16/8-h photoperiod. When the regenerated plants are 8-10 cm tall, they can be transferred to soil and grown under greenhouse conditions.

*Agrobacterium*-Mediated Transformation of Rice

The vectors provided in the invention can be used for *Agrobacterium*-mediated transformation of rice following a previously described procedure (Herve and Kayano, 2006, *Agrobacterium* Protocols Wang K., ed., Vol. 1, pp 213-222, Humana Press).

Plant material: Mature seeds from *japonica* rice varieties grown in a greenhouse are used as an explant source.

Culture transformation and selection: Dehusked seeds are surface sterilized with 70% ethanol for 1 min and 3% sodium hypochlorite for 30 min followed by six washes with sterile distilled water. Seeds are plated embryo side up on an induction medium (Gelrite-solidified N6 basal medium supplemented with 300 mg/l casamino acids, 2.88 g/l proline, 30 g/l sucrose and 2 mg/l 2,4-D) and incubated at 32° C., under continuous light for 5 d. Germinated seeds with swelling of the scutellum are infected with *A. tumefaciens* strain LBA4404 (culture from 3-d-old plates resuspended in N6 medium supplemented with 100 μM acetosyringone, 68.5 g/l sucrose and 36 g/l glucose) at room temperature for 2 min followed by transfer on to a co-cultivation medium (N6 Gelrite-solidified medium containing 300 mg/l casamino acids, 30 g/l sucrose, 10 g/l glucose, 2 mg/l 2,4-D and 100 μM acetosyringone) and incubation at 25° C., in the dark for 3 d.

For selection of transformed embryogenic tissues, whole seedlings washed with 250 mg/l cephotaxine are transferred on to N6 agar-solidified medium containing 300 mg/l casamino acids, 2.88 g/l pro line, 30 g/l sucrose, 2 mg/l 2,4-D, 100 mg/l cefotaxime, 100 mg/l vancomycin and 35 mg/l G418 disulfate). Cultures are incubated at 32° C., under continuous light for 2-3 weeks.

Plant regeneration and selection: Resistant proliferating calluses are transferred on to agar-solidified N6 medium containing 300 mg/l casamino acids, 500 mg/l proline, 30 g/l sucrose, 1 mg/l NAA, 5 mg/l ABA, 2 mg/l kinetin, 100 mg/l cefotaxime, 100 mg/l vancomycin and 20 mg/l G418 disulfate. After one week of growth at 32° C., under continuous light, the surviving calluses are transferred on to MS medium (solidified with 10 g/l agarose) supplemented with 2 g/l casamino acids, 30 g/l sucrose, 30 g/l sorbitol, 0.02 mg/l NAA, 2 mg/l kinetin, 100 mg/l cefotaxime, 100 mg/l vancomycin and 20 mg/l G418 disulfate and incubated under the same conditions for another week followed by a transfer on to the same medium with 7 g/l agarose. After 2 weeks, the emerging shoots are transferred on to Gelrite-solidified MS hormone-free medium containing 30 g/l sucrose and grown under continuous light for 1-2 weeks to promote shoot and root development. When the regenerated plants are 8-10 cm tall, they can be transferred to soil and grown under greenhouse conditions. After about 10-16 weeks, transgenic seeds are harvested.

Indica rice varieties are transformed with *Agrobacterium* following a similar procedure (Datta and Datta, 2006, *Agrobacterium* Protocols Wang K., ed., Vol. 1, pp 201-212, Humana Press).

Microprojectile Bombardment-Mediated Transformation of Sugarcane

An expression cassette containing a transcription factor gene can be co-introduced with a cassette of a marker gene (e. g., npt) into sugarcane via biolistics following a previously described protocol (Taparia et al., 2012, *In Vitro Cell. Dev. Biol.* 48: 15-22))

Plant material: Greenhouse-grown plants with 6-8 visible nodes are used as an explant source. Tops are collected and surface sterilized with 70% ethanol. The outermost leaves are removed under aseptic conditions and immature leaf whorl cross sections (about 2 mm) are cutfrom the region 1-10 cm above the apical node.

Culture initiation, transformation and selection: The isolated leaf sections are cultured on MS basal media supplemented with 20 g/l sucrose, 1.86 mg/l p-chlorophenoxyacetic acid (CPA), 1.86 mg/l NAA and 0.09 mg/l BA at 28° C., under 30 μmol/m$^2$/s light intensity and a 16/8-h photoperiod for 7 d. Embryogenic cultures are subcultured to fresh medium and used for transformation.

For microprojectile bombardment, leaf disks are plated on the culture initiation medium supplemented with 0.4 M sorbitol 4 hours before gene transfer. Plasmid DNA (200 ng) containing the expression cassettes of a TF and a marker gene is precipitated onto 1.8 mg gold particles (0.6 μm) following a previously described procedure (Altpeter and Sandhu, 2010, *Genetic transformation—biolistics*, Davey & Anthony eds., pp 217-237, Wiley, Hoboken). The DNA (10 ng per shot) is delivered to the explants by a PDS-1000 Biolistc particle delivery system (Biorad) using 1100-psi rupture disk, 26.5 mmHg chamber vacuum and a shelf distance of 6 cm. pressure). The bombarded expants are transferred to the culture initiation medium described above and incubated for 4 days.

For selection, cultures are transferred on to the initiation medium supplemented with 30 mg/l geneticin and incubated for 10 d followed by another selection cycle under the same conditions.

Plant regeneration and selection: Cultures are transferred on to the selection medium described above without CPA and grown at 28° C., under 100 μmol/m$^2$/s light intensity with a 16/8-h photoperiod. Leaf disks with small shoots (about 0.5 cm) are plated on a hormone-free medium with 30 mg/l geneticin for shoot growth and root development. Prior to transfer to soil, roots of regenerated plants can be dipped into a commercially available root promoting powder.

Transformation of Wheat by Microprojectile Bombardment

The gene constructs provided in the invention can be used for wheat transformation by microprojectile bombardment following a previously described protocol (Weeks et al., 1993, *Plant Physiol.* 102: 1077-1084).

Plant material: Plants from the spring wheat cultivar Bobwhite are grown at 18-20° C. day and 14-16° C. night temperatures under a 16 h photoperiod. Spikes are collected 10-12 weeks after sowing (12-16 days post anthesis). Individual caryopses at the early-medium milk stage are sterilized with 70% ethanol for 5 min and 20% sodium hypochlorite for 15 min followed by three washes with sterile water.

Culture initiation, transformation and selection: Immature zygotic embryos (0.5-1.5 mm) are dissected under aseptic conditions, placed scutellum side up on a culture induction medium (Phytagel-solidified MS medium containing 20 g/l sucrose and 1.5 mg/l 2,4-D) and incubated at 27° C., in the light (43 μmol/m$^2$/s) for 3-5 d.

For microprojectile bombardment, embryo-derived calluses are plated on the culture initiation medium supplemented with 0.4 M sorbitol 4 hours before gene transfer. Plasmid DNA containing the expression cassettes of a TF and the marker gene bar is precipitated onto 0.6-μm gold particles and delivered to the explants as described for sugarcane.

The bombarded expants are transferred to callus selection medium (the culture initiation medium described above containing 1-2 mg/l bialaphos) and subcultured every 2 weeks.

Plant regeneration and selection: After one-two selection cycles, cultures are transferred on to MS regeneration medium supplemented with 0.5 mg/l dicamba and 2 mg/l bialaphos. For root formation, the resulting bialaphos-resistant shoots are transferred to hormone-free half-strength MS medium. Plants with well-developed roots are transferred to soil and acclimated to lower humidity at 21° C. with a 16-h photoperiod (300 μmol/m$^2$/s) for about 2 weeks prior to transfer to a greenhouse.

*Agrobacterium*-Mediated Transformation of *Brassica napus*

Plant material: Mature seeds are surface sterilized in 10% commercial bleach for 30 min with gentle shaking and washed three times with sterile distilled water.

Culture initiation and transformation: Seeds are plated on germination medium (MS basal medium supplemented with 30 g/l sucrose) and incubated at 24° C. with a 16-h photoperiod at a light intensity of 60-80 μE/m$^2$/s for 4-5 d. For transformation, cotyledons with ~2 mm of the petiole at the base are excised from the resulting seedlings, immersed in *Agrobacterium tumefacians* strain EHA101 suspension (grown from a single colony in 5 ml of minimal medium supplemented with appropriate antibiotics at 28° C. for 48 h) for 1 s and immediately embedded to a depth of ~2 mm in a co-cultivation medium (MS basal medium with 30 g/l sucrose and 20 μM benzyladenine). The inoculated cotyledons are incubated under the same growth conditions for 48 h.

Plant regeneration and selection: After co-cultivation, cotyledons are transferred on to a regeneration medium comprising MS medium supplemented with 30 g/l sucrose and 20 μM benzyladenine, 300 mg/l timentinin and 20 mg/l kanamycin sulfate. After 2-3 weeks, regenerated shoots are cut and maintained on MS medium for shoot elongation containing 30 g/l sucrose, 300 mg/l timentin, and 20 mg/l kanamycin sulfate. The elongated shoots are transferred to a rooting medium comprising MS basal medium supplemented with 30 g/l sucrose, 2 mg/l indole butyric acid (IBA) and 500 mg/L carbenicillin. After root formation, plants are transferred to soil and grown to seed maturity under growth chamber or greenhouse conditions.

*Agrobacterium*-Mediated Transformation of Soybean

The soybean orthologs of the switchgrass transcription factor genes identified in the invention (FIG. 4) are assembled in binary vectors (Table 9) and used for *Agrobacterium*-mediated transformation of soybean following a previously described procedure (Ko et al., 2006, *Agrobacterium Protocols* Wang K., ed., Vol. 1, pp 397-405, Humana Press).

Plant material: Immature seeds from soybean plants grown under greenhouse or field conditions are used as an explant source. Young pods are harvested and surface sterilized with 70% 2-propanol for 30 sec and 25% Clorox for 20 min followed by three washes with sterile distilled water.

Culture transformation and selection: Under aseptic conditions, immature seeds are removed from the pods and the cotyledons are separated from the seed coat followed by incubation in *A. tumefaciens* culture (grown from a single colony at 28° C., overnight) in co-cultivation medium (MS salts and B5 vitamins) supplemented with 30 g/l sucrose, 40 mg/l 2,4-D and 40 mg/l acetosyringone for 60 min. Infected explants are plated abaxial side up on agar-solidified co-cultivation medium and incubated at 25° C., in the dark for 4 d.

For selection of transformed tissues, cotyledons washed with 500 mg/l cephotaxine are placed abaxial side up on a medium for induction of somatic embryo formation (Gelrite-solidified MS medium medium containing 30 g/l sucrose, 40 mg/l 2,4-D, 500 mg/l cefotaxime, and 10 mg/l hygromycin) and incubated at 25° C., under a 23-h photoperiod (10-20 $\mu E/m^2/s$) for 2 weeks. After another two weeks of growth under the same conditions in the presence of 25 mg/l hygromycin, the antibiotic-resistant somatic embryos are transferred on MS medium for embryo maturation supplemented with 60 g/l maltose, 500 mg/l cefotaxime, and 10 mg/l hygromycin and grown under the same conditions for 8 weeks with 2-week subculture intervals.

Plant regeneration and selection: The resulting cotyledonary stage embryos are desiccated at 25° C., under a 23-h photoperiod (60-80 $\mu E/m^2/s$) for 5-7 d followed by culture on MS regeneration medium containing 30 g/l sucrose and 500 mg/l cefotaxime for 4-6 weeks for shoot and root development. When the plants are 5-10 cm tall, they are transferred to soil and grown in a greenhouse after acclimatization for 7 d.

Embodiment 1

A transgenic plant comprising a heterologous bicarbonate transporter, wherein the transgenic plant has a CO2 assimilation rate at least 5%, at least 10%, at least 15%, at least 20%, at least 25%, at least 30%, at least 35%, or at least 40% higher than a plant of the same species not comprising the heterologous bicarbonate transporter.

Embodiment 2

A transgenic plant comprising a heterologous bicarbonate transporter, wherein the transgenic plant has a reduced transpiration rate at least 5%, at least 10%, at least 15%, at least 20%, at least 25%, at least 30%, at least 35%, or at least 40% lower than a plant of the same species not comprising the heterologous bicarbonate transporter.

Embodiment 3

A transgenic plant transformed with a recombinant DNA construct comprising a plant-expressible transcription regulatory sequence operatively linked to a polynucleotide encoding a heterologous bicarbonate transporter.

Embodiment 4

The transgenic plant of any one of embodiments 1-3, wherein a heterologous carbonic anhydrase is not present.

Embodiment 5

The transgenic plant of any one of embodiments 1-4, wherein the bicarbonate transporter localizes to a chloroplast envelope membrane.

Embodiment 6

The transgenic plant of any one of embodiments 1-5, wherein the bicarbonate transporter is from a cyanobacterium.

Embodiment 7

The transgenic plant of embodiment 6, wherein the bicarbonate transporter is a BicA polypeptide or a SbtA polypeptide.

Embodiment 8

The transgenic plant of embodiment 7, wherein the BicA polypeptide comprises the amino acid sequence of SEQ ID NO:4, or an amino acid sequence 95% homologous to SEQ ID NO:4.

Embodiment 9

The transgenic plant of embodiment 7, wherein the SbtA polypeptide comprises the amino acid sequence of SEQ ID NO:2, or an amino acid sequence 95% homologous to SEQ ID NO:2.

Embodiment 10

The transgenic plant of any one of embodiments 1-9, wherein a polynucleotide encoding the bicarbonate transporter further comprises a sequence encoding a chloroplast envelope targeting peptide operably linked to a bicarbonate transporter coding sequence.

Embodiment 11

The transgenic plant of embodiment 10, wherein the sequence of the chloroplast envelope targeting peptide comprises amino acids 1 to 110 of SEQ ID NO:10.

Embodiment 12

The transgenic plant of embodiment 11, wherein the bicarbonate transporter is from an algae.

Embodiment 13

The transgenic plant of embodiment 12, wherein the algae is a *Chlamydomonas* species.

Embodiment 14

The transgenic plant of embodiment 13, wherein the bicarbonate transporter is a CCP1 polypeptide, a CCP2 polypeptide, or an LCIA polypeptide.

Embodiment 15

The transgenic plant of embodiment 14, wherein the CCP1 polypeptide comprises the amino acid sequence of SEQ ID NO:6, or an amino acid sequence 95% homologous to SEQ ID NO:6.

Embodiment 16

The transgenic plant of embodiment 14, wherein the LCIA polypeptide comprises the amino acid sequence of SEQ ID NO:8, or an amino acid sequence 95% homologous to SEQ ID NO:8.

Embodiment 17

The transgenic plant of any one of embodiments 1-16, which is an oil crop plant selected from the group consisting of *Borago officinalis, Brassica campestris, Brassica napus, Brassica rapa, Camelina* species, *Cannabis sativa, Carthamus tinctorius, Cocos nucifera, Crambe abyssinica, Cuphea* species, *Elaeis guinensis, Elaeis oleifera, Glycine max, Gossypium hirsutum, Gossypium barbadense, Gossypium herbaceum, Helianthus annuus, Linum usitatissimum, Oenothera biennis, Olea europaea, Oryza sativa, Ricinus communis, Sesamum indicum, Triticum* species, *Zea mays*, walnut and almond.

Embodiment 18

The transgenic plant of any one of embodiments 1-17, wherein the plant is *Camelina sativa.*

Embodiment 19

The transgenic plant of any one of embodiments 1-18 comprising at least two heterologous bicarbonate transporters.

Embodiment 20

A recombinant polynucleotide comprising a nucleic acid sequence encoding a heterologous bicarbonate transporter operatively linked to a plant-expressible transcription regulatory sequence, wherein optionally the nucleic acid sequence encoding the bicarbonate transporter is further operatively linked to a nucleic acid sequence encoding a chloroplast envelope targeting peptide.

Embodiment 21

The recombinant polynucleotide of embodiment 20, wherein the chloroplast envelope targeting peptide is the transit peptide of *Arabidopsis thaliana* Tic20 (atTic20) precursor.

Embodiment 22

The recombinant polynucleotide of embodiment 21, wherein the nucleic acid sequence comprises residues 1-330 of SEQ ID NO:9.

Embodiment 23

The recombinant polynucleotide of any one of embodiments 20-22, wherein the bicarbonate transporter is from a cyanobacterium.

Embodiment 24

The recombinant polynucleotide of any one of embodiments 20-23, wherein the bicarbonate transporter is a BicA polypeptide or a SbtA polypeptide.

Embodiment 25

The recombinant polynucleotide of embodiment 24, wherein the BicA polypeptide comprises the amino acid sequence of SEQ ID NO:4, or an amino acid sequence 95% homologous to SEQ ID NO:4.

Embodiment 26

The recombinant polynucleotide of embodiment 24, wherein the SbtA polypeptide comprises the amino acid sequence of SEQ ID NO:2, or an amino acid sequence 95% homologous to SEQ ID NO:2.

Embodiment 27

The recombinant polynucleotide of embodiment 20, wherein the bicarbonate transporter is from an algae.

Embodiment 28

The recombinant polynucleotide of embodiment 27, wherein the algae is a *Chlamydomonas* species.

Embodiment 29

The recombinant polynucleotide of any one of embodiments 20, 27, or 28, wherein the bicarbonate transporter is a CCP1 polypeptide, a CCP2 polypeptide, or an LCIA polypeptide.

Embodiment 30

The recombinant polynucleotide of embodiment 29, wherein the CCP1 polypeptide comprises the amino acid sequence of SEQ ID NO:6, or an amino acid sequence 95% homologous to SEQ ID NO:6.

Embodiment 31

The recombinant polynucleotide of embodiment 29, wherein the LCIA polypeptide comprises the amino acid sequence of SEQ ID NO:8, or an amino acid sequence 95% homologous to SEQ ID NO:8.

Embodiment 32

The recombinant polynucleotide of any one of embodiments 20-31 further comprising a nucleic acid encoding an epitope tag selected from FLAG, 6×His, glutathione-S-transferase (GST), HA, cMyc, or AcV5.

Embodiment 33

A plant-expressible expression vector comprising the recombinant polynucleotide of any one of embodiments 20-32.

Embodiment 34

The plant-expressible expression vector of embodiment 33 comprising a pEarleyGate vector.

Embodiment 35

A method of producing a transformed plant having enhanced photosynthesis, the method comprises transforming a plant cell with the recombinant polynucleotide of any one of embodiments 20-32 or the expression vector of any one of embodiments 33-34; growing a plant from the plant cell until the plant produces seed; and selecting seeds from a plant in which photosynthesis is enhanced in comparison with a corresponding plant that is not expressing the heterologous bicarbonate transporter.

Embodiment 36

The method of embodiment 35, wherein the plant is an oil crop plant selected from the group consisting of *Borago*

*officinalis, Brassica campestris, Brassica napus, Brassica rapa, Camelina* species, *Cannabis sativa, Carthamus tinctorius, Cocos nucifera, Crambe abyssinica, Cuphea* species, *Elaeis guinensis, Elaeis oleifera, Glycine max, Gossypium hirsutum, Gossypium barbadense, Gossypium herbaceum, Helianthus annuus, Linum usitatissimum, Oenothera biennis, Olea europaea, Oryza sativa, Ricinus communis, Sesamum indicum, Triticum* species, *Zea mays*, walnut and almond.

Embodiment 37

The method of embodiment 36, wherein the plant is a *Camelina.*

Embodiment 38

The method of any one of embodiments 35-37, wherein enhancement of photosynthesis is measured as an increase in CO2 assimilation rate or a reduction in transpiration rate relative to wild type.

Embodiment 39

The method of any one of embodiments 35-38, wherein photosynthesis is enhanced by at least 5%.

Embodiment 40

A chimeric protein comprising *Arabidopsis thaliana* atTic20 transit peptide and a membrane protein heterologous to chloroplast envelope membranes.

As used herein, the singular terms "a", "an," and "the" include the plural reference unless the context clearly indicates otherwise.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. The modifier "about" used in connection with a quantity is inclusive of the stated value and has the meaning dictated by the context (e.g., includes the degree of error associated with measurement of the particular quantity).

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A transgenic plant transformed with a recombinant DNA construct comprising a plant-expressible transcription regulatory sequence operatively linked to a polynucleotide encoding an algal CCP1 or CCP2 polypeptide comprising an amino acid sequence that is at least 80% homologous to SEQ ID NO: 6, wherein the transgenic plant has a $CO_2$ assimilation rate at least 5% higher than a plant of the same species not transformed with the recombinant DNA construct and a reduced transpiration rate at least 5% lower than a plant of the same species not transformed with the recombinant DNA construct.

2. The transgenic plant of claim 1, wherein the algae is a *Chlamydomonas* species.

3. The transgenic plant of claim 1, wherein the CCP1 polypeptide comprises the amino acid sequence of SEQ ID NO:6.

4. The transgenic plant of claim 1, which is an oil crop plant selected from the group consisting of *Borago officinalis, Brassica campestris, Brassica napus, Brassica rapa, Camelina species, Cannabis sativa, Carthamus tinctorius, Cocos nucifera, Crambe abyssinica, Cuphea species, Elaeis guinensis, Elaeis oleifera, Glycine max, Gossypium hirsutum, Gossypium barbadense, Gossypium herbaceum, Helianthus annuus, Linum usitatissimum, Oenothera biennis, Olea europaea, Oryza sativa, Ricinus communis, Sesamum indicum, Triticum* species, *Zea mays*, walnut and almond.

5. The transgenic plant of claim 4, wherein the plant is *Camelina sativa.*

6. A method of producing a transformed plant having enhanced photosynthesis, the method comprising transforming a plant cell with a recombinant polynucleotide comprising a nucleic acid sequence encoding an algal CCP1 or CCP2 polypeptide, comprising an amino acid sequence that is at least 80% homologous to SEQ ID NO:6, operatively linked to a plant-expressible promoter, wherein the nucleic acid sequence encoding the algal CCP1 or CCP2 polypeptide is further operatively linked to a transcription terminator;

growing a plant from the plant cell until the plant produces seed; and selecting seeds from a plant in which the transgenic plant has a $CO_2$ assimilation rate higher than a plant of the same species not comprising the algal CCP1 or CCP2 polypeptide and a reduced transpiration rate lower than a plant of the same species not comprising the algal CCP1 or CCP2 polypeptide.

7. The method of claim 6, wherein the plant is an oil crop plant selected from the group consisting of *Borago officinalis, Brassica campestris, Brassica napus, Brassica rapa, Camelina species, Cannabis sativa, Carthamus tinctorius, Cocos nucifera, Crambe abyssinica, Cuphea species, Elaeis guinensis, Elaeis oleifera, Glycine max, Gossypium hirsutum, Gossypium barbadense, Gossypium herbaceum, Helianthus annuus, Linum usitatissimum, Oenothera biennis, Olea europaea, Oryza sativa, Ricinus communis, Sesamum indicum, Triticum* species, *Zea mays*, walnut and almond.

8. The method of claim 7, wherein the plant is a *Camelina*.

9. The method of claim 6, wherein the transgenic plant has a $CO_2$ assimilation rate at least 5% higher than a plant of the same species not comprising the algal CCP1 or CCP2 polypeptide and a reduced transpiration rate at least 5% lower than a plant of the same species not comprising the algal CCP1 or CCP2 polypeptide.

10. The method of claim 6 wherein the CCP1 polypeptide comprises the amino acid sequence of SEQ ID NO:6.

* * * * *

SEQUENCE LISTING

<160> NUMBER OF SEQ ID NOS: 11

<210> SEQ ID NO 1
<211> LENGTH: 1122
<212> TYPE: DNA
<213> ORGANISM: Synechocystis PCC6803

<400> SEQUENCE: 1
atggatttcc tcagtaactt tctcactgat tttgtaggtc aactacaatc accaacacta 60
gcttttctca ttggaggaat ggtgattgct gcgttgggga cacagctggt gatacctgag 120
gctatttcca ccatcatcgt tttcatgctc ctcacaaaga ttggattgac cgggggaatg 180
gccatccgca attctaattt gactgagatg ttattaccag ttgcgttctc tgttattctc 240
ggtattctta ttgtattcat agctcgcttt actttggcca agttgccaaa tgtgaggacc 300
gtggatgcac tcgcaacggg aggtttgttc ggtgccgtct ctggatctac gatggctgct 360
gcattgacta ccttggaaga gagcaaaatc agttacgagg cgtgggcagg ggctttgtat 420
ccctttatgg acatccctgc attggttaca gcgattgtcg tcgctaatat ttatttgaat 480
aaacgcaaga gaaagagcgc agcggctagc atagaggaat cattttcaaa gcaacctgtt 540
gcagctggag attatggcga tcagaccgat tacccgagaa ctcgacagga atacctttct 600
cagcaagaac cggaggataa cagggttaaa atttggccaa ttatagaaga atcacttcag 660
ggaccagcat tgtctgcaat gttgcttggc cttgctcttg gcatcttcac taaaccagaa 720
tctgtatatg aaggttttta tgaccctta ttccgggggt tgctatcaat cctgatgctt 780
atcatgggga tggaggcttg gtctagaatc ggcgaattgc gtaaggttgc tcagtggtac 840

-continued

```
gttgtgtatt ctcttatcgc accaatcgtg catggtttta tcgctttcgg tttaggtatg    900

attgcacatt atgccactgg attttctcta ggaggcgttg ttgtgctcgc cgtgatcgca    960

gcttctagtt ctgacatttc aggacctccg acattgaggg caggaattcc ttccgcaaac   1020

ccatcggcgt acatcggaag ttctactgcc atcggtacac ctattgcaat cggggtgtgt   1080

atacccctgt ttattggtct agctcaaacc cttggagctg ga                      1122


<210> SEQ ID NO 2
<211> LENGTH: 374
<212> TYPE: PRT
<213> ORGANISM: Synechocystis PCC6803

<400> SEQUENCE: 2

Met Asp Phe Leu Ser Asn Phe Leu Thr Asp Phe Val Gly Gln Leu Gln
1               5                   10                  15

Ser Pro Thr Leu Ala Phe Leu Ile Gly Gly Met Val Ile Ala Ala Leu
            20                  25                  30

Gly Thr Gln Leu Val Ile Pro Glu Ala Ile Ser Thr Ile Ile Val Phe
        35                  40                  45

Met Leu Leu Thr Lys Ile Gly Leu Thr Gly Gly Met Ala Ile Arg Asn
    50                  55                  60

Ser Asn Leu Thr Glu Met Leu Leu Pro Val Ala Phe Ser Val Ile Leu
65                  70                  75                  80

Gly Ile Leu Ile Val Phe Ile Ala Arg Phe Thr Leu Ala Lys Leu Pro
                85                  90                  95

Asn Val Arg Thr Val Asp Ala Leu Ala Thr Gly Gly Leu Phe Gly Ala
            100                 105                 110

Val Ser Gly Ser Thr Met Ala Ala Ala Leu Thr Thr Leu Glu Glu Ser
        115                 120                 125

Lys Ile Ser Tyr Glu Ala Trp Ala Gly Ala Leu Tyr Pro Phe Met Asp
    130                 135                 140

Ile Pro Ala Leu Val Thr Ala Ile Val Val Ala Asn Ile Tyr Leu Asn
145                 150                 155                 160

Lys Arg Lys Arg Lys Ser Ala Ala Ala Ser Ile Glu Glu Ser Phe Ser
                165                 170                 175

Lys Gln Pro Val Ala Ala Gly Asp Tyr Gly Asp Gln Thr Asp Tyr Pro
            180                 185                 190

Arg Thr Arg Gln Glu Tyr Leu Ser Gln Gln Glu Pro Glu Asp Asn Arg
        195                 200                 205

Val Lys Ile Trp Pro Ile Ile Glu Glu Ser Leu Gln Gly Pro Ala Leu
    210                 215                 220

Ser Ala Met Leu Leu Gly Leu Ala Leu Gly Ile Phe Thr Lys Pro Glu
225                 230                 235                 240

Ser Val Tyr Glu Gly Phe Tyr Asp Pro Leu Phe Arg Gly Leu Leu Ser
                245                 250                 255

Ile Leu Met Leu Ile Met Gly Met Glu Ala Trp Ser Arg Ile Gly Glu
            260                 265                 270

Leu Arg Lys Val Ala Gln Trp Tyr Val Val Tyr Ser Leu Ile Ala Pro
        275                 280                 285

Ile Val His Gly Phe Ile Ala Phe Gly Leu Gly Met Ile Ala His Tyr
    290                 295                 300

Ala Thr Gly Phe Ser Leu Gly Gly Val Val Val Leu Ala Val Ile Ala
305                 310                 315                 320
```

-continued

```
Ala Ser Ser Ser Asp Ile Ser Gly Pro Pro Thr Leu Arg Ala Gly Ile
                325                 330                 335

Pro Ser Ala Asn Pro Ser Ala Tyr Ile Gly Ser Ser Thr Ala Ile Gly
            340                 345                 350

Thr Pro Ile Ala Ile Gly Val Cys Ile Pro Leu Phe Ile Gly Leu Ala
        355                 360                 365

Gln Thr Leu Gly Ala Gly
    370


<210> SEQ ID NO 3
<211> LENGTH: 1698
<212> TYPE: DNA
<213> ORGANISM: Synechococcus PCC7002

<400> SEQUENCE: 3

atgcaaatca ccaacaaaat ccactttagg aacataagag gagatatctt cggtgggttg     60

actgcggctg tgatagccct tcctatggca ttagcttttg gtgtcgcatc tggggcagga    120

gctgaggcag ggctgtgggg tgcagtcctt gtcggattct tcgctgccct ttttggaggg    180

actcctacgc ttatatctga accgacaggg cctatgacag tggtgatgac agcggttata    240

gctcatttca ctgcgtctgc tgctactcca gaagaaggct tggcaattgc ttttactgta    300

gttatgatgg caggtgtgtt ccaaatcatc tttggtagcc ttaaactcgg caaatacgtg    360

acgatgatgc cgtatacagt gattagcggt tttatgtccg gtatcggaat cattcttgtg    420

atactacaat tagcaccatt tctcggtcaa gcatcgccag gtggaggagt cataggtaca    480

ttgcagaatc ttcccacact gctgtccaat atacagcctg gcgaaactgc attggcactc    540

ggtacagttg cgataatctg gtttatgccc gagaaattca agaaggttat tcctcctcaa    600

cttgttgcac tcgttctagg gaccgttata gctttctttg tttttccccc tgaagtctcc    660

gatttgagaa ggattggaga gatccgtgct ggattcccag agctagttcg accgtcattc    720

tctccggttg agtttcagag gatgattctg gatgctgctg tactcggtat gctcggatgt    780

atagacgctc ttttgacaag cgttgttgcg gatagcctga cccgaacaga gcataacagc    840

aataaggaac taattggaca gggattgggc aatttgtttt cgggtctttt cggtggaatc    900

gccggagctg gtgctacaat gggaaccgtg gtcaacattc agtcgggagg taggactgct    960

ttgtcaggtc ttgtgcgtgc attcgttttg ctcgtcgtca ttctcggagc tgctagcctt   1020

acagcaacta taccgcttgc tgttctggcc ggcatcgcat tcaaagttgg agtagacatc   1080

attgattggt cattcttgaa acgtgctcac gaaatttcac caaagggtgc gctgatcatg   1140

tatggcgtta ttctcctcac tgttttggtg gatcttatcg ttgcagtggg agtgggtgtg   1200

ttcgtcgcta atgttctcac gatagagaga atgtctaatc tgcaatccga gaaagtccaa   1260

actgtttctg atgccgatga caacatccga ctcacgacta ctgaaaaacg ttggttggat   1320

gagggacagg gtagagtatt gctatttcag ctttctggcc caatgatctt tggagtggcc   1380

aaagctattg caagagagca caatgcgatg ggagattgtg atgctttggt tttcgacatt   1440

ggtgaagtac cacatatggg agttacggct agtcttgcat tagagaatgc gattgaagag   1500

gcattggaca aggaacgtca agtctacatc gtaggtgctg ccggacaaac cagaagaaga   1560

ttggaaaagc ttaagctgtt taagcgtgtg ccaccagata agtgcttgat gagtagggaa   1620

gaggcgttga agaacgctgt actaggtatc tacccgcatt tggctgacgg agttaccgct   1680

ccttcttcag agatgggt                                                 1698
```

<210> SEQ ID NO 4
<211> LENGTH: 566
<212> TYPE: PRT
<213> ORGANISM: Synechococcus PCC7002

<400> SEQUENCE: 4

Met Gln Ile Thr Asn Lys Ile His Phe Arg Asn Ile Arg Gly Asp Ile
1 5 10 15

Phe Gly Gly Leu Thr Ala Ala Val Ile Ala Leu Pro Met Ala Leu Ala
20 25 30

Phe Gly Val Ala Ser Gly Ala Gly Ala Glu Ala Gly Leu Trp Gly Ala
35 40 45

Val Leu Val Gly Phe Phe Ala Ala Leu Phe Gly Gly Thr Pro Thr Leu
50 55 60

Ile Ser Glu Pro Thr Gly Pro Met Thr Val Val Met Thr Ala Val Ile
65 70 75 80

Ala His Phe Thr Ala Ser Ala Ala Thr Pro Glu Glu Gly Leu Ala Ile
85 90 95

Ala Phe Thr Val Val Met Met Ala Gly Val Phe Gln Ile Ile Phe Gly
100 105 110

Ser Leu Lys Leu Gly Lys Tyr Val Thr Met Met Pro Tyr Thr Val Ile
115 120 125

Ser Gly Phe Met Ser Gly Ile Gly Ile Ile Leu Val Ile Leu Gln Leu
130 135 140

Ala Pro Phe Leu Gly Gln Ala Ser Pro Gly Gly Gly Val Ile Gly Thr
145 150 155 160

Leu Gln Asn Leu Pro Thr Leu Leu Ser Asn Ile Gln Pro Gly Glu Thr
165 170 175

Ala Leu Ala Leu Gly Thr Val Ala Ile Ile Trp Phe Met Pro Glu Lys
180 185 190

Phe Lys Lys Val Ile Pro Pro Gln Leu Val Ala Leu Val Leu Gly Thr
195 200 205

Val Ile Ala Phe Phe Val Phe Pro Pro Glu Val Ser Asp Leu Arg Arg
210 215 220

Ile Gly Glu Ile Arg Ala Gly Phe Pro Glu Leu Val Arg Pro Ser Phe
225 230 235 240

Ser Pro Val Glu Phe Gln Arg Met Ile Leu Asp Ala Ala Val Leu Gly
245 250 255

Met Leu Gly Cys Ile Asp Ala Leu Leu Thr Ser Val Val Ala Asp Ser
260 265 270

Leu Thr Arg Thr Glu His Asn Ser Asn Lys Glu Leu Ile Gly Gln Gly
275 280 285

Leu Gly Asn Leu Phe Ser Gly Leu Phe Gly Gly Ile Ala Gly Ala Gly
290 295 300

Ala Thr Met Gly Thr Val Val Asn Ile Gln Ser Gly Gly Arg Thr Ala
305 310 315 320

Leu Ser Gly Leu Val Arg Ala Phe Val Leu Leu Val Val Ile Leu Gly
325 330 335

Ala Ala Ser Leu Thr Ala Thr Ile Pro Leu Ala Val Leu Ala Gly Ile
340 345 350

Ala Phe Lys Val Gly Val Asp Ile Ile Asp Trp Ser Phe Leu Lys Arg
355 360 365

Ala His Glu Ile Ser Pro Lys Gly Ala Leu Ile Met Tyr Gly Val Ile
370 375 380

-continued

```
Leu Leu Thr Val Leu Val Asp Leu Ile Val Ala Val Gly Val Gly Val
385                 390                 395                 400

Phe Val Ala Asn Val Leu Thr Ile Glu Arg Met Ser Asn Leu Gln Ser
                405                 410                 415

Glu Lys Val Gln Thr Val Ser Asp Ala Asp Asp Asn Ile Arg Leu Thr
            420                 425                 430

Thr Thr Glu Lys Arg Trp Leu Asp Glu Gly Gln Gly Arg Val Leu Leu
        435                 440                 445

Phe Gln Leu Ser Gly Pro Met Ile Phe Gly Val Ala Lys Ala Ile Ala
    450                 455                 460

Arg Glu His Asn Ala Met Gly Asp Cys Asp Ala Leu Val Phe Asp Ile
465                 470                 475                 480

Gly Glu Val Pro His Met Gly Val Thr Ala Ser Leu Ala Leu Glu Asn
                485                 490                 495

Ala Ile Glu Glu Ala Leu Asp Lys Glu Arg Gln Val Tyr Ile Val Gly
            500                 505                 510

Ala Ala Gly Gln Thr Arg Arg Arg Leu Glu Lys Leu Lys Leu Phe Lys
        515                 520                 525

Arg Val Pro Pro Asp Lys Cys Leu Met Ser Arg Glu Glu Ala Leu Lys
    530                 535                 540

Asn Ala Val Leu Gly Ile Tyr Pro His Leu Ala Asp Gly Val Thr Ala
545                 550                 555                 560

Pro Ser Ser Glu Met Gly
                565
```

<210> SEQ ID NO 5
<211> LENGTH: 1074
<212> TYPE: DNA
<213> ORGANISM: Chlamydomonas reinhardtii

<400> SEQUENCE: 5

```
atgtctagtg atgccatgac catcaatgag tctcttatgg aagtcgaaca tactccagct      60

gtgcataaaa ggattcttga cattttaccg ggtatcagtg gcggggttgc cagagttatg     120

ataggtcagc ccttcgacac aatcaaagtg cgtctacaag tgttggggca gggtacggct     180

ctcgctgcca aacttcctcc tagtgaagtt tacaaggaca gcatggattg cattcgtaag     240

atgattaagt cggagggtcc actaagcttt tacaagggaa cagttgcccc actcgtcgga     300

aacatggtat tgcttggcat ccattttccg gtcttttccg cggttagaaa gcagttggag     360

ggtgatgatc attactctaa cttttcacac gccaatgtac tgcttagcgg cgctgcggca     420

ggagctgcgg gatcactcat ttcggctcct gttgaactgg ttagaacgaa aatgcaaatg     480

caaaggcgag ccgcacttgc gggtacagtg gctgctggtg cagctgcatc tgctggagct     540

gaggagttct ataagggaag tcttgattgt ttcaaacaag ttatgtctaa gcatgggatt     600

aaaggattgt ataggggttt tacttcaact atactacgag atatgcaggg ttatgcttgg     660

ttcttcctcg gatatgaggc gactgtcaat cacttcttgc aaaatgcggg accaggtgtt     720

cataccaagg ctgacttgaa ttaccttcaa gtgatggccg ctggggttgt tgctggattt     780

ggattatggg gctccatgtt tccaatcgat accatcaaat ctaaactcca agccgatagc     840

tttgccaaac ctcaatattc atccacaatg gattgtctta agaaagtatt agcaagtgag     900

ggacaggccg gcttgtggag agggttcagc gcagcaatgt atagagcaat accggtgaac     960

gctggcattt tcctcgctgt tgaagggaca cgtcagggta taaagtggta cgaggaaaac    1020

gtggaacaca tctacggagg tgtcattggt cccgctacgc ctacggcagc acaa          1074
```

<210> SEQ ID NO 6
<211> LENGTH: 358
<212> TYPE: PRT
<213> ORGANISM: Chlamydomonas reinhardtii

<400> SEQUENCE: 6

```
Met Ser Ser Asp Ala Met Thr Ile Asn Glu Ser Leu Met Glu Val Glu
1               5                   10                  15

His Thr Pro Ala Val His Lys Arg Ile Leu Asp Ile Leu Pro Gly Ile
            20                  25                  30

Ser Gly Gly Val Ala Arg Val Met Ile Gly Gln Pro Phe Asp Thr Ile
        35                  40                  45

Lys Val Arg Leu Gln Val Leu Gly Gln Gly Thr Ala Leu Ala Ala Lys
    50                  55                  60

Leu Pro Pro Ser Glu Val Tyr Lys Asp Ser Met Asp Cys Ile Arg Lys
65                  70                  75                  80

Met Ile Lys Ser Glu Gly Pro Leu Ser Phe Tyr Lys Gly Thr Val Ala
                85                  90                  95

Pro Leu Val Gly Asn Met Val Leu Leu Gly Ile His Phe Pro Val Phe
            100                 105                 110

Ser Ala Val Arg Lys Gln Leu Glu Gly Asp Asp His Tyr Ser Asn Phe
        115                 120                 125

Ser His Ala Asn Val Leu Leu Ser Gly Ala Ala Ala Gly Ala Ala Gly
    130                 135                 140

Ser Leu Ile Ser Ala Pro Val Glu Leu Val Arg Thr Lys Met Gln Met
145                 150                 155                 160

Gln Arg Arg Ala Ala Leu Ala Gly Thr Val Ala Ala Gly Ala Ala Ala
                165                 170                 175

Ser Ala Gly Ala Glu Glu Phe Tyr Lys Gly Ser Leu Asp Cys Phe Lys
            180                 185                 190

Gln Val Met Ser Lys His Gly Ile Lys Gly Leu Tyr Arg Gly Phe Thr
        195                 200                 205

Ser Thr Ile Leu Arg Asp Met Gln Gly Tyr Ala Trp Phe Phe Leu Gly
    210                 215                 220

Tyr Glu Ala Thr Val Asn His Phe Leu Gln Asn Ala Gly Pro Gly Val
225                 230                 235                 240

His Thr Lys Ala Asp Leu Asn Tyr Leu Gln Val Met Ala Ala Gly Val
                245                 250                 255

Val Ala Gly Phe Gly Leu Trp Gly Ser Met Phe Pro Ile Asp Thr Ile
            260                 265                 270

Lys Ser Lys Leu Gln Ala Asp Ser Phe Ala Lys Pro Gln Tyr Ser Ser
        275                 280                 285

Thr Met Asp Cys Leu Lys Lys Val Leu Ala Ser Glu Gly Gln Ala Gly
    290                 295                 300

Leu Trp Arg Gly Phe Ser Ala Ala Met Tyr Arg Ala Ile Pro Val Asn
305                 310                 315                 320

Ala Gly Ile Phe Leu Ala Val Glu Gly Thr Arg Gln Gly Ile Lys Trp
                325                 330                 335

Tyr Glu Glu Asn Val Glu His Ile Tyr Gly Gly Val Ile Gly Pro Ala
            340                 345                 350

Thr Pro Thr Ala Ala Gln
        355
```

-continued

<210> SEQ ID NO 7
<211> LENGTH: 1008
<212> TYPE: DNA
<213> ORGANISM: Chlamydomonas reinhardtii

<400> SEQUENCE: 7
atgcaaacca caatgacacg tccttgtctc gctcaaccag ttctgcgatc cagggttttg 60
agatccccta tgagggtggt tgctgcgtct gctccaacag ccgttactac tgtggtgact 120
tctaacggga atggtaatgg ccacttccaa gctgctacta caccagttcc cccgacacct 180
gctccggtgg cagtatctgc tccagtgcgt gcagtgagtg tgctcacgcc tcctcaagtt 240
tacgaaaatg ccataaacgt gggtgcgtat aaggctgggt taactccatt agctaccttc 300
gtgcagggta ttcaagcagg tgcgtatata gccttcggag cctttctcgc catcagtgtt 360
ggaggaaata tccctggcgt cgctgctgca aatccagggc tcgctaaact tctttttgct 420
ctagtctttc cagttggtct ttcaatggtc accaattgcg gagcagaatt gttcactgga 480
aacactatga tgcttacgtg tgctctcata gagaaaaagg caacatgggg tcagttgcta 540
aagaattgga gcgtttcgta ctttgggaac tttgtcggta gtattgcaat ggtagctgct 600
gttgtagcta ctggttgttt gacaacgaac actctgcctg ttcagatggc aactctaaaa 660
gctaaccttg gcttcacaga ggttctgagc agatcaatct tgtgcaattg gctcgtttgt 720
tgtgctgtgt ggagcgcctc agcagcaaca tctttaccgg gaagaatttt ggccttatgg 780
ccctgcataa cggcatttgt cgcaattgga ctagagcatt ctgttgcgaa tatgttcgtc 840
attccgttgg gtatgatgct tggagcggaa gtcacttggt cgcagttttt ctttaacaac 900
cttatcccag taacccttgg aaataccatc gctggcgtac ttatgatggc tattgcatat 960
tcaatctctt tcggatcgtt aggaaagtcc gcaaaacctg ccaccgcg 1008

<210> SEQ ID NO 8
<211> LENGTH: 336
<212> TYPE: PRT
<213> ORGANISM: Chlamydomonas reinhardtii

<400> SEQUENCE: 8

Met Gln Thr Thr Met Thr Arg Pro Cys Leu Ala Gln Pro Val Leu Arg
1 5 10 15

Ser Arg Val Leu Arg Ser Pro Met Arg Val Val Ala Ala Ser Ala Pro
20 25 30

Thr Ala Val Thr Thr Val Val Thr Ser Asn Gly Asn Gly Asn Gly His
35 40 45

Phe Gln Ala Ala Thr Thr Pro Val Pro Pro Thr Pro Ala Pro Val Ala
50 55 60

Val Ser Ala Pro Val Arg Ala Val Ser Val Leu Thr Pro Pro Gln Val
65 70 75 80

Tyr Glu Asn Ala Ile Asn Val Gly Ala Tyr Lys Ala Gly Leu Thr Pro
85 90 95

Leu Ala Thr Phe Val Gln Gly Ile Gln Ala Gly Ala Tyr Ile Ala Phe
100 105 110

Gly Ala Phe Leu Ala Ile Ser Val Gly Gly Asn Ile Pro Gly Val Ala
115 120 125

Ala Ala Asn Pro Gly Leu Ala Lys Leu Leu Phe Ala Leu Val Phe Pro
130 135 140

Val Gly Leu Ser Met Val Thr Asn Cys Gly Ala Glu Leu Phe Thr Gly
145 150 155 160

-continued

```
Asn Thr Met Met Leu Thr Cys Ala Leu Ile Glu Lys Lys Ala Thr Trp
                165                 170                 175

Gly Gln Leu Leu Lys Asn Trp Ser Val Ser Tyr Phe Gly Asn Phe Val
            180                 185                 190

Gly Ser Ile Ala Met Val Ala Ala Val Val Ala Thr Gly Cys Leu Thr
        195                 200                 205

Thr Asn Thr Leu Pro Val Gln Met Ala Thr Leu Lys Ala Asn Leu Gly
    210                 215                 220

Phe Thr Glu Val Leu Ser Arg Ser Ile Leu Cys Asn Trp Leu Val Cys
225                 230                 235                 240

Cys Ala Val Trp Ser Ala Ser Ala Ala Thr Ser Leu Pro Gly Arg Ile
                245                 250                 255

Leu Ala Leu Trp Pro Cys Ile Thr Ala Phe Val Ala Ile Gly Leu Glu
            260                 265                 270

His Ser Val Ala Asn Met Phe Val Ile Pro Leu Gly Met Met Leu Gly
        275                 280                 285

Ala Glu Val Thr Trp Ser Gln Phe Phe Phe Asn Asn Leu Ile Pro Val
    290                 295                 300

Thr Leu Gly Asn Thr Ile Ala Gly Val Leu Met Met Ala Ile Ala Tyr
305                 310                 315                 320

Ser Ile Ser Phe Gly Ser Leu Gly Lys Ser Ala Lys Pro Ala Thr Ala
                325                 330                 335
```

```
<210> SEQ ID NO 9
<211> LENGTH: 825
<212> TYPE: DNA
<213> ORGANISM: Arabidopsis thaliana

<400> SEQUENCE: 9

atgataactg gatacagcac gccaagtgca catgttctaa tgagctctcg ggcattcaag     60

tcatcatcat atagagctgc agcaggacag actcaacatt atcttgctcg aagttcattg    120

cctgtcgtaa agaactcgtg gggatcacca ccttcacctt tcaatgagct tccgagagtg    180

tcaagaggtg tgcctctgtc atatctctca gcctcgtctt ctctgcttct gaatggagaa    240

caaggtagtc tatctggtac attacctgtg ttacctgtcc gcagaaaaac tcttttgact    300

ccacgagcgt caaaagatgt accttctagc ttccgatttc ccccgatgac caagaagcca    360

caatggtggt ggagaacttt ggcttgcctg ccttacctaa tgccactgca tgaaacttgg    420

atgtatgcag aaaccgctta ccatctccac ccattcctag aagattttga attcttaacc    480

tacccatttc taggcgccat aggaagatta ccaagctggt tcctcatggc ttactttttt    540

gtagcttatc tagggatagt gcgaagaaaa gaatggcctc acttcttcag gttccatgta    600

gtgatgggta tgctgcttga aatcgcactc caggttatag ggaccgttag caagtggatg    660

cctcttggag tctattgggg taagtttggg atgcatttct ggactgctgt tgcgtttgct    720

tatctgttta ccgtccttga aagcatacgg tgtgcacttg cgggtatgta cgcagacatc    780

ccgtttgtct gtgatgctgc ctatatccag attccgtacg actaa                    825


<210> SEQ ID NO 10
<211> LENGTH: 274
<212> TYPE: PRT
<213> ORGANISM: Arabidopsis thaliana
```

<400> SEQUENCE: 10

```
Met Ile Thr Gly Tyr Ser Thr Pro Ser Ala His Val Leu Met Ser Ser
1               5                   10                  15

Arg Ala Phe Lys Ser Ser Ser Tyr Arg Ala Ala Ala Gly Gln Thr Gln
            20                  25                  30

His Tyr Leu Ala Arg Ser Ser Leu Pro Val Val Lys Asn Ser Trp Gly
        35                  40                  45

Ser Pro Pro Ser Pro Phe Asn Glu Leu Pro Arg Val Ser Arg Gly Val
    50                  55                  60

Pro Leu Ser Tyr Leu Ser Ala Ser Ser Ser Leu Leu Leu Asn Gly Glu
65                  70                  75                  80

Gln Gly Ser Leu Ser Gly Thr Leu Pro Val Leu Pro Val Arg Arg Lys
                85                  90                  95

Thr Leu Leu Thr Pro Arg Ala Ser Lys Asp Val Pro Ser Ser Phe Arg
            100                 105                 110

Phe Pro Pro Met Thr Lys Lys Pro Gln Trp Trp Trp Arg Thr Leu Ala
        115                 120                 125

Cys Leu Pro Tyr Leu Met Pro Leu His Glu Thr Trp Met Tyr Ala Glu
    130                 135                 140

Thr Ala Tyr His Leu His Pro Phe Leu Glu Asp Phe Glu Phe Leu Thr
145                 150                 155                 160

Tyr Pro Phe Leu Gly Ala Ile Gly Arg Leu Pro Ser Trp Phe Leu Met
                165                 170                 175

Ala Tyr Phe Phe Val Ala Tyr Leu Gly Ile Val Arg Arg Lys Glu Trp
            180                 185                 190

Pro His Phe Phe Arg Phe His Val Val Met Gly Met Leu Leu Glu Ile
        195                 200                 205

Ala Leu Gln Val Ile Gly Thr Val Ser Lys Trp Met Pro Leu Gly Val
    210                 215                 220

Tyr Trp Gly Lys Phe Gly Met His Phe Trp Thr Ala Val Ala Phe Ala
225                 230                 235                 240

Tyr Leu Phe Thr Val Leu Glu Ser Ile Arg Cys Ala Leu Ala Gly Met
                245                 250                 255

Tyr Ala Asp Ile Pro Phe Val Cys Asp Ala Ala Tyr Ile Gln Ile Pro
            260                 265                 270

Tyr Asp
```

<210> SEQ ID NO 11
<211> LENGTH: 1485
<212> TYPE: DNA
<213> ORGANISM: Artificial Sequence
<220> FEATURE:
<223> OTHER INFORMATION: synthetic construct atTic20TP_SbtA_cMyc
<220> FEATURE:
<221> NAME/KEY: transit_peptide
<222> LOCATION: (1)..(330)
<223> OTHER INFORMATION: from atTic20
<220> FEATURE:
<221> NAME/KEY: misc_feature
<222> LOCATION: (331)..(1452)
<223> OTHER INFORMATION: cds of SbtA gene
<220> FEATURE:
<221> NAME/KEY: misc_feature
<222> LOCATION: (1453)..(1485)
<223> OTHER INFORMATION: cMyc tag -continued

<400> SEQUENCE: 11

```
atgatcaccg gttattcaac acctagtgct catgttctga tgtcaagtag ggcctttaag      60
tcctcgtcgt atagagctgc agccgggcag acacaacatt atctggccag gagttctctc     120
ccggtcgtga aaaacagttg gggatcgccc ccatctcctt ttaacgagtt gccacgtgtg     180
tcaagaggcg ttcctttatc gtacttgtcc gcatcttctt ctctacttct taacggggaa     240
caaggatcct taagcggcac tctaccagtg ttgcctgtca ggcgaaagac tcttcttact     300
ccaagggcct ctaaagatgt tccttcttcc atggatttcc tcagtaactt tctcactgat     360
tttgtaggtc aactacaatc accaacacta gcttttctca ttggaggaat ggtgattgct     420
gcgttgggga cacagctggt gatacctgag gctatttcca ccatcatcgt tttcatgctc     480
ctcacaaaga ttggattgac cgggggaatg gccatccgca attctaattt gactgagatg     540
ttattaccag ttgcgttctc tgttattctc ggtattctta ttgtattcat agctcgcttt     600
actttggcca agttgccaaa tgtgaggacc gtggatgcac tcgcaacggg aggtttgttc     660
ggtgccgtct ctggatctac gatggctgct gcattgacta ccttggaaga gagcaaaatc     720
agttacgagg cgtgggcagg ggctttgtat cccctttatgg acatccctgc attggttaca    780
gcgattgtcg tcgctaatat ttatttgaat aaacgcaaga gaaagagcgc agcggctagc     840
atagaggaat cattttcaaa gcaacctgtt gcagctggag attatggcga tcagaccgat     900
tacccgagaa ctcgacagga atacctttct cagcaagaac cggaggataa cagggttaaa     960
atttggccaa ttatagaaga atcacttcag ggaccagcat tgtctgcaat gttgcttggc    1020
cttgctcttg gcatcttcac taaaccagaa tctgtatatg aaggttttta tgacccttta    1080
ttccgggggt tgctatcaat cctgatgctt atcatgggga tggaggcctg gtctagaatc    1140
ggcgaattgc gtaaggttgc tcagtggtac gttgtgtatt ctcttatcgc accaatcgtg    1200
catggtttta tcgctttcgg tttaggtatg attgcacatt atgccactgg attttctcta    1260
ggaggcgttg ttgtgctcgc cgtgatcgca gcttctagtt ctgacatttc aggacctccg    1320
acattgaggg caggaattcc ttccgcaaac ccatcggcgt acatcggaag ttctactgcc    1380
atcggtacac ctattgcaat cggggtgtgt ataccccctgt ttattggtct agctcaaacc   1440
cttggagctg gagaacagaa actgatctct gaagaagatc tgtga                    1485
```